US012714717B2

(12) United States Patent
Kim et al.

(10) Patent No.: US 12,714,717 B2
(45) **Date of Patent: *Aug. 25, 2026**

(54) 3α-OH-5β-PREGNAN-20-ONE COMPOSITIONS AND METHODS FOR TREATING CENTRAL NERVOUS SYSTEM DISORDERS

(71) Applicant: Lipocine Inc., Salt Lake City, UT (US)

(72) Inventors: Kilyoung Kim, Salt Lake City, UT (US); Kongnara Papangkorn, Salt Lake City, UT (US); Kiran Kumar Vangara, Salt Lake City, UT (US); Nachiappan Chidambaram, Salt Lake City, UT (US); Mahesh V. Patel, Salt Lake City, UT (US)

( * ) Notice: Subject to any disclaimer, the term of this patent is extended or adjusted under 35 U.S.C. 154(b) by 275 days.

This patent is subject to a terminal disclaimer.

(21) Appl. No.: 17/706,210

(22) Filed: Mar. 28, 2022

(65) Prior Publication Data

US 2023/0321116 A1 Oct. 12, 2023

Related U.S. Application Data

(60) Provisional application No. 63/311,130, filed on Feb. 17, 2022, provisional application No. 63/310,853, filed on Feb. 16, 2022.

(51) Int. Cl.
*A61K 31/57* (2006.01)

(52) U.S. Cl.
CPC .................................... *A61K 31/57* (2013.01)

(58) Field of Classification Search
CPC ...................................................... A61K 31/57
See application file for complete search history.

(56) References Cited

U.S. PATENT DOCUMENTS 5,028,600 A 7/1991 Jeppsson ........................ 514/182
6,824,791 B2 11/2004 Mathiowitz ................... 424/458
8,697,678 B2 4/2014 Goodchild .................... 514/178
8,975,245 B2 3/2015 Goodchild ............. A61K 47/40
9,757,391 B2 9/2017 Goodchild ........... A61K 31/573
10,251,894 B2 4/2019 Rogawski .............. A61K 31/57
10,322,139 B2 6/2019 Reddy .................... A61K 31/57
10,478,505 B2 11/2019 Rogawski .............. A61K 47/46
10,639,317 B2 5/2020 Cashman ............. A61K 31/573
11,000,531 B2 5/2021 Cashman ............. A61K 31/573
11,337,987 B1 5/2022 Patel ...................... A61K 31/57
2005/0096296 A1 5/2005 Fikstad ........................... 514/58
2005/0119340 A1 6/2005 Anderson ...................... 514/535
2007/0112017 A1 5/2007 Barlow ......................... 514/282
2011/0312928 A1* 12/2011 Nachaegari ............. A61P 35/00 514/177
2012/0282335 A1 11/2012 Venkatesh ..................... 424/465
2016/0030583 A1 2/2016 Fikstad .................. A61K 47/44
2018/0021349 A1* 1/2018 Dhingra ............... A61K 9/4858 514/181
2018/0071315 A1* 3/2018 Cashman .............. A61K 47/32
2018/0099053 A1 4/2018 Fikstad .................. A61K 47/44
2019/0008873 A1* 1/2019 Salituro .............. C08B 37/0015
2019/0160078 A1 5/2019 Masuoka ............ A61K 31/565
2019/0351019 A1 11/2019 Cooper ................ A61K 38/191
2020/0069805 A1 3/2020 Fikstad .................. A61K 47/44

FOREIGN PATENT DOCUMENTS

WO WO2005041929 5/2005 ............... A61K 9/00
WO WO2006119498 11/2006 ............... A61K 9/22
WO WO-2016040322 A1 * 3/2016 ............ A61K 31/56

OTHER PUBLICATIONS

Torbjörn Bäckström, Göran Wahlström, Kerstin Wahlström, Di Zhu, Ming-De Wang, Isoallopregnanolone; an antagonist to the anaesthetic effect of allopregnanolone in male rats, European Journal of Pharmacology, vol. 512, Issue 1, 2005, pp. 15-21, ISSN 0014-2999, (Year: 2005).*

Progestin. (n.d.) The American Heritage® Medical Dictionary. (2007). Retrieved Jun. 17, 2022 from https://medical-dictionary.thefreedictionary.com/progestin (Year: 2007).*

Peeler et al. Oral versus Intravenous Sedation Study Group. Patient Satisfaction with Oral versus Intravenous Sedation for Cataract Surgery: A Randomized Clinical Trial. Ophthalmology. Sep. 2019;126(9):1212-1218. (Year: 2019).*

Bell Harbour Dental. Oral Sedation vs. IV Sedation: What is the Better Option for Me? Published Dec. 14, 2018. Retrieved from the internet on Aug. 22, 2022, https://bellharbourdental.com/oral-sedation/oral-sedation-vs-iv-sedation/ (Year: 2018).*

PubChem. Pregnanolone. Retrieved from the Internet on Sep. 8, 2023, https://pubchem.ncbi.nlm.nih.gov/compound/31402#section=Wikidata. (Year: 2023).*

Davis tet al. Measuring Samples Per USP 26 Using Shimadzu TOC-V*W. Shimadzu. Retrieved from the internet on Sep. 8, 2023, https://www.shimadzu.com/an/sites/shimadzu.com.an/files/pim/pim_document_file/applications/application_note/12019/usp26withtoc-wv.pdf (Year: 2023).*

Boateng L, Ansong R, Owusu WB, Steiner-Asiedu M. Coconut oil and palm oil's role in nutrition, health and national development: A review. Ghana Med J. Sep. 2016;50(3):189-196. (Year: 2016).*

(Continued)

*Primary Examiner* — Lauren Wells
(74) *Attorney, Agent, or Firm* — Michael R. Schramm

(57) ABSTRACT

Disclosed are methods and oral compositions for treating CNS disorders. An embodiment of the invention comprises orally administering a 3α-OH-5β-pregnan-20-one containing composition to a subject having a CNS disorder. The composition preferably exhibits a fast release rate of the 3α-OH-5β-pregnan-20-one. The current compositions may provide desired serum levels of 3α-OH-5β-pregnan-20-one to effectively treat CNS disorders. The oral compositions and methods disclosed herein may be administered to a subject in need of CNS disorder therapy, to deliver therapeutically effective amounts of 3α-OH-5β-pregnan-20-one for treating CNS disorders.

12 Claims, 3 Drawing Sheets

(56) References Cited

OTHER PUBLICATIONS

Cassiday, L. Emuslions: making oil and water mix. AOCS. Retrieved from the Internet on Sep. 8, 2023, https://www.aocs.org/stay-informed/inform-magazine/featured-articles/emulsions-making-oil-and-water-mix-april-2014?SSO=True#:~:text=Surfactant%20is%20the%20broadest%20term,a%20liquid%20and%20a%20solid (Year: 2023).*

Liang JJ, Rasmusson AM. Overview of the Molecular Steps in Steroidogenesis of the GABAergic Neurosteroids Allopregnanolone and Pregnanolone. Chronic Stress (Thousand Oaks). Dec. 19, 2018 (Year: 2018).*

Vandana et al. An overview on in situ micronization technique—An emerging novel concept in advanced drug delivery. Saudi Pharmaceutical Journal, Published 2014. (Year: 2014).*

Lee JH, Yeo Y. Controlled Drug Release from Pharmaceutical Nanocarriers. Chem Eng Sci. Mar. 24, 2015;125:75-84. (Year: 2015).*

Markl D, Zeitler JA. A Review of Disintegration Mechanisms and Measurement Techniques. Pharm Res. May 2017;34(5):890-917. (Year: 2017).*

Anderson. What does Micronized mean? Drugs.com. Retrieved from the Internet on Sep. 13, 2023, https://www.drugs.com/ medical-answers/micronized-mean-3570285/ (Year: 2023).*

Arne Wessen et al., Concentration-Effect Relationships of Eltanolone Given as a Bolus Dose or Constant Rate Intravenous Infusion to Healthy Male Volunteers, Jun. 1996, vol. 84, No. 6, pp. 1317-1326.

Bitran et al., Anxiolytic effects of the neuroactive steroid pregnanolone (3a-OH-5(1-pregnan-20-one) after microinjection in the dorsal hippocampus and lateral septum, Brain Research, vol. 850, lss. 1-2. Dec. 11, 1999, pp. 217-224.

Carvalho, USP-NF And U.S. Pharmacist Featuring Proprietary PCCA Bases, PCCA, Apr. 21, 2021, pp. 1-3.

Siewert, FIP Guidelines for Dissolution Testing of Solid Oral Products, ECA Academy, Sep. 22, 2017, pp. 1-14.

* cited by examiner

3α-OH-5β-PREGNAN-20-ONE COMPOSITIONS AND METHODS FOR TREATING CENTRAL NERVOUS SYSTEM DISORDERS

CROSS REFERENCE TO RELATED APPLICATIONS

This nonprovisional utility patent application claims the benefit under 35 USC § 119(e) of US provisional application nos. 63/310,853 filed Feb. 16, 2022 and 63/311,130 filed Feb. 17, 2022, all of which are expressly incorporated herein in their entirety by this reference.

FIELD OF THE INVENTION

The present disclosure relates to oral compositions, dosage forms and regimens, and methods of treating a subject with a central nervous system disorder. Accordingly, this disclosure involves the fields of chemistry, pharmaceutical sciences, medicine, and other health sciences.

BACKGROUND OF THE INVENTION

Central nervous system (CNS) disorders are neurological disorders that may affect the structure or function of the brain or spinal cord. CNS disorders may have various causes including trauma, infections, degeneration, structural defects, tumors, autoimmune disorders, and strokes. Some examples include addiction, attention deficit/hyperactivity disorder (ADHD), autism, epilepsy, multiple sclerosis, depression, anxiety, and the like. A wide range of treatments have been tried for CNS disorders ranging from surgery to neural rehabilitation to prescription medication. For example, depression is a mood disorder that causes a persistent feeling of sadness and loss of interest. Also called major depressive disorder or clinical depression, depression affects how a person feels, thinks, and behaves and may lead to a variety of emotional and physical problems.

Neuroactive steroids represent a class of endogenous steroids that in the brain, the adrenals, and the gonads, have potent and selective effects on GABAA receptors that consist of synaptic and extrasynaptic subunits. When neuroactive steroids activate synaptic GABAA receptors, the activation generates rapid, short chloride ion currents, called phasic inhibition. When neuroactive steroids activate extrasynaptic GABAA receptors, the activation generates gradual, constant chloride ion currents, called tonic inhibition.

3α-OH-5β-pregnan-20-one, having the chemical structure as shown in FIG. 1, is characterized with a hydrogen at the beta position at C5 of the first carbon ring, unlike 3α-OH-5α-pregnan-20-one which has a hydrogen at the alpha position at C5. The binding efficiency of 3α-OH-5β-pregnan-20-one to extrasynaptic GABAA receptors (see: article PMC3399243 on the NCBI's website) was reported as about four times higher than 3α-OH-5α-pregnan-20-one (Ref. Nik et al, Mol Pharmacol 2017). Another distinction is that binding of 3α-OH-5β-pregnan-20-one to GABAA receptor is reported as about 10 times more potent on extrasynaptic GABAA receptors as compared to a synthetic positive allosteric neuroactive steroid, e.g., ZURANOLONE (see: ZURANOLONE on Wikipedia's website). Also, the potency of 3α-OH-5β-pregnan-20-one to synaptic GABAA receptor is about 3 times higher on a synaptic subunit (alβ3γ2) and about 7 times higher on an extrasynaptic subunit (α4β3δ) as compared to GANAXOLONE (see: GANAXOLONE on Wikipedia's website).

3α-OH-5β-pregnan-20-one has low water solubility and high lipophilicity. The elimination half-life of 3α-OH-5β-pregnan-20-one delivered by intravenous atrial injection was reported to be between 0.9 and 3.5 hours. 3α-OH-5β-pregnan-20-one has a melting point of ~150° C. Therefore, desired therapeutic serum levels post oral administration have remained elusive possibly due to inadequate release or solubilization in the gastrointestinal tract.

There is presently no acceptable approach to allow an oral dosage form comprising 3α-OH-5β-pregnan-20-one to provide therapeutically effective levels of 3α-OH-5β-pregnan-20-one for treatment of CNS disorders or to patients with other disorders in need of 3α-OH-5β-pregnan-20-one. Although often synthetic chemical modification from endogenous neuroactive steroids is employed to improve oral bioavailability such as ZURANOLONE, ETX-155 (see: ETX-155 on Eliem Therapeutic's website), GANAXOLONE, PRAX-114 (see: PRAX-114 on Wikipedia's website), ALPHAXALONE on Wikipedia's website), etc., their unknown safety profiles need to be clarified or studied for potential therapeutic use.

Thus there remains an unmet need for safe and adequate orally bioavailable compositions and methods comprising 3α-OH-5β-pregnan-20-one to treat patients in need of 3α-OH-5β-pregnan-20-one therapy. Further in particular, there remains gender-specific unmet needs. For instance, there remains a need for safe and adequately orally bioavailable compositions and methods and treatments comprising 3α-OH-5β-pregnan-20-one for women (during preconception, pregnancy, delivery/labor, post-partum, or perimenopause and menopause) with epilepsy.

SUMMARY OF THE INVENTION

The present disclosure encompasses compositions and oral dosage forms and regimens including 3α-OH-5β-pregnan-20-one and related methods. The compositions and oral dosage forms may be formulated to include a therapeutically effective amount of 3α-OH-5β-pregnan-20-one and plurality of pharmaceutically acceptable additives. In one aspect, the pharmaceutically acceptable additive of the composition or dosage form may provide 3α-OH-5β-pregnan-20-one in an amount sufficient to treat a CNS disorder when orally administered to a subject. In another aspect, the composition or dosage form may include fast releasing or dissolving or solubilized forms of 3α-OH-5β-pregnan-20-one that may enhance, increase, or maximize bioavailability (e.g. $C_{max}$ and/or AUC) of 3α-OH-5β-pregnan-20-one when orally administered to a subject. For example, in one aspect, in vitro release, in vivo solubilization, absorption and/or CNS activity of 3α-OH-5β-pregnan-20-one, when orally administered to a subject through compositions and methods of this invention, is increased. In another aspect, the absorption and/or CNS activity of 3α-OH-5β-pregnan-20-one, when orally administered to a subject through compositions and methods of this invention, is relatively increased as compared to a composition comprising an equivalent amount of 3α-OH-5β-pregnan-20-one utilizing untreated crystalline forms of 3α-OH-5β-pregnan-20-one or cyclodextrin solution compositions when orally administered the subject.

In one embodiment, the composition may be formulated as an oral dosage form that has from about 10 mg to about 600 mg of 3α-OH-5β-pregnan-20-one. 3α-OH-5β-pregnan-20-one may be treated, which results in grinded, sieved, milled, micronized, or nanosized forms before formulating in an oral composition or dosage form, or amorphous or fully solubilized forms post formulating in the composition or dosage form. A crystalline form of said treated 3α-OH-5β-pregnan-20-one comprises a particle size distribution of at least one of a D90 of less than 75 μm, a D10 of greater than 1 μm, and a D50 of at least one of 0.15 μm to 50 μm, 30 μm to 50 μm, 0.3 to 30 μm, and 2 μm to 8 μm.

In one embodiment, the dose amount of the composition comprises from about 10 mg to about 1200 mg of 3α-OH-5β-pregnan-20-one. In one aspect, the composition may be a solid, liquid, a semi-liquid or semi solid, gel, a granule, a pellet, a powder, a syrup, an emulsion, a dispersion, a suspension, a capsule, a sprinkle, a tablet, a chew, a cream, an ointment, a paste, a paste-like composition, or a drink.

In yet another embodiment, a method of treating a CNS disorder in a subject may include orally administering a therapeutically effective amount of 3α-OH-5β-pregnan-20-one to the subject. In one aspect, the therapeutically effective amount of 3α-OH-5β-pregnan-20-one may be an amount of 3α-OH-5β-pregnan-20-one that is sufficient to treat the CNS disorder. In another aspect, the compositions comprising 3α-OH-5β-pregnan-20-one disclosed herein may be in a form that provides a therapeutically effective amount of 3α-OH-5β-pregnan-20-one for treating the CNS disorder in the subject. In yet another aspect, the 3α-OH-5β-pregnan-20-one may be combined with a plurality of additives comprising at least one lipophilic additive that is sufficient to provide a therapeutically effective amount of 3α-OH-5β-pregnan-20-one for treating the CNS disorder in the subject.

BRIEF DESCRIPTION OF THE DRAWINGS

Features and advantages of the various embodiments will be apparent from the detailed description which follows, taken in conjunction with the accompanying drawings, which together illustrate, by way of example, features of the disclosure; and, wherein.

DETAILED DESCRIPTION OF THE INVENTION

Figure 1:
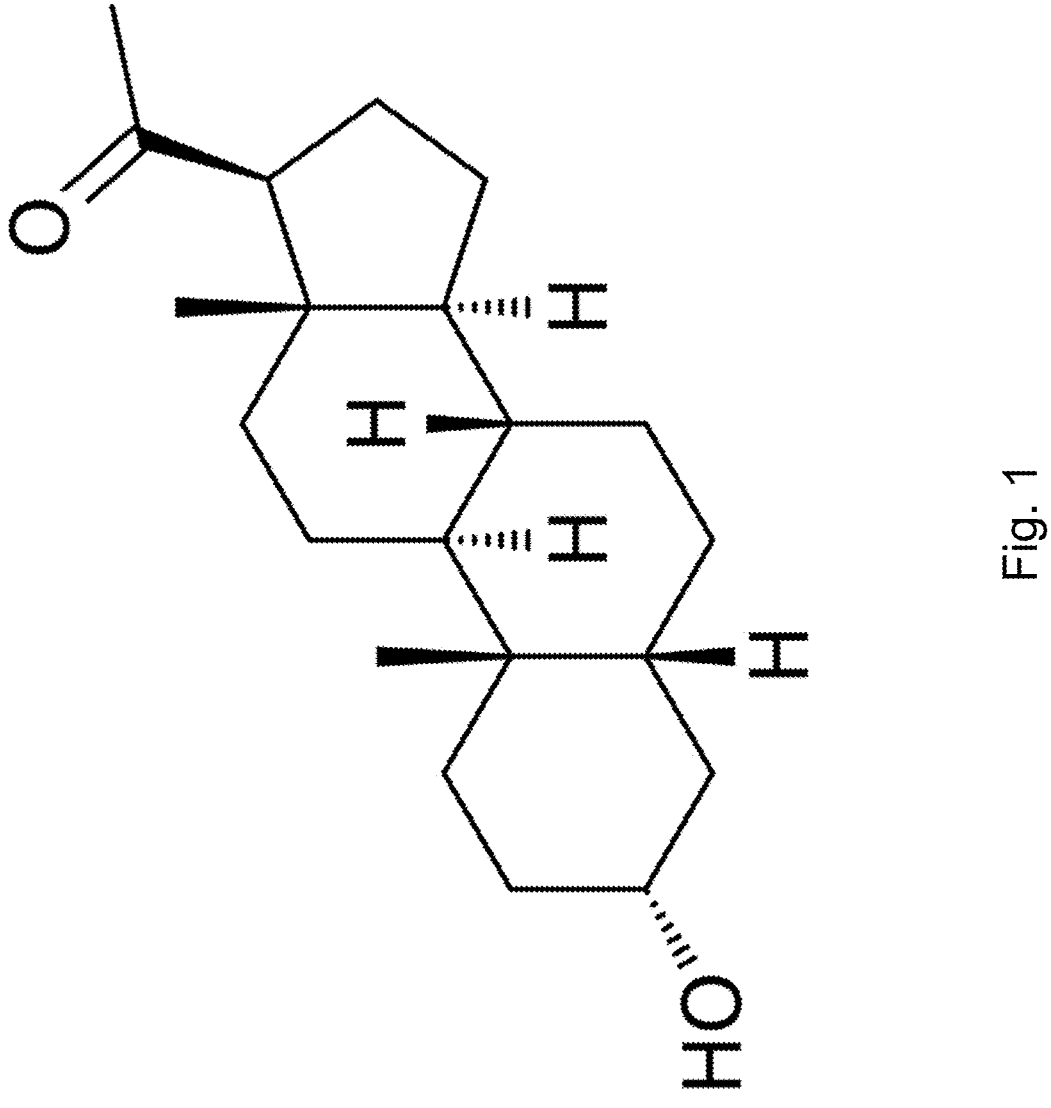
FIG. 1 is an illustration of chemical structure of 3α-OH-5β-pregnan-20-one.

Before invention embodiments are described, it is to be understood that this disclosure is not limited to the particular structures, process steps, or materials disclosed herein, but is extended to equivalents thereof as would be recognized by those ordinarily skilled in the relevant arts. It should also be understood that terminology employed herein is used for the purpose of describing particular examples or embodiments only and is not intended to be limiting.

Furthermore, the described features, structures, or characteristics may be combined in any suitable manner in one or more embodiments. In the following description, numerous specific details are provided, such as examples of compositions, dosage forms, treatments, etc., to provide a thorough understanding of various invention embodiments. One skilled in the relevant art will recognize, however, that such detailed embodiments do not limit the overall inventive concepts articulated herein but are merely representative thereof.

Definitions

It should be noted that, the singular forms "a," "an," and, "the" include plural referents unless the context clearly dictates otherwise. Thus, for example, reference to "an excipient" includes reference to one or more of such excipients, and reference to "the additive" includes reference to one or more of such additives.

As used herein, the terms "treat," "treatment," or "treating" and the like refers to administration of a therapeutic agent to a subject who is either asymptomatic or symptomatic. In other words, "treat," "treatment," or "treating" may refer to the act of reducing or eliminating a condition (i.e., symptoms manifested), or it may refer to prophylactic treatment (i.e., administering to a subject not manifesting symptoms in order to prevent their occurrence). Such prophylactic treatment may also be referred to as prevention of the condition, preventative action, preventative measures, and the like.

As used herein, the terms "therapeutic agent," "active agent," and the like may be used interchangeably and refer to an agent or substance that has measurable specified or selected physiologic activity when administered to a subject in a significant or effective amount. It is to be understood that the term "drug" is expressly encompassed by the present definition as many drugs and prodrugs are known to have specific physiologic activities. These terms of art are well-known in the pharmaceutical and medicinal arts. Further, when these terms are used, or when a particular active agent is specifically identified by name or category in this written description, it is understood that such recitation is intended to include express support for the active agent per se, as well as pharmaceutically acceptable salts, esters or compounds significantly related thereto, including without limitation, prodrugs, active metabolites, isomers, and the like. For example, recitation of the active agent 3α-OH-5β-pregnan-20-one also includes express support for the active metabolites.

As used herein, the terms "formulation" and "composition" are used interchangeably and refer to a mixture of two or more compounds, elements, or molecules. In some aspects, the terms "formulation" and "composition" may be used to refer to a mixture of one or more active agents with additives or other excipients. Furthermore, the term "dosage form" may include one or more formulation(s) or composition(s) provided in a format for administration to a subject.

As used herein, the terms "pharmaceutically acceptable additive" or "additive" are used interchangeably and refer to a pharmaceutically acceptable agent or ingredient that may be combined with an active agent as part of a composition or dosage form. In some aspects, pharmaceutically acceptable additives may impact the form or behavior of an active agent. For example, in some aspects, a pharmaceutically acceptable additive may be capable of fully or partially releasing/dissolving or solubilizing 3α-OH-5β-pregnan-20-one in a pharmaceutical composition or enabling a noncrystalline (solubilized or amorphous) form of the active agent. In another aspects, a pharmaceutically acceptable additive may be capable of fully or partially releasing/dissolving or solubilizing 3α-OH-5β-pregnan-20-one in a pharmaceutical composition or enabling a crystalline form of the active agent as starting material. In one aspect, a composition, wherein said 3α-OH-5β-pregnan-20-one comprises at least one form of substantially solubilized, partially solubilized, crystalline, partially crystalline, substantially noncrystalline, amorphous solid, a solid dispersion, a solid solution, and a eutectic mixture.

Further, in some aspects, the additive may impact or control the properties and performance of the composition or dosage form. For example, in some aspects, an additive may impact or control the pharmacokinetic performance or profile (e.g. release rate and/or extent of release of the active agent) of the composition and/or the dosage form.

As used herein, the terms a "semi-liquid" or "semi-solid" active agent corresponds to a partially solubilized active agent and a "liquid" active agent corresponds to a fully solubilized active agent at room temperature.

As used herein, the term a "subject" refers to a mammal that may benefit from the administration of a drug composition, dosage form or dosage regiment, or method disclosed herein. Examples of subjects include humans, and may also include other animals such as horses, pigs, cattle, dogs, cats, rabbits, and aquatic mammals. In one specific aspect, a subject is a human. In another aspect, the subject is a female. In another aspect, the subject is a female of childbearing age. In another aspect the female has delivered a baby within the last 1-12 months. In another aspect, the subject is male.

As used herein, the term "in need of treatment" and the like refers to a subject that has a disease, condition, or disorder or is suspected of having the disease, condition, or disorder according to various diagnostic criteria typically used in practice, or desires treatment or is indicated for treatment. Thus, "in need of treatment" may include the operation of identifying a subject in need of treatment.

As used herein, the term "identifying a subject in need of treatment" may include the operation of obtaining a biological sample from the subject and determining the level of one or more biomarkers as described herein, assessing a biological sample obtained from said subject, performing an imaging analysis on the subject, assessing one or more clinical characteristics of said subject (e.g., assessing symptoms or overt symptoms), or a combination thereof.

As used herein, the terms "illness," "disease," "condition," "symptom", and "disorder" may be used interchangeably and refer to an abnormality or incorrect functioning of any part, group, or system of a subject's physiology regardless of the causality thereof. For example, a mental illness or emotional disorder may be caused by environmental factors, genetic factors, physiologic events, past experiences, and other influences or combinations thereof.

As used herein, the term an "acute" condition refers to a condition that may develop rapidly and have distinct symptoms needing urgent or semi-urgent care. By contrast, a "chronic" condition refers to a condition that is typically slower to develop and lingers or otherwise progresses over time. Some examples of acute conditions may include without limitation, an asthma attack, bronchitis, a heart attack, pneumonia, and the like. Some examples of chronic conditions may include without limitation, arthritis, diabetes, hypertension, dyslipidemia, and the like.

The terms "serum levels," "serum amounts", "serum concentrations," "plasma levels," "plasma concentrations," "blood levels," and "blood concentrations" and the like may be used interchangeably herein and refer to the total amount of an identified analyte (e.g. identified metabolite or active agent), including free, bioavailable, and bound fractions in a subject's blood. For example, "serum 3α-OH-5β-pregnan-20-one" or "serum 3α-OH-5β-pregnan-20-one levels" or "serum 3α-OH-5β-pregnan-20-one concentration" or "plasma 3α-OH-5β-pregnan-20-one concentration" or "3α-OH-5β-pregnan-20-one concentration in the blood" refer the total 3α-OH-5β-pregnan-20-one concentration which is the sum of the 3α-OH-5β-pregnan-20-one fractions present including substantially free and bound 3α-OH-5β-pregnan-20-one concentrations. It should be understood that in this written description, such terms provide express support for total analyte or agent levels, as well as for the various applicable fractions thereof, including bioavailable, bound, and substantially free fractions. Unless otherwise specified, these values are "observed" concentrations or amounts without adjusting or correcting for the base-line serum levels in the subject(s). As with any bio-analytical measure, for increased consistency, the method employed to measure initial serum levels should be consistent with the method used to monitor and re-measure serum levels during clinical testing and therapy for a subject. As used herein, the term "$C_{avg}$" refers to an average serum concentration level for time 0 to t (e.g. average daily serum concentration level, daily $C_{avg}$, is calculated as ratio of $AUC_{0-24}$/24 hours) and the term "$C_{max}$" refers to a maximum serum concentration level post single dose administration for the period.

Serum 3α-OH-5β-pregnan-20-one and its isomer measurements based on an immunoassay are not accurate using a typical radioimmunoassay method (RIA) because the RIA assay is typically not very specific to the target analyte. To measure the target analyte accurately, the assay needs to be based on chromatography-combined mass spectrometry method (LC-MS, LC-MS/MS, or GC-MS), which may provide reliable PK data to assess the true PK and pharmacodynamic (PD) potential of 3α-OH-5β-pregnan-20-one. Consequently, data and results related to oral compositions of 3α-OH-5β-pregnan-20-one and its neuro-steroid metabolites are only reliable with respect to levels of neuroactive steroid or the adequacy of neuroactive steroid levels for desirable GABAA receptor modulation when determined by analytical procedures that are amenable to the individual analyte separation step for specificity and accuracy, such as for liquid or gas chromatography, liquid chromatography-tandem mass spectrometry, or gas chromatography-mass spectrometry (LC-MS, LC-MS/MS, or GC-MS).

In one aspect, the PK values (e.g. serum concentrations, computed ratios) of an analyte of interest (e.g. 3α-OH-5β-pregnan-20-one), derived from the compositions and methods disclosed herein, are based on LC-MS, LC-MS/MS or GC-MS measurements.

As use herein with respect to physiologic levels of a given substance, the term "baseline" refers to a level or concentration of the substance, such as analyte of interest (e.g. 3α-OH-5β-pregnan-20-one), in a subject prior to administration of an active agent. For example, the baseline level of 3α-OH-5β-pregnan-20-one in a subject would the subject's 3α-OH-5β-pregnan-20-one serum level prior (e.g., just prior) to the commencement of 3α-OH-5β-pregnan-20-one administration or therapy.

The term "oral administration" represents any method of administration in which an active agent may be administered by swallowing, chewing, sucking, or drinking of the composition or dosage form. Oral administration may be intended for enteral delivery of an active agent or transmucosal delivery of the active agent. In some embodiments, the composition and dosage forms of the current disclosure may be admixed with food or drink prior to being orally consumed or may be otherwise co-administered with food or a meal.

As used herein, the terms "release" and "release rate" are used interchangeably to refer to the discharge or liberation of a substance, including without limitation a drug, from the composition or dosage form into a surrounding environment such as an aqueous medium either in vitro or in vivo. In another aspect, the term "disintegration" is a physical process related to the mechanical breakdown of a tablet into smaller particles/granules, representing the breakage of inter-particle interactions generated during formation of a tablet by compaction of granulated particles of the active pharmaceutical ingredient (API) and excipients according to <701> Disintegration, USP 43. In another aspect, the term "disintegration" is a physical process related to the opening or rupturing of a capsule. As used herein, the term "disintegration time" refers to an amount of time required to elapse in order for disintegration to occur.

As used herein, the term "dissolution" refers to solubilization of the active agent in the composition or dosage form into a surrounding environment such as an aqueous medium either in vitro or in vivo.

In some aspects of the present invention, the release of the drug may be controlled release. As used herein, the term "controlled release" represents the release of the drug from the dosage form according to a predetermined profile. In some aspects, the controlled release selected may be, accelerated, intermediate, delayed, extended, sustained, pulsatile, gastric, enteric or colonic. Accelerated released may be obtained by for instance an increased rate of release of the drug, an increased susceptibility to metabolism in the Gastro-intestinal (GI) tract, and combinations thereof. In another aspect, combinations of the aforementioned release profiles may be used in order to achieve specific delivery results, such as an immediate release followed by a delayed and/or a sustained release of the active agent.

As used herein, the terms a "dosing regimen" or "regimen" such as an "initial dosing regimen" or "starting dose" or a "maintenance dosing regimen" refers to how, when, how much, and for how long a dose of the compositions or dosage forms of the present disclosure may be administered to a subject. For example, an initial or starting dose regimen for a subject may provide for a total daily dose of from about 15 mg to about 1500 mg administered in two divided doses at least 12 hours apart (e.g., once with breakfast and once with dinner) with meals repeated daily for 30 days.

As used herein, the term "daily dose" refers to the amount of 3α-OH-5β-pregnan-20-one administered to a subject over a 24-hour period of time. The daily dose may be administered one or more administrations during the 24-hour period. In one embodiment, the daily dose provides for two or three or four or six or eight administrations in a 24-hour period. With this in mind, an "initial dose" or initial daily dose" refers to a dose administered during the initial regimen or period of a dosing regimen.

As used herein, the terms an "effective amount" or a "therapeutically effective amount" of a drug refers to a non-toxic, but sufficient amount of the drug, to achieve therapeutic results in treating a condition for which the drug is known to be effective. It is understood that various biological factors may affect the ability of a substance to perform its intended task. Therefore, an "effective amount" or a "therapeutically effective amount" may be dependent in some instances on such biological factors. Further, while the achievement of therapeutic effects may be measured by a physician or by other qualified medical personnel using evaluations known in the art, it is recognized that individual variation and response to treatments may make the achievement of therapeutic effects a somewhat subjective decision. The determination of an effective amount is well within the ordinary skill in the art of pharmaceutical sciences and medicine. See, for example, Meiner and Tonascia, "Clinical Trials: Design, Conduct, and Analysis," *Monographs in Epidemiology and Biostatistics*, Vol. 8 (1986), incorporated herein by reference.

As used herein the term a "single unit" when used to describe dosing to a subject refers to the dosage form being a single dosage form, e.g. a single tablet, capsule, pump or squirt of gel or solution (1 ml), etc. In contrast, "multiple unit" when used to describe dosing of a subject refers to the dosage including two or more dosage forms, e.g. 2 capsules, 3 tablets, 2-4 pumps or squirts, etc. It is noteworthy that multiple unit dosage forms generally will be the same type of dosage forms (i.e. tablet or capsule) but are not required to be the same dosage form type.

In this disclosure, "comprises," "comprising," "containing" and "having" and the like may have the meaning ascribed to them in U.S. Patent law and may mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "consisting essentially of" or "consists essentially of" or "essentially consisting" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open-ended term, like "comprising" or "including," in this written description it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

Occurrences of the phrase "in one embodiment," or "in one aspect," herein do not necessarily all refer to the same embodiment or aspect.

As used herein, comparative terms such as "increased," "decreased," "better," "worse," "higher," "lower," "enhanced," "improved," "maximized," "minimized," and the like refer to a property of a device, component, composition, biologic response, biologic status, or activity that is measurably different from other devices, components, compositions, biologic responses, biologic status, or activities that are in a surrounding or adjacent area, that are similarly situated, that are in a single device or composition or in multiple comparable devices or compositions, that are in a group or class, that are in multiple groups or classes, or as compared to an original (e.g. untreated) or baseline state, or the known state of the art. For example, a composition or dosage form comprising 3α-OH-5β-pregnan-20-one that "increases" 3α-OH-5β-pregnan-20-one serum levels or provides a 3α-OH-5β-pregnan-20-one in a subject that is elevated as compared to a serum level at a previous point in time, such as a baseline level (e.g., prior to treatment), or as compared to an earlier treatment with a different dose (e.g., lower dose). Alternatively, a composition or dosage form that provides an "increased" serum level of 3α-OH-5β-pregnan-20-one may provide such increase as compared to an alternative known composition or dosage form e.g. compared to an equivalent amount of 3α-OH-5β-pregnan-20-one utilizing a sub optimal additive or compositions comprising crystalline 3α-OH-5β-pregnan-20-one or compositions consisting essentially of 3α-OH-5β-pregnan-20-one suspended/dissolved in edible oil such as canola oil or peanut oil or medium chain triglyceride, or compositions consisting essentially of 3α-OH-5β-pregnan-20-one solubilized/dissolved 3α-OH-5β-pregnan-20-one in cyclodextrin solution or compositions consisting essentially of 3α-OH-5β-pregnan-20-one suspended in TWEEN-80 when orally administered the subject.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "fully" refers to the complete extent or degree of an action, characteristic, property, state, structure, item, or result.

As used herein, the term "about" is used to provide flexibility to a numerical range endpoint by providing that a given value may be "a little above" or "a little below" the endpoint. Unless otherwise stated, use of the term "about" in accordance with a specific number or numerical range should also be understood to provide support for such numerical terms or range without the term "about". For example, for the sake of convenience and brevity, a numerical range of "about 50 angstroms to about 80 angstroms" should also be understood to provide support for the range of "50 angstroms to 80 angstroms." Furthermore, it is to be understood that in this specification support for actual numerical values is provided even when the term "about" is used therewith. For example, the recitation of "about" 30 should be construed as not only providing support for values a little above and a little below 30, but also for the actual numerical value of 30 as well.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the term "GABA" refers to gamma aminobutyric acid (see: gamma aminobutyric acid and GABA on Wikipedia's website).

Concentrations, amounts, levels and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges or decimal units encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range, or the characteristics being described.

Reference throughout this specification to "an example" means that a particular feature, structure, or characteristic described in connection with the example is included in at least one embodiment. Thus, appearances of the phrases "in an example" in various places throughout this specification are not necessarily all referring to the same embodiment.

DESCRIPTION

Reference will now be made in detail to preferred invention embodiments. While the embodiments will be described with particularity, the present disclosure is not limited to such embodiments. To the contrary, it is intended to cover alternatives, variants, modifications, and equivalents as may be included within the spirit and scope of the disclosure.

An initial overview of technology embodiments is provided below, and then specific technology embodiments are described in further detail later. This initial summary is intended to aid readers in understanding the technology more quickly but is not intended to identify key features or essential features of the technology nor is it intended to limit the scope of the claimed subject matter.

Some of the neuro-modulatory and protective effects of 3α-OH-5β-pregnan-20-one may produce anticonvulsant, antidepressant, anxiolytic, and neuroprotective effects in experimental animals as well as in tissues and cell cultures.

Thus, there remains an unmet need for oral compositions and methods that enable generation of higher, faster, more reliable, and adequate serum levels of 3α-OH-5β-pregnan-20-one for treating various CNS disorders whereby desirable release and subsequent effective absorption of 3α-OH-5β-pregnan-20-one is enabled for treating subjects in need of 3α-OH-5β-pregnan-20-one for treating CNS disorders. In some aspects, we have surprisingly found oral compositions and methods that may produce desirable levels of 3α-OH-5β-pregnan-20-one.

In some aspects, the compositions for oral administration and methods disclosed herein are intended to treat a CNS disorder comprising at least one of sleep disorders (e.g., insomnia), mood disorders (e.g., depression such as PND, major depressive disorder, postpartum depression (PPD), essential tremor, treatment resistant depression, or perinatal depression, antepartum anxiety and/or depression in women of childbearing age with or without active epilepsy), anhedonia, dysthymic disorder (e.g., mild depression), bipolar disorder (e.g., I and/or II), anxiety disorders (e.g., generalized anxiety disorder (GAD), social anxiety disorder), stress, post-traumatic stress disorder (PTSD), compulsive disorders (e.g., obsessive compulsive disorder (OCD)), schizophrenia spectrum disorders (e.g., schizophrenia, schizoaffective disorder), convulsive disorders (e.g., epilepsy, absence seizures, status epilepticus (SE)), seizures, acute respective seizures, catamenial epilepsy), disorders of memory and/or cognition (e.g., attention disorders, attention deficit hyperactivity disorder (ADHD)), dementia (e.g., Alzheimer's type dementia, Lewis body type dementia, vascular type dementia), movement disorders (e.g., Huntington's disease, Parkinson's disease), personality disorders (e.g., anti-social personality disorder, obsessive compulsive personality disorder), autism spectrum disorders (ASD) (e.g., autism, monogenetic causes of autism such as synaptopathy (see: synaptopathy on Wikipedia's website), Rett syndrome, Fragile X syndrome, Angelman syndrome), pain (e.g., neuropathic pain, injury related pain syndromes, acute pain, chronic pain), traumatic brain injury (TBI), vascular diseases (e.g., stroke, ischemia, vascular malformations), substance abuse disorders and/or withdrawal syndromes (e.g., addition to opiates, cocaine, and/or alcohol), and tinnitus.

In one aspect, the oral compositions and methods disclosed herein are formulated to treat a CNS disorder comprising depression. For example, depression may comprise major depressive disorder, persistent depressive disorder (e.g. dysthymia), PPD, ante partum depression, essential tremor, treatment resistant depression, bipolar disorder (e.g. manic-depressive disorder), and seasonal affective disorder (SAD).

In one aspect, the oral compositions and methods disclosed herein are designed to treat CNS disorders (e.g. suicide ideation, depression, anxiety) in epileptic women of childbearing age, manage epilepsy during menses, manage epilepsy in pregnancy, manage epilepsy peripartum and postpartum, or manage epilepsy in post or peri menopausal women.

In one embodiment, 3α-OH-5β-pregnan-20-one compositions and oral dosage forms may be formulated to provide amounts or peak levels of 3α-OH-5β-pregnan-20-one that are therapeutically effective for treating a CNS disorder when orally administered to a subject. For example, in one aspect, the compositions and oral dosage forms may include a plurality of pharmaceutically acceptable additives that provide serum 3α-OH-5β-pregnan-20-one levels in an amount sufficient to treat a CNS disorder when orally administered to a subject.

In one aspect, the analyte serum levels are measured using a LC-MS, LC-MS/MS or GC-MS bioanalytical method.

In another embodiment, in comparison to an AUC obtained from IV infusion having an equivalent dose of a 3α-OH-5β-pregnan-20-one administered over the course of 4 hours (IV AUC), an oral administration of a unit dosage form comprising a 3α-OH-5β-pregnan-20-one composition to a subject results in an AUC amount that comprises at least one of the following percentages of an IV AUC: 3%, 4%, 5%, 6%, 7%, 8%, 9%, 10%, 11%, 12%, 13%, 14%, and 15%.

In one embodiment, the invention is an oral pharmaceutical composition comprising 3α-OH-5β-pregnan-20-one and a plurality of additives, wherein oral administration of the composition to a subject having at least one of a neuropsychiatric and neurodegenerative disorder results in a serum level of said 3α-OH-5β-pregnan-20-one in the subject such that at least one of the neuropsychiatric and the neurodegenerative disorder is substantially reduced, improved, or eliminated.

In one embodiment, the invention is an oral pharmaceutical composition comprising: a fast releasing form of 3α-OH-5β-pregnan-20-one and a plurality of pharmaceutically acceptable additives, wherein when the composition is orally administered to a subject, the composition provides an increase of 3α-OH-5β-pregnan-20-one levels in the subject, as compared to a 3α-OH-5β-pregnan-20-one level provided by the compositions comprising an equivalent amount of 3α-OH-5β-pregnan-20-one but being devoid of a solubilizer and/or dispersant.

In another embodiment, the disclosed oral pharmaceutical composition comprises a fast releasing form of 3α-OH-5β-pregnan-20-one and a plurality of pharmaceutically acceptable additives. When the composition is administered with a meal, the composition provides a serum level that is greater than a serum level resulting from a comparable cyclodextrin solution administration. In yet further embodiment, the disclosed oral pharmaceutical composition comprises a fast disintegrating form of 3α-OH-5β-pregnan-20-one and a plurality of pharmaceutically acceptable additives.

In an embodiment, the 3α-OH-5β-pregnan-20-one composition or oral dosage forms may be formulated to efficiently provide amounts of 3α-OH-5β-pregnan-20-one that are therapeutically effective for treating a CNS disorder when orally administered to a subject. In another aspect, 3α-OH-5β-pregnan-20-one in the composition may be in a form that enables providing effective levels of 3α-OH-5β-pregnan-20-one when orally administered to a subject. In another aspect, 3α-OH-5β-pregnan-20-one may be in a form that, when orally administered to a subject, increases levels of 3α-OH-5β-pregnan-20-one in the subject. In another aspect, compositions of this invention, when orally administered to a subject, are expected to increase levels of 3α-OH-5β-pregnan-20-one in the subject as compared to a composition comprising an equivalent amount of micronized or non-micronized (e.g., crystalline) 3α-OH-5β-pregnan-20-one suspended in edible oil and orally administered to the subject.

In one embodiment, the composition may be formulated as an oral dosage form that has from about 10 mg to about 1200 mg of 3α-OH-5β-pregnan-20-one. In one aspect, the oral dosage form may be a liquid, a semi-liquid, a semi solid, a sprinkle, an emulsion, a dispersion, a granule, a syrup, a suspension, a capsule, a tablet, a chew, or a drink.

In yet another embodiment, dosage regiments and methods of treating a CNS disorder in a subject are provided and may include orally administering a composition comprising a therapeutically effective amount of 3α-OH-5β-pregnan-20-one.

In one embodiment, the compositions and oral dosage forms may include a plurality of pharmaceutically acceptable additives comprising at least one of alpha-tocopherol, glyceryl monocaprylate, glyceryl monocaprylocaprate, propylene glycol monolaurate, PEG-35 castor oil, PEG-40 hydrogenated castor oil, and a combination thereof that provides therapeutically effective levels of 3α-OH-5β-pregnan-20-one in an amount sufficient to treat a CNS disorder when orally administered to a subject.

In one aspect, the amount of 3α-OH-5β-pregnan-20-one in a composition may provide a therapeutically effective level (e.g. average serum levels, $C_{avg}$, or peak serum levels, $C_{max}$) of 3α-OH-5β-pregnan-20-one that is sufficient to treat the CNS disorder. In another aspect, 3α-OH-5β-pregnan-20-one in a composition may be in a fast releasing form that provides therapeutically effective levels of 3α-OH-5β-pregnan-20-one for treating the CNS disorder in the subject. In another aspect, 3α-OH-5β-pregnan-20-one in a composition may be in a solubilized or amorphous form that provides a therapeutically effective levels of 3α-OH-5β-pregnan-20-one for treating a CNS disorder in the subject. In a further aspect, the 3α-OH-5β-pregnan-20-one in a composition disclosed herein may be in a treated form with a plurality of additives that may include at least one surfactant that provides therapeutically effective levels of 3α-OH-5β-pregnan-20-one effective to treat a CNS disorder in a subject. In yet another aspect, the 3α-OH-5β-pregnan-20-one may be formulated with a plurality of additives that provide a therapeutically effective level of 3α-OH-5β-pregnan-20-one for treating a CNS disorder in a subject.

Compositions:

In an embodiment of the present invention, an oral pharmaceutical composition may include a therapeutically effective amount of 3α-OH-5β-pregnan-20-one and a plurality of pharmaceutically acceptable additives that provides 3α-OH-5β-pregnan-20-one in an amount sufficient to treat a CNS depression disorder when orally administered to a subject. In some aspects, the additives may maximize, speed, or otherwise improve absorption of 3α-OH-5β-pregnan-20-one from the composition when administered to a subject. In some aspects, the additives may improve the release rate and/or release amount of the 3α-OH-5β-pregnan-20-one when administered to a subject. In some aspects, the additives may improve solubilization of 3α-OH-5β-pregnan-20-one when administered to a subject. In some aspects, the additives, ingredients, shape and/or size of the dosage form (e.g. tablet or capsule) of the composition may improve the disintegration rate of the dosage form such as to 25 minutes or less.

In some aspects of the present invention, the form of 3α-OH-5β-pregnan-20-one in the composition may improve the release rate and/or release amount of the 3α-OH-5β-pregnan-20-one when tested in vitro or when administered to a subject. In some aspects, the form of 3α-OH-5β-pregnan-20-one in the composition may improve solubilization of the 3α-OH-5β-pregnan-20-one when administered to a subject.

When utilizing sulfobutylether-β-cyclodextrin (SBE-β-CD) oral compositions having solubilized or semi-solid 3α-OH-5β-pregnan-20-one, it may be challenging to load proper amounts of 3α-OH-5β-pregnan-20-one so as to deliver effective serum levels of 3α-OH-5β-pregnan-20-one due to limitations with respect to 3α-OH-5β-pregnan-20-one solubility in various cyclodextrin solutions including non-encapsulated SBE-β-CD. Moreover, high cyclodextrin amounts required for formulation with 3α-OH-5β-pregnan-20-one may also present safety concerns. In some aspects, the compositions and dosage forms of the present invention enable loading of higher amounts of 3α-OH-5β-pregnan-20-one as compared to non-encapsulated SBE-β-CD or any cyclodextrin solution compositions.

Figure 2:
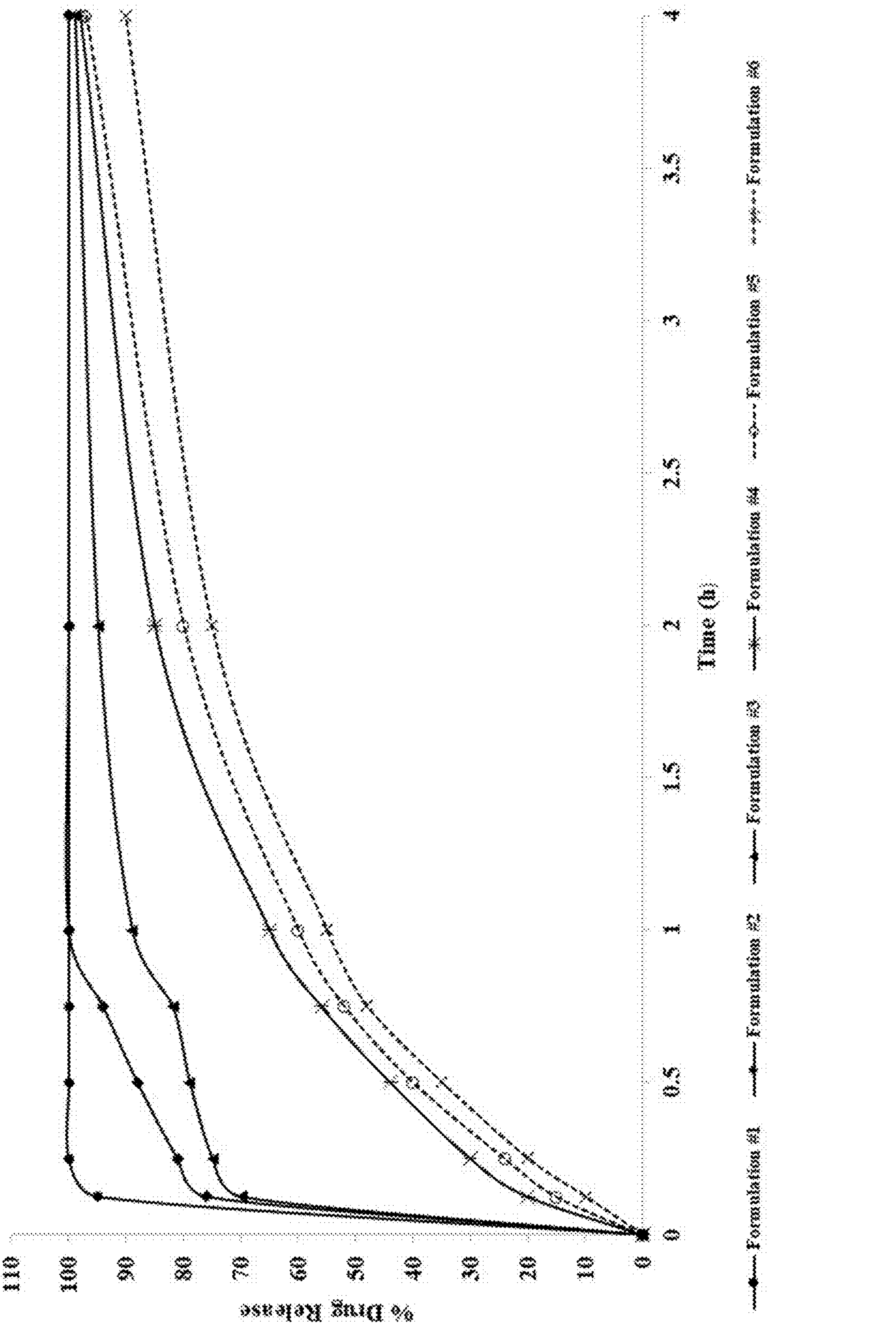
FIG. 2 shows plots of the 3α-OH-5β-pregnan-20-one release rate from one gram of each composition invented herein (Formulation #1, #2, and #3 in Example 2) as compared to a conventional tablet composition (Formulation #4 in Example 2), a composition of micronized crystalline 3α-OH-5β-pregnan-20-one suspension in a composition consisting essentially of canola oil (Formulation #5 in Example 2), and a composition of crystalline 3α-OH-5β-pregnan-20-one suspension in a composition consisting essentially of polysorbate 80 (Formulation #6 in Example 2), measured using a USP Type II dissolution apparatus in 900 mL of deionized water with 0.5% (w/v) of sodium lauryl sulfate at 75 rpm at 37° C.

In some aspects, the compositions and dosage forms of the present invention enable loading of 3α-OH-5β-pregnan-20-one of greater than 3% w/w when fully solubilized in the composition or in treated crystalline or noncrystalline forms of 3α-OH-5β-pregnan-20-one with at least one surfactant. FIG. 2 shows plots of the 3α-OH-5β-pregnan-20-one release rate from one gram of each composition disclosed herein (Formulations #1, #2, and #3 in Table G) compared to conventional compositions (Formulations #4, #5, and #6 in Table G). Formulations #1 and #2 comprise solubilized forms of 3α-OH-5β-pregnan-20-one and Formulation #3 comprises treated (micronized) crystalline forms of 3α-OH-5β-pregnan-20-one with a surfactant. As seen in FIG. 2, the compositions of the present invention may release greater than 25% more of 3α-OH-5β-pregnan-20-one as compared to compositions comprising a) a conventional tablet formulation without a surfactant (Formulation #4), b) a formulation of crystalline 3α-OH-5β-pregnan-20-one suspension in canola oil (Formulation #5), and c) a formulation of micronized crystalline 3α-OH-5β-pregnan-20-one suspension in polysorbate 80 (Formulation #6) after 30 minutes, when measured using a USP Type II dissolution apparatus in 900 mL of deionized water with 0.5% (w/v) of sodium lauryl sulfate at 75 rpm at 37° C.

Yet in another aspect, the compositions of the present invention may release greater than 70% of the 3α-OH-5β-pregnan-20-one after 30 minutes when measured using a USP Type II dissolution apparatus in 900 mL of deionized water with 0.5% (w/v) of sodium lauryl sulfate at 75 rpm at 37° C. In another aspect, the compositions of the present invention may release greater than at least 50% of 3α-OH-5β-pregnan-20-one after 15 minutes when measured using a USP Type II dissolution apparatus in 900 mL of deionized water with 0.5% (w/v) of sodium lauryl sulfate at 75 rpm at 37° C. In some aspects, a daily dose or dosing regimen may improve absorption of 3α-OH-5β-pregnan-20-one, when administered to a subject. In some aspects, the 3α-OH-5β-pregnan-20-one daily dose or dosing regimen may improve absorption of the 3β-OH-5β-pregnan-20-one (or an isomer of 3α-OH-5β-pregnan-20-one) when administered to a subject.

In another aspect, 3α-OH-5β-pregnan-20-one in the composition of the present invention may be in a form that, when orally administered to a subject, maximizes, speeds, or otherwise causes an increase in solubilized levels of 3α-OH-5β-pregnan-20-one in the gastrointestinal tract and/or serum levels of the subject. In one embodiment, 3α-OH-5β-pregnan-20-one in the composition of the present invention may be in a noncrystalline form that increases levels of 3α-OH-5β-pregnan-20-one as compared to a composition comprising an equivalent amount of 3α-OH-5β-pregnan-20-one in non-encapsulated SBE-β-CD solution when orally administered to a subject. For example, the levels of 3α-OH-5β-pregnan-20-one in a subject from the compositions invented herein may be at least 20% higher as compared to the 3α-OH-5β-pregnan-20-one levels obtained from a composition comprising an equivalent amount of 3α-OH-5β-pregnan-20-one in non-encapsulated SBE-β-CD solution when orally administered the subject.

The therapeutically effective amount of 3α-OH-5β-pregnan-20-one may vary. For example, the therapeutically effective amount of 3α-OH-5β-pregnan-20-one in the composition or oral dosage form of the instant invention may be, expressed as a percentage of the fill amount, equal to or greater than any one of: 0.0001 wt %, 0.001 wt %, 0.01 wt %, 0.1 wt %, 0.5 wt %, 1.0 wt %, 2.0 wt %, 5.0 wt %, 10.0 wt %, 15.0 wt %, 20.0 wt %, 30.0 wt %, 35.0 wt %, 40.0 wt %, 45.0 wt %, and 50.0 wt %. In another example, the therapeutically effective amount of 3α-OH-5β-pregnan-20-one may be present in the disclosed composition or oral dosage form in an amount of from about 5 mg to about 600 mg. In another example, the therapeutically effective amount of 3α-OH-5β-pregnan-20-one may be present in the disclosed composition or oral dosage form in an amount of from about 0.0001 wt % to about 10 wt %. In another example, the therapeutically effective amount of 3α-OH-5β-pregnan-20-one may be present in the disclosed composition or oral dosage form in an amount of from about 10 wt % to about 20 wt % of the composition or oral dosage form. In yet another example, the therapeutically effective amount of 3α-OH-5β-pregnan-20-one may be present in the disclosed composition or oral dosage form in an amount of from about 20 wt % to about 50 wt % of the composition or oral dosage form. In another example, the therapeutically effective amount of 3α-OH-5β-pregnan-20-one may be present in the disclosed composition or oral dosage form in an amount of from about 10 wt % to about 50 wt % or about 0.6 wt % to about 10 wt % of the composition or oral dosage form. In one aspect, the compositions and methods of this invention comprise 3α-OH-5β-pregnan-20-one in at least one form of substantially solubilized, partially solubilized, substantially non-solubilized, partially crystalline, partially non-micronized, substantially nanosized, substantially noncrystalline, amorphous solid, a solid dispersion, a solid solution, and a eutectic mixture that results in fast release (e.g., at least 50% of the 3α-OH-5β-pregnan-20-one is released after 15 minutes when measured using a USP Type II dissolution apparatus in 900 mL of deionized water with 0.5% (w/v) of sodium lauryl sulfate at 75 rpm at 37° C.).

In another aspect, the compositions and dosage forms of this invention include an "additive" that may be capable of fully or partially releasing/dissolving or solubilizing 3α-OH-5β-pregnan-20-one in the pharmaceutical composition. In one aspect, a wide variety of additives may be used to solubilize or disperse 3α-OH-5β-pregnan-20-one fully or partially in the pharmaceutical composition in order to provide therapeutically effective levels of 3α-OH-5β-pregnan-20-one so as to substantially reduce, improve, or eliminate a CNS disorder.

The therapeutically effective amount of 3α-OH-5β-pregnan-20-one may be combined with a plurality of pharmaceutically acceptable additives to provide 3α-OH-5β-pregnan-20-one in an amount sufficient to treat a CNS depression disorder when administered to a subject. In some embodiments, a wide variety of additives may be used to fully or partially solubilize or disperse 3α-OH-5β-pregnan-20-one in the pharmaceutical composition in order to provide therapeutically effective levels of 3α-OH-5β-pregnan-20-one for treating a CNS disorder. Examples of suitable additives may include but are not limited to: (i) tocopherol (e.g. vitamin E) or its derivatives; (ii) fatty acids or their salts; (iii) glyceryl fatty acid esters; (iv) PEG glycerides of fatty acid esters; (v) polyglycerol fatty acid esters; (vi) triglycerides; (vii) hydrogenated polyoxyl vegetable oils or glycerides; (viii) propylene glycol fatty acid esters; (ix) edible oils; (x) sterols or its derivatives, (xi) omega oils, such as omega fatty acids, fish oil, flax seed oil, algae oil, and the like, or combinations thereof.

Examples of suitable solubilizers may comprise, but are not limited to, tocopherol or its derivatives, fatty acid or its salts, glyceryl fatty acid esters, PEG glycerides of fatty acid esters, polyglycerol fatty acid esters, triglycerides, hydrogenated polyoxyl vegetable oils or glycerides, propylene glycol fatty acid esters, edible oils, and sterols or its derivatives.

In one aspect, vitamin E or its derivatives may comprise, but are not limited to: alpha-tocopherol, beta-tocopherol, gamma-tocopherol, delta-tocopherol, tocopherol acetate, tocopherol linoleate, tocopherol succinate, tocotrienols (alpha-, beta-, gamma-, or delta-), tocofersolan (see: tocofersolan on Wikipedia's website) or TPGS (PEG derivatives of alpha-tocopherol), the like, or combinations thereof.

In one embodiment, fatty acid or its salts may comprise, but not limited to, octanoic acid, capric acid, lauric acid, myristic acid, palmitic acid, stearic acid, oleic acid, linoleic acid, linoelaidic acid (see: linoelaidic acid on Wikipedia's website), sodium caproate, sodium caprylate, sodium laurate, sodium myristate, sodium palmitate, sodium oleate, sodium stearate, sodium lauryl sulfate, sodium lauryl sarcosinate (see: sodium lauryl sarcosinate on Wikipedia's website), sodium dioctyl sulfosuccinate, sodium cholate, and sodium taurocholate.

In another aspect, glyceryl fatty acid esters may comprise, but are not limited to: glyceryl monooleate, glyceryl monoleate/linoleate, glyceryl monolinoleate, glyceryl ricinoloeate, glyceryl monolaurate, glyceryl monopalmitate, glyceryl monostearate, glyceryl mono-/di-oleate, glyceryl palmitate/stearate, glyceryl acetate, glyceryl laurate, glyceryl citrate/lactate/oleate/linoleate, glyceryl caprylate, glyceryl caprylate/caprate, glyceryl dicaprylate/dicaprate, mono-/di-acetylated monoglycerides, glyceryl monostearate, glyceryl dilaurate, glyceryl dioleate, the like, or combinations thereof.

In yet another aspect, PEG glycerides of fatty acid esters may comprise, but are not limited to: PEG fatty acid monoesters, PEG glycerol fatty acid esters, PEG fatty acid diesters, PEG fatty acid mono-/di-ester mixtures, PEG triglycerides of fatty acid esters, the like, or combinations thereof. PEG glycerol fatty acid esters may comprise, but are not limited to: PEG glyceryl laurate, PEG glyceryl laurate, PEG glyceryl caprylate, PEG glyceryl caprate, PEG glyceryl oleate, PEG glyceryl mono-/di-fatty acid ester mixtures, the like, or combinations thereof. PEG fatty acid monoesters may comprise but are not limited to: esters of caprylic acid, capric acid, lauric acid, oleic acid, and stearic acid, the like, or combinations thereof. Examples of the PEG fatty acid monoesters may include PEG (1-100, 200, 300, 400) monocaprylate, PEG (1-100, 200, 300, 400) monocaprate, PEG (1-100, 200, 300, 400) monolaurate, PEG (1-100, 200, 300, 400) monooleate, PEG (1-100, 200, 300, 400) monopalmitate, PEG (1-100, 200, 300, 400) monostearate, and PEG (1-100, 200, 300, 400) monococoate, the like, or combinations thereof. PEG fatty acid diesters may comprise, but are not limited to, PEG (4-32) dicaprylate, PEG (4-32) dicaprate, PEG (4-32) dilaurate, PEG (4-32) dioleate, PEG (4-32) distearate, and PEG (4-32) dipalmitate, the like, or combinations thereof. PEG fatty acid mono-/di-ester mixtures may comprise but are not limited to: PEG caprylate/caprate, PEG mono-/di-caprylate, PEG mono-/di-caprate, PEG mono-/di-laurate, PEG mono-/di-oleate, and PEG mono-/di-stearate the like, or combinations thereof. PEG triglycerides of fatty acid esters may comprise, but are not limited to: lauroyl polyoxylglycerides, stearoyl polyoxylglycerides, oleoyl polyoxyl glycerides, linoleoyl polyoxyl glycerides, lauroyl polyoxyl glycerides, caprylocaproyl polyoxyl glycerides, and behenoyl polyoxylglycerides the like, or combinations thereof.

In a further aspect, polyglycerol fatty acid esters may comprise, but are not limited to: polyglyceryl (2, 3, 4, 6, 10) oleate, polyglyceryl (2, 3, 4, 6, 10) dioleate, polyglyceryl (2, 3, 4, 6, 10) trioleate, polyglyceryl (2, 3, 4, 6, 10) laurate, polyglyceryl (2, 3, 4, 6, 10) dilaurate, polyglyceryl (2, 3, 4, 6, 10) trilaurate, polyglyceryl (2, 3, 4, 6, 10) stearate, polyglyceryl (2, 3, 4, 6, 10) distearate, polyglyceryl (2, 3, 4, 6, 10) tristearate, polyglyceryl (2, 3, 4, 6, 10) mono-/dioleate, polyglyceryl (3,6,10) caprate, polyglyceryl (3,6,10) dicaprate, polyglyceryl (3,6,10) tricaprate, polyglyceryl (3,6,10) caprylate, polyglyceryl (3,6,10) dicaprylate, polyglyceryl (3,6,10) tricaprylate, polyglyceryl (3,6,10) polystearate, polyglyceryl (3,6,10) polyoleate, polyglyceryl (3,6,10) mono-/di-oleate, polyglyceryl (3,6,10) caprylate, polyglyceryl (3,6,10) polycaprylate, polyglyceryl (3,6,10) caprate, polyglyceryl (3,6,10) polycaprate, and polyglyceryl (3,6,10) caprylate/caprate, the like, or combinations thereof.

In another aspect, triglycerides may comprise, but are not limited to: glyceryl tricaprylate, glyceryl tricaprate, glyceryl tricaprylate/tricaprate, glyceryl tricaprylate/tricaprate/trisuccinate, glyceryl trioleate, glyceryl tristearate, glyceryl trilaurate, medium chain natural oils, the like, or combinations thereof.

In yet another aspect, hydrogenated polyoxyl vegetable oils or glycerides may comprise, but are not limited to: castor oil or hydrogenated castor oil, or an edible vegetable oil such as corn oil, olive oil, peanut oil, palm kernel oil, apricot kernel oil, peppermint oil, coconut oil, sunflower seed oil, or almond oil, the like, or combinations thereof. The polyoxyl group may include glycerol, propylene glycol, ethylene glycol, polyethylene glycol, sorbitol, pentaerythritol, the like, or combinations thereof c Examples of hydrogenated polyoxyl vegetable oils or glycerides may comprise, but are not limited to: PEG-35 castor oil (Incrocas-35, KOLLIPHOR EL, Cremophor EL), PEG-40 hydrogenated castor oil (KOLLIPHOR RH 40, Cremophor RH40), PEG-25 trioleate (TAGATRTO), PEG-60 corn glycerides (CROVOL M70), PEG-60 almond oil (CROVOL A70), PEG-40 palm kernel oil (CROVOL PK70), PEG-50 castor oil (EMALEX C-50), PEG-50 hydrogenated castor oil (EMALEX HC-50), PEG-8 caprylic/capric glycerides (LABRASOL), PEG-6 caprylic/capric glycerides (SOFTIGEN 767), PEG-5 hydrogenated castor oil, PEG-7 hydrogenated castor oil, PEG-9 hydrogenated castor oil, PEG-6 corn oil (LABRAFIL M. 2125 CS), PEG-6 almond oil (LABRAFIL M 1966 CS), PEG-6 apricot kernel oil (LABRAFIL M 1944CS), PEG-6 olive oil (LABRAFIL M 1980 CS), PEG-6 peanut oil (LABRAFIL M 1969 CS), PEG-6 hydrogenated palm kernel oil (LABRAFIL M2130 BS), PEG-6 palm kernel oil (LABRAFIL M 2130 CS), PEG-6 triolein (LABRAFIL M 2735 CS), PEG-8 corn oil (LABRAFIL WL 2609 BS), PEG-20 corn glycerides (CROVOL M40), and PEG-20 almond glycerides (CROVOL A40), the like, or combinations thereof.

In one aspect, propylene glycol fatty acid esters may comprise, but are not limited to: propylene glycol monolaurate (LAUROGLYCOL FCC), propylene glycol ricinoleate (PROPYMULS), propylene glycol monooleate (MYVEROL P-06), propylene glycol dicaprylate/dicaprate (CAPTEX 200), and propylene glycol dioctanoate (CAPTEX 800), propylene glycol monocaprylate (CAPRYOL 90, NIKKOL SEFSOL 218), propylene glycol myristate, propylene glycol monostearate, propylene glycol ricinolate, propylene glycol isostearate, propylene glycol caprylate/caprate, propylene glycol dioleate, propylene glycol distearate, propylene glycol dilaurate, propylene glycol dicaprylate, and propylene glycol dicaprate, the like, or combinations thereof.

In another aspect, edible oils may comprise, but are not limited to, corn oil, olive oil, peanut oil, coconut oil, peppermint oil, sunflower seed oil, castor oil, safflower oil, borage oil, cottonseed oil, soybean oil, palm kernel oil, apricot kernel oil, almond oil, omega-3 oil, the like, or combinations thereof.

In one aspect, sterols or its derivatives may comprise, but are not limited to: cholesterol, sitosterol, lanosterol, phytosterol, its PEG derivatives, the like, or combinations thereof. In various aspects, sterols or its derivatives may be hydrophilic or lipophilic. Examples of hydrophilic sterols include but are not limited to: lanosterol PEG-24 cholesterol ether (e.g. SOLULAN C-24, AMERCHOL), PEG-30 soya sterol (e.g. NIKKOL BPS-30, from Nikko), PEG-25 phytosterol (e.g. NIKKOL BPSH-25 from Nikko), PEG-30 cholestanol (e.g. NIKKOL DHC from Nikko). Examples of Lipophilic Sterol Surfactants are Cholesterol, sitosterol, phytosterol (e.g. GENEROL series from Henkel), PEG-5 soya sterol (e.g. NIKKOL BPS-S, from Nikko), PEG-10 soya sterol (e.g. NIKKOL BPS-10 from Nikko), PEG-20 soya sterol (e.g. NIKKOL BPS-20 from Nikko), the like, or combinations thereof.

In one embodiment, an additive may be a substance that may be added to the pharmaceutical composition to enhance the release, separation, or dispersion of the active agent, or to enhance the dissolution and further absorption of the active agent into the body. Examples of additives may include a lipophilic additive when it has an HLB value of 10 or less, and a hydrophilic additive when it has an HLB value of greater than 10.

In one aspect, the pharmaceutically acceptable additive may comprise a hydrophilic additive, a lipophilic additive, or a combination thereof.

For example, lipophilic additives may comprise, but are not limited to: mono-, di-glycerides of fatty acids, reaction mixtures of alcohols or polyalcohols with a variety of natural and/or hydrogenated oils such as PEG-5 hydrogenated castor oil, PEG-7 hydrogenated castor oil, PEG-9 hydrogenated castor oil, PEG-6 corn oil (e.g. LABRAFIL M 2125 CS), PEG-6 almond oil (e.g. LABRAFIL M 1966 CS), PEG-6 apricot kernel oil (e.g. LABRAFIL M 1944 CS), PEG-6 olive oil (e.g. LABRAFIL M 1980 CS), PEG-6 peanut oil (e.g. LABRAFIL M 1969 CS), PEG-6 hydrogenated palm kernel oil (e.g. LABRAFIL M 2130 BS), PEG-6 palm kernel oil (e.g. LABRAFIL M 2130 CS), PEG-6 triolein (e.g. LABRAFIL M 2735 CS), PEG-8 corn oil (e.g. LABRAFIL WL 2609 BS), PEG-20 corn glycerides (e.g. CROVOL M40), PEG-20 almond glycerides (e.g. CROVOL A40), lipophilic polyoxyethylene-polyoxypropylene block co-polymers: poloxamers (e.g. Pluronic L92, L101, L121 etc.), propylene glycol fatty acid esters, such as propylene glycol monolaurate (e.g. Lauroglycol FCC), propylene glycol ricinoleate (e.g. Propymuls), propylene glycol monooleate (e.g. MYVEROL P-06), propylene glycol dicaprylate/dicaprate (e.g. CAPTEX 200), and propylene glycol dioctanoate (e.g. CAPTEX 800), propylene glycol mono-caprylate (e.g. CAPRYOL 90); propylene glycol oleate (e.g. LUTROL OP2000); propylene glycol myristate; propylene glycol mono stearate; propylene glycol hydroxy stearate; propylene glycol ricinoleate; propylene glycol isostearate; propylene glycol mono-oleate; propylene glycol dicaprylate/dicaprate; propylene glycol dioctanoate; propylene glycol caprylate-caprate; propylene glycol dilaurate; propylene glycol distearate; propylene glycol dicaprylate; propylene glycol dicaprate; mixtures of propylene glycol esters and glycerol esters such as mixtures composed of the oleic acid esters of propylene glycol and glycerol (e.g. ARLACEL 186); sterol and sterol derivatives such as cholesterol, sitosterol, phytosterol, phytosterol fatty acid esters, PEG-5 soya sterol, PEG-10 soya sterol, PEG-20 soya sterol, and the like; glyceryl palmitostearate, glyceryl stearate, glyceryl distearate, glyceryl monostearate, or a combination thereof; sorbitan fatty acid esters such as sorbitan monolaurate (e.g. ARLACEL 20), sorbitan monopalmitate (e.g. Span-40), sorbitan monooleate (e.g. Span-80), sorbitan monostearate, and sorbitan tristearate, sorbitan monolaurate, sorbitan monopalmitate, sorbitan monooleate, sorbitan trioleate, sorbitan sesquioleate, sorbitan tristearate, sorbitan monoisostearate, sorbitan sesquistearate, and the like; fatty acids such as capric acid, caprylic acid, oleic acid, linoleic acid, myristic acid, menthol, menthol derivatives, lecithin, phosphatidyl choline, bile salts, and the like, and mixtures thereof. It is important to note that some lipophilic additives may also function as the solubilizer component of the compositions and oral dosage forms. In some cases, an additive for the compositions and oral dosage forms may be a lipophilic surfactant.

In one embodiment, the pharmaceutically acceptable additive may be free of polysorbate 80. In another embodiment, the pharmaceutically acceptable additive may be free of cyclodextrin. In a further embodiment, the pharmaceutically acceptable additive may be free of edible oil.

The pharmaceutically acceptable additive may also comprise a hydrophilic additive. In one aspect, the hydrophilic additive may comprise without limitation, non-ionic surfactants, ionic surfactants, zwitterionic surfactants, the like, or combinations thereof. Suitable hydrophilic surfactants may include but are not limited to: alcohol-oil transesterification products; polyoxyethylene hydrogenated vegetable oils; polyoxyethylene vegetable oils; alkyl sulphate salts, dioctyl sulfosuccinate salts; polyethylene glycol fatty acids esters; polyethylene glycol fatty acids mono- and di-ester mixtures; polysorbates, polyethylene glycol derivatives of tocopherol, polymers, the like, or combinations thereof. Two or more hydrophilic additives from the same or different classes may be referred to as the hydrophilic surfactant unless explicitly specified. In one aspect, non-limiting examples of hydrophilic surfactants may comprise PEG-8 caprylic/capric glycerides, lauroyl macrogol-32 glyceride, stearoyl macrogol glyceride, PEG-40 hydrogenated castor oil, PEG-35 castor oil, sodium lauryl sulfate, sodium dioctyl sulfosuccinate, polyethylene glycol fatty acids mono- and di-ester mixtures, polysorbate 80, polysorbate 20, polyethylene glycol 1000 tocopherol succinate, phytosterols, phytosterol fatty acid esters, poloxamers, the like, or combinations thereof. In some cases, a hydrophilic additive for the compositions and oral dosage forms may be a hydrophilic surfactant.

The pharmaceutically acceptable additive may be combined with or otherwise include additives in various amount ranges. For example, the lipophilic additive and hydrophilic additive may be present in amounts such that the amount (wt %) of lipophilic additive is greater than or equal to the amount (wt %) of hydrophilic additive. In another aspect, the lipophilic additive and hydrophilic additive may be present in amounts such that the ratio of amount (wt %) of lipophilic additive to amount (wt %) of hydrophilic additive is greater than about 2:1. In another aspect, the lipophilic additive and hydrophilic additive may be present in amounts such that the ratio of amount (wt %) of lipophilic additive to amount (wt %) of hydrophilic additive is greater than about 3:1. In still another aspect, the lipophilic additive and hydrophilic additive may be present in amounts such that the ratio of amount (wt %) of lipophilic additive to amount (wt %) of hydrophilic additive is at least greater than about 5:1.

In one embodiment, the compositions and oral dosage forms may include a pharmaceutically acceptable additive comprising at least one of alpha-tocopherol, glyceryl monocaprylate, glyceryl caprylocaprate, propylene glycol monolaurate, PEG-35 castor oil, PEG-40 hydrogenated castor oil, and a combination thereof that provides adequate levels of 3α-OH-5β-pregnan-20-one in an amount sufficient to treat a CNS disorder when orally administered to a subject.

In certain examples, the lipophilic additive may make up about 0.6% w/w to about 95% w/w, about 5% w/w to about 70% w/w, about 10% w/w to about 60% w/w, about 15% w/w to about 55% w/w, about 20% w/w to about 50% w/w, about 30% w/w, about 35% w/w, about 40% w/w, about 45% w/w, about 50% w/w, about 55% w/w, about 60% w/w, about 65% w/w, about 70% w/w, about 75% w/w, about 80% w/w, about 85% w/w, about 90% w/w or about 95% w/w of any pharmaceutical composition described herein. In some examples, the hydrophilic additive may make up about 1% w/w to about 50% w/w, about 5% w/w to about 45% w/w, about 10% w/w to about 40% w/w, about 15% w/w to about 35% w/w, about 20% w/w to about 30% w/w, about 5% w/w, about 6% w/w, about 7% w/w, about 8% w/w, about 9% w/w, about 10% w/w, about 15% w/w, about 20% w/w, about 25% w/w, or about 30% w/w of any pharmaceutical composition described herein.

In certain examples, the additive may be a surfactant. The surfactant in the present invention may be any compound containing polar or charged hydrophilic moieties as well as non-polar hydrophobic (lipophilic) moieties; i.e. a surfactant compound must be amphiphilic. Within the context of the present invention, the hydrophilic surfactant may be any hydrophilic surfactant suitable for use in pharmaceutical compositions. Such surfactants may be anionic, cationic, zwitterionic or non-ionic. Mixtures of hydrophilic surfactants are also within the scope of the invention. Similarly, the hydrophobic surfactant may be any hydrophobic surfactant suitable for use in pharmaceutical compositions. Mixtures of hydrophobic surfactants are also within the scope of the invention. Generally, suitable hydrophilic surfactants will have an HLB value greater than about 10 and suitable hydrophobic surfactants will have an HLB value less than about 10. The choice of specific hydrophobic and hydrophilic surfactants should be made keeping in mind the particular hydrophobic therapeutic agent to be used in the composition, and the range of polarity appropriate for the chosen therapeutic agent. With these general principles in mind, a very broad range of surfactants is suitable for use in the present invention.

In one embodiment, the pharmaceutically acceptable additive may optionally include at least one surfactant. When present, the surfactant may comprise about 0.5 wt % to about 50 wt % of the oral solid dosage form. In one embodiment, the surfactant may comprise about 2 wt % to about 50 wt % of the oral solid dosage form. In one embodiment, the surfactant may comprise about 5 wt % to about 27 wt % of the oral solid dosage form. In one embodiment, the surfactant may be a hydrophilic surfactant. A hydrophilic surfactant has a surface active property and may have an HLB value of 10 or more. The hydrophilic surfactants may be an anionic or non-ionic surfactant. Non-limiting examples of hydrophilic surfactants that may be included in the oral solid dosage forms include at least one or a combination of sodium lauryl sulphate, polysorbates, sodium docusate, polyoxyl castor oils, polyoxyl hydrogenated castor oils, poloxamers, lecithin or its derivatives, and mixtures thereof.

Poloxamer represents Polyethylene-Polyoxypropylene Block Copolymer and may be any kind of the following formula: HO(C<2>H<4>O)<a>(C<3>H<6>O)<b>(C<2>H<4>O) <a>H, where "a" and "b" denote the number of polyoxyethylene and polyoxypropylene units, respectively. The compounds are listed by generic name, with the corresponding "a" and "b" values. Poloxamer may be represented in a form of (C<3>H<6>O)<b>(C<2>H<4>O) <a>H (HLB)), such as (Poloxamer 105 (a=11, b=16 (8))); (Poloxamer 108 (a=46, b=16 (>10))); (Poloxamer 122 (a=5, b=21 (3))); (Poloxamer 123 (a=7, b=21 (7))); (Poloxamer 124 (a=11, b=21 (>7))); (Poloxamer 181 (a=3, b=30)); (Poloxamer 182 (a=8, b=30 (2)); (Poloxamer 183 (a=10, b=30)); (Poloxamer 184 (a=13, b=30)); (Poloxamer 185 (a=19, b=30)); (Poloxamer 188 (a=75, b=30 (29)); (Poloxamer 212 (a=8, b=35)); (Poloxamer 215 (a=24, b=35)); (Poloxamer 217 (a=52, b=35)); (Poloxamer 231 (a=16, b=39)); (Poloxamer 234 (a=22, b=39)); (Poloxamer 235 (a=27, b=39)); (Poloxamer 237 (a=62, b=39 (24)); (Poloxamer 238 (a=97, b=39)); (Poloxamer 282 (a=10, b=47)); (Poloxamer 284 (a=21, b=47)); (Poloxamer 288 (a=122, b=47 (>10)); (Poloxamer 331 (a=7, b=54 (0.5)); (Poloxamer 333 (a=20, b=54)); (Poloxamer 334 (a=31, b=54)); (Poloxamer 335 (a=38, b=54)); (Poloxamer 338 (a=128, b=54)); (Poloxamer 401 (a=6, b=67)); (Poloxamer 402 (a=13, b=67)); (Poloxamer 403 (a=21, b=67)); (Poloxamer 407 (a=98, b=67)); and combinations thereof.

In one embodiment, the oral compositions described herein may be free of any modulator that slows the release rate of 3α-OH-5β-pregnan-20-one in an aqueous media or in vivo.

In an embodiment, the composition is non-aqueous.

In another embodiment the composition is a non-aqueous composition filled in a capsule or a tablet dosage form.

In another embodiment, the oral solid dosage form(s) described herein may be free of synchronized release characteristics for 3α-OH-5β-pregnan-20-one with a solubilizer in an aqueous media so that the dosage form can release more than 90% of 3α-OH-5β-pregnan-20-one within 4 hours post administration or in vitro testing. Or stated differently, the release of the active agent may not be synchronous with the release of the lipophilic additives. For instance, the release of the active agent may not be at a rate that is similar to the rate of release of the additives.

Other ingredients: Although not always necessary, the compositions of the present invention may also include one or more additional components, i.e., functional ingredients. Classes of ingredients that may be present in the compositions include, but are not limited to, solvents, absorbents, acids, adjuvants, anticaking agent, glidants, antitacking agents, antifoamers, anticoagulants, antimicrobials, antioxidants, antiphlogistics, astringents, antiseptics, bases, binders, chelating agents, sequestrants, coagulants, coating agents, colorants, dyes, pigments, compatiblizers, complexing agents, softeners, crystal growth regulators, denaturants, desiccants, drying agents, dehydrating agents, diluents, dispersants, emollients, emulsifiers, encapsulants, enzymes, fillers, extenders, flavor masking agents, flavorants, fragrances, gelling agents, hardeners, stiffening agents, humectants, lubricants, moisturizers, bufferants, pH control agents, plasticizers, soothing agents, demulcents, retarding agents, spreading agents, stabilizers, suspending agents, sweeteners, disintegrants, thickening agents, consistency regulators, surfactants, opacifiers, polymers, preservatives, antigellants, rheology control agents, UV absorbers, tonicifiers and viscomodulators. One or more ingredients from any particular class, as well as one or more different classes of ingredients, may be present in the compositions. Specific examples of ingredients and their level of use are known in the art.

Other ingredients such as co-solvents may partially solubilize 3α-OH-5β-pregnan-20-one when presented in an effective amount. Examples of suitable co-solvents may comprise without limitation: alcohols and polyols, such as ethanol, propanol, isopropanol, butanol, benzyl alcohol, ethylene glycol, propylene glycol, butanediols, glycerin or its derivatives thereof, glycerol, diglycerol, polyglycerol, pentaerythritol, sorbitol, mannitol, transcutol, dimethyl isosorbide, triacetin, trimethyl citrate, polyethylene glycol, polypropylene glycol, polyvinylalcohol, hydroxypropyl methylcellulose and other cellulose derivatives, and the like, or combinations thereof.

Figure 3:
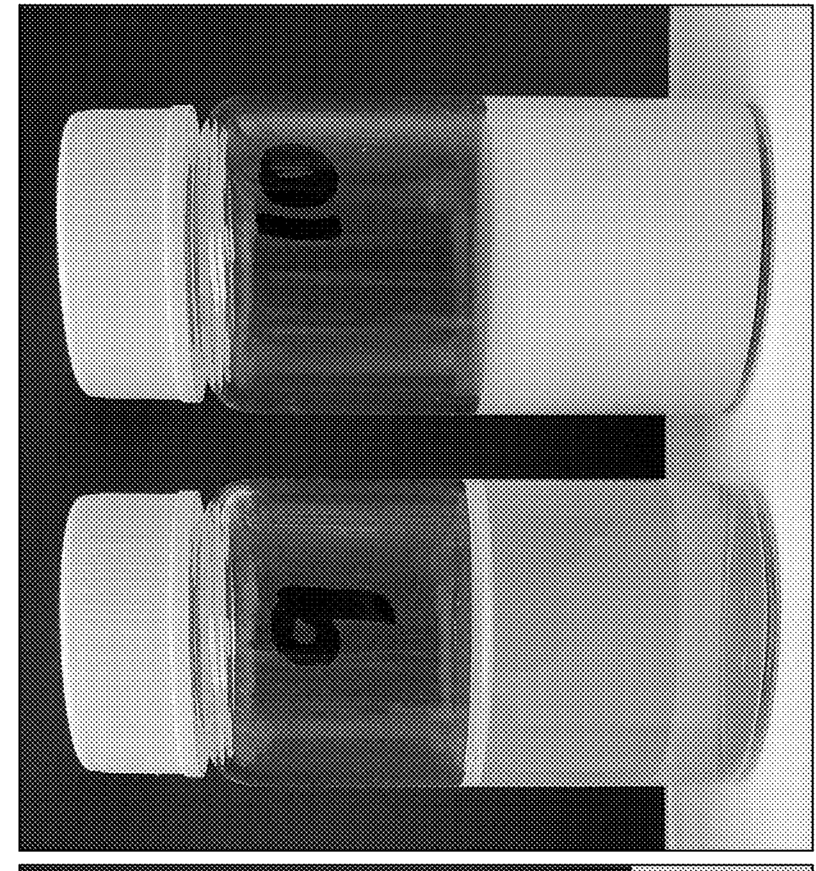
FIG. 3 is an image of comparative dispersibility of the oral compositions of the present invention comprising 3α-OH-5β-pregnan-20-one (Formulation #9 and #10 in Example 2) upon aqueous dilution (×100) with pH 6.8 simulated intestinal fluid per USP 26 compared to dispersibility of the compositions comprising solubilized 3α-OH-5β-pregnan-20-one in a solution consisting essentially of medium chain triglyceride (e.g. MIGLYOL 812, Formulation #7 in Example 2) and in a solution consisting essentially of in canola oil (Formulation #8 in Example 2).
Figure 3:
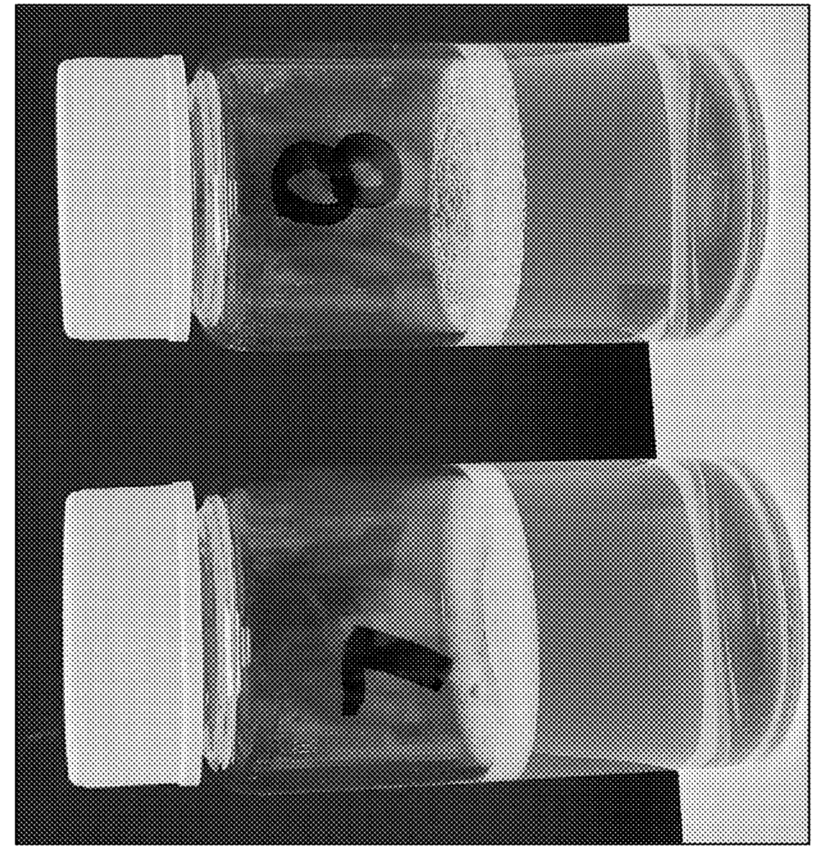

In one aspect, the composition may be formulated as a solution, an emulsion, a liquid, a semi-liquid, a suspension, a semi solid, a sprinkle, an emulsion, a dispersion, a granule, a syrup, a suspension, a capsule, a tablet, a chew, or a drink, or the like, or combinations thereof. In one example, the composition may form a dispersion, an emulsion, a solution, or a micellar solution upon 10× or 100× dilution with an aqueous bile salt comprising simulated gastric or intestinal media or water (e.g. FeSSIF (see: FeSSIF on Biorelevant's website), or FaSSIF media well known in the art). In another example, the composition may remain substantially solubilized upon 10× or 100× dilution with an aqueous bile salt comprising simulated gastric or intestinal media or water. In another example, the composition may form a dispersion upon 10× or 100× dilution with an aqueous bile salt comprising simulated gastric or intestinal media or water with a mean dispersion particle size of less than 300 nm or a UV absorbance of less than 5.0 units when measured at 450 nm. FIG. 3 shows an image of exemplary comparative dispersibility of the disclosed oral compositions comprising 3α-OH-5β-pregnan-20-one (Formulation #9 and #10 in Table G) upon aqueous dilution (×100) with pH 6.8 simulated intestinal fluid per USP 26 compared to dispersibility of compositions comprising solubilized 3α-OH-5β-pregnan-20-one in medium chain triglycerides (e.g. MIGLYOL 812; Formulation #7 in Table G) and in canola oil (Formulation #8 in Table G). As shown in FIG. 3, Formulation #7 and #8 were not dispersed nor solubilized in the ×100 diluted aqueous media (oily contents at the surface were fully separated from the aqueous media), while the compositions of the disclosed invention (Formulation #9 and #10) were well dispersed. UV absorbance measured at 450 nm was not measurable for Formulation #7 and #8 due to separation of phases, while measurements of 1.3 Abs and 3.2 Abs were observed for Formulation #9 and #10, respectively (for Abs, see: Spectrophotometry on the website of the Missouri university of science and technology).

In one embodiment, the 3α-OH-5β-pregnan-20-one in the composition may comprise a fully or partially crystalline form that is treated, solubilized, amorphous solid, solid solution, solid dispersion, or the like, or combinations thereof. In one aspect, the composition of this invention consists of only 3α-OH-5β-pregnan-20-one active in the additives. In one another aspect, a specified weight percentage of 3α-OH-5β-pregnan-20-one in the composition or dosage form may be in a noncrystalline form (e.g., amorphous solid, a solution, an emulsion, a liquid, a semi-liquid, or the like). In one example, at least about 50% of the 3α-OH-5β-pregnan-20-one in the composition may be in a noncrystalline state. In another example, at least about 65% of the 3α-OH-5β-pregnan-20-one in the composition may be in a noncrystalline state. In yet another example, at least about 80% of the 3α-OH-5β-pregnan-20-one in the composition may be in a noncrystalline state. In another example, at least about 95% of the 3α-OH-5β-pregnan-20-one in the composition may be in a noncrystalline state.

In one embodiment, oral compositions invented herein may be substantially treated crystalline solid forms of 3α-OH-5β-pregnan-20-one with at least one surfactant.

As used herein, the term "treated" may be applied to either crystalline forms of the active agent or to noncrystalline forms of the active agent. Further as used herein, where applied to crystalline forms of the active agent, the term "treated" means having been subjected to processing as exemplified by the active agent processed into an active agent in the form of at least one of grinded, sieved, milled, micronized, and nanosized, and where applied to noncrystalline forms of the active agent, the term "treated" is exemplified by the active agent processed into an active agent in the form of at least one of amorphous and fully solubilized. As used herein, the term "untreated" is defined as raw ("as is") or unprocessed active agent as exemplified by non-micronized or non-milled. This treatment of reducing particle sizes of the active agent helps in improving the release rate, dissolution rate, and bioavailability of the active agent. In one example, the original powder of 3α-OH-5β-pregnan-20-one to be used in the compositions of this invention is treated, such as grinded, sieved, milled, micronized, nanosized, amorphous, or fully solubilized before formulating in the compositions. Further for example, a "micronized" treatment may provide approximately the particle size distribution of 3α-OH-5β-pregnan-20-one ranging over D50=~6 μm and D90=~20 μm. Further still for example, a "nanosized" treatment may provide approximately the particle size distribution of 3α-OH-5β-pregnan-20-one ranging over D50=~150 nm and D90=~300 nm. D10, D50 and D90 are defined as follows: D10=10% of the population of particles in a composition have a size that lies below a designated value. D50=50% of the population of particles in a composition have a size that lies below a designated value. D90=90% of the population of particles in a composition have a size that lies below a designated value.

In one embodiment, the particle size distribution of the treated crystalline form of 3α-OH-5β-pregnan-20-one in this invention may range from D90=about 250 nm to about 250 μm. In one aspect, the particle size distribution of the treated 3α-OH-5β-pregnan-20-one crystalline forms in this invention may be less than D90=about 250 μm, such as one of D90=about 250 nm, D90=about 300 nm, D90=about 350 nm, D90=about 400 nm, D90=about 500 nm, D90=about 750 nm, D90=about 1 μm, D90=about 2 μm, D90=about 5 μm, D90=about 10 μm, D90=about 15 μm, D90=about 20 μm, D90=about 30 μm, D90=about 40 μm, D90=about 50 μm, D90=about 75 μm, D90=about 100 μm, D90=about 150 μm, D90=about 200 μm, D90=about 250 μm, and any D90 size between the above values. In another embodiment, the particle size distribution of the treated crystalline form of 3α-OH-5β-pregnan-20-one in this invention may be less than D90=about 75 μm.

In one embodiment, the particle size distribution of the treated crystalline form of 3α-OH-5β-pregnan-20-one in this invention may range from D50=about 150 nm to about 100 μm. In one aspect, the particle size distribution of the treated 3α-OH-5β-pregnan-20-one crystalline forms in this invention may be less than D50=about 100 μm, such as one of D50=about 100 nm, D50=about 150 nm, D50=about 200 nm, D50=about 250 nm, D50=about 300 nm, D50=about 350 nm, D50=about 400 nm, D50=about 500 nm, D50=about 750 nm, D50=about 1 μm, D50=about 2 μm, D50=about 5 μm, D50=about 10 μm, D50=about 15 μm, D50=about 20 μm, D590=about 30 μm, D50=about 40 μm, D50=about 50 μm, D50=about 75 μm, D50=about 100 μm, and any D50 size between the above values. In another embodiment, the particle size distribution of the treated crystalline form of 3α-OH-5β-pregnan-20-one in this invention may be D50=any size between about 150 nm and about 50 μm.

In one embodiment, the particle size distribution of the treated crystalline form of 3α-OH-5β-pregnan-20-one in this invention may range from D10=about 50 nm to about 50 μm. In one aspect, the particle size distribution of the treated 3α-OH-5β-pregnan-20-one crystalline forms in this invention may be less than D10=about 50 μm, such as one of D10=about 50 nm, D10=about 100 nm, D10=about 150 nm, D10=about 200 nm, D10=about 250 nm, D10=about 300 nm, D10=about 350 nm, D10=about 400 nm, D10=about 500 nm, D10=about 750 nm, D10=about 1 μm, D10=about 2 μm, D10=about 5 μm, D10=about 10 μm, D10=about 15 μm, D10=about 20 μm, D10=about 25 μm, D10=about 40 μm, D10=about 50 μm, and any D10 size between the above values. In another embodiment, the particle size distribution of the treated crystalline form of 3α-OH-5β-pregnan-20-one in this invention may be greater than D10=about 1 μm.

In another aspect, a specified weight percentage of the 3α-OH-5β-pregnan-20-one in the composition or dosage form may be solubilized. In one example, from about 50% to about 100% of the 3α-OH-5β-pregnan-20-one in the composition may be solubilized. In another example, from about 50% to about 65% of the 3α-OH-5β-pregnan-20-one in the composition may be solubilized. In yet another example, from about 65% to about 85% of the 3α-OH-5β-pregnan-20-one in the composition may be solubilized. In another example, from about 85% to about 100% of the 3α-OH-5β-pregnan-20-one in the composition may be solubilized. In another example, from about 85% to about 100% of the 3α-OH-5β-pregnan-20-one in the composition may be solubilized in a plurality of additives essentially free of SBE-β-CD.

In another embodiment, an oral pharmaceutical composition or oral dosage form may include an amount of 3α-OH-5β-pregnan-20-one that provides desirable GABAA receptor binding efficiency in therapeutically effective amounts that may treat CNS disorders when administered to a subject. For example, in one embodiment, the composition or oral dosage form may include a plurality of pharmaceutically acceptable additives that maximize or otherwise accelerate absorption of 3α-OH-5β-pregnan-20-one when administered to a subject.

Dosage Forms and Dosing Regimens

In one embodiment, the composition may be formulated as an oral dosage form. The oral dosage form may be selected from the group consisting of: a liquid, a semi-liquid, a semi solid, a sprinkle, an emulsion, a dispersion, a granule, a syrup, a suspension, a capsule, a tablet, a chew, a drink, or the like, or combinations thereof. In one aspect, the composition may be formulated as an oral dosage form that has from about 10 mg to about 600 mg of 3α-OH-5β-pregnan-20-one. In another aspect, the composition may be formulated as an oral dosage form that has from about 10 mg to about 600 mg of 3α-OH-5β-pregnan-20-one that, when orally administered to a subject, provides a 3α-OH-5β-pregnan-20-one $C_{max}$ of greater than about 4 ng/ml regardless of the consumption of a meal when measured using a liquid chromatograph or gas chromatograph-combined mass spectrometry method (e.g., LC-MS, LC-MSMS, or GC-MS).

The oral pharmaceutical composition comprising 3α-OH-5β-pregnan-20-one may be administered as an oral dosage form, such as a solid, a liquid, or a partially or a fully solubilized oral dosage form traditionally intended to substantially release and deliver 3α-OH-5β-pregnan-20-one in the gastrointestinal tract beyond the mouth and/or buccal cavity.

In certain embodiments, the oral pharmaceutical composition comprising 3α-OH-5β-pregnan-20-one may be administered as solid dosage forms known in the art. Examples of solid dosage forms may include but are not limited to, two-piece hard gelatin capsules, soft gelatin capsules, beads, beadlets, granules, spherules, pellets, microcapsules, microspheres, nanospheres, nanocapsules, tablets, and combinations thereof.

In certain embodiments, the oral pharmaceutical composition comprising 3α-OH-5β-pregnan-20-one may be administered as a liquid (e.g., solution, suspension, drink, etc.), or partially or fully solubilized forms in gelatin or non-gelatin capsules known in the art. The gelatin capsule may be a soft gelatin capsule or a hard gelatin capsule or any other capsule. The hard gelatin capsule may be a two-piece, standard gelatin capsule which typically includes a first bottom portion and a second top capsule portion. The soft gelatin capsule may be a two-piece capsule wherein two portions are sealed together or a one-piece, substantially hermetically sealed capsule.

In certain embodiments, the pharmaceutical composition may be administered to a subject in need of 3α-OH-5β-pregnan-20-one for CNS disorders. In a particular embodiment, the amount of 3α-OH-5β-pregnan-20-one administered ranges from about 150 mg to about 750 mg, from about 200 mg to about 1200 mg, from about 50 mg to about 500 mg, about 50 mg to about 400 mg, about 50 mg to about 300 mg, or about 50 mg to about 200 mg. In certain specific embodiments, the active ingredient is 3α-OH-5β-pregnan-20-one.

In other embodiments, 3α-OH-5β-pregnan-20-one may be administered to a subject (e.g., males and females) in need for the oral pharmaceutical compositions in this disclosure so that the subject receives a therapeutically effective amount of 3α-OH-5β-pregnan-20-one from the oral compositions. In an embodiment, 3α-OH-5β-pregnan-20-one in the oral compositions ranges from about 10 mg to about 600 mg, and about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, about 200 mg, about 250 mg, about 300 mg, about 350 mg, about 400 mg, about 450 mg, about 500 mg, about 600 mg, or any amount within the range of the noted values.

In particular embodiments, the amount of 3α-OH-5β-pregnan-20-one per dose from the oral pharmaceutical composition invented herein administered to a subject in need thereof, may range from about 150 mg to about 750 mg, about 200 mg to 1200 mg, about 10 mg to about 500 mg, about 50 mg to about 400 mg, from about 20 mg to about 300 mg, or from about 30 mg to about 200 mg. In certain embodiments, the amount of 3α-OH-5β-pregnan-20-one from the oral pharmaceutical composition invented herein administered to a subject in need thereof may be about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 900 mg, about 1000 mg, about 1100 mg, about 1200 mg, or any amount within the noted values.

To receive the desired therapeutic levels of 3α-OH-5β-pregnan-20-one per dose, in certain embodiments, the human in need thereof may be administered the oral pharmaceutical composition invented herein comprising about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, about 200 mg, about 300 mg, about 400 mg, about 500 mg, about 550 mg, about 600 mg, about 650 mg, about 700 mg, about 750 mg, about 800 mg, about 900 mg, about 1000 mg, about 1100 mg, about 1200 mg, or any amount within the noted values.

In one embodiment, the amount of 3α-OH-5β-pregnan-20-one in the oral pharmaceutical composition invented herein may range from about 0.6 weight percent to about 50 weight percent of the composition. In a further embodiment, a subject in need thereof may be administered with the oral pharmaceutical composition having a weight % amount of 3α-OH-5β-pregnan-20-one of about 0.6%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 22%, about 24%, about 25%, about 26%, about 28%, about 30%, about 35%, about 40%, about 45%, about 50%, or any percentage within the noted values.

In certain embodiments, the oral pharmaceutical compositions comprising 3α-OH-5β-pregnan-20-one in this disclosure may be administered once daily within any of the above noted amounts until the disease or condition is reduced or substantially eliminated. In other embodiments, the oral pharmaceutical compositions in this disclosure may be administered twice daily within any of the above noted amounts until the disease or condition is reduced or substantially eliminated. In yet further embodiments, the oral pharmaceutical compositions in this disclosure may be administered equal to or more than three times daily within any of the above noted amounts until the disease or condition is reduced or substantially eliminated.

The composition disclosed herein may have a daily dose of varying amounts. In one aspect, the therapeutically effective amount of the 3α-OH-5β-pregnan-20-one may be orally administered from one time to twelve times per day. In one example, the daily dose of the therapeutically effective amount of 3α-OH-5β-pregnan-20-one may comprise from about 150 mg to about 750 mg. In another example, the daily dose of the therapeutically effective amount of 3α-OH-5β-pregnan-20-one may comprise from about 200 mg to about 1200 mg. In a further example, the daily dose of the therapeutically effective amount of 3α-OH-5β-pregnan-20-one may comprise from about 10 mg to about 500 mg. In a further example, the daily dose of 3α-OH-5β-pregnan-20-one may be a fixed dose of from about 50 mg to about 500 mg. In a further example, the daily dose of 3α-OH-5β-pregnan-20-one may be a fixed dose of from about 150 mg to about 750 mg. In a further example, the daily dose of 3α-OH-5β-pregnan-20-one may be a fixed dose of from about 200 mg to about 1200 mg. In a further example, the daily dose of 3α-OH-5β-pregnan-20-one may be a fixed dose of from about 50 mg to about 1200 mg. In yet another aspect, a dose of 3α-OH-5β-pregnan-20-one may be administered in a dose form comprising from one to four capsules.

In one embodiment the daily dose of therapeutically effective amount of 3α-OH-5β-pregnan-20-one may comprise at least one of about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 300 mg, about 400 mg, about 450 mg, about 500 mg, about 550 mg, about 600 mg, about 650 mg, about 700 mg, about 750 mg, about 800 mg, about 900 mg, about 1000 mg, about 1100 mg, about 1200 mg, or any amount within the noted values.

In other aspect, 3α-OH-5β-pregnan-20-one may be administered to a subject (e.g., males and females) to provide a therapeutically effective level of 3α-OH-5β-pregnan-20-one. In one example, the 3α-OH-5β-pregnan-20-one in the oral compositions may have a total daily dose that ranges from about 50 mg to about 1200 mg, such as about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, about 200 mg, about 300 mg, about 400 mg, about 450 mg, about 500 mg, about 550 mg, about 600 mg, about 650 mg, about 700 mg, about 750 mg, about 800 mg, about 900 mg, about 1000 mg, about 1100 mg, about 1200 mg, or any amount within a range from about 50 mg to about 1200 mg.

In one aspect, the number of dosage form units (e.g. capsule, tablet, etc.) of 3α-OH-5β-pregnan-20-one per dose may range from one to four units, such as one, two, three, or four units.

To receive a therapeutic target level of 3α-OH-5β-pregnan-20-one per single dose, in some aspects, the subject may be administered with 3α-OH-5β-pregnan-20-one in amounts of from 10 mg to 1200 mg, such as about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, about 200 mg, about 250 mg, about 300 mg, about 400 mg, about 450 mg, about 500 mg, about 550 mg, about 600 mg, about 650 mg, about 700 mg, about 750 mg, about 800 mg, about 900 mg, about 1000 mg, about 1100 mg, about 1200 mg, or any amount within a range from about 10 mg to about 1200 mg.

In one aspect, the amount of the 3α-OH-5β-pregnan-20-one may be orally administered once daily in any recited amount until the CNS disease or condition is reduced or substantially eliminated. In one aspect, the oral compositions may be administered at any of the morning, the afternoon, the evening, and before bedtime. In another aspect, the oral compositions may be administered at about bedtime or before bedtime by any of about 5 hours, about 4 hours, about 3 hours, about 2 hours, and about 1 hour.

In other aspects, the oral pharmaceutical composition and/or oral dosage forms may be administered twice daily in any of the above noted amounts until the disease or condition is reduced or substantially eliminated. The oral compositions may be administered in the morning and evening, or 12 hours apart. In yet further aspects, the oral pharmaceutical composition or oral dosage form may be administered greater than or equal to three times daily in any of the recited amounts until the disease or condition is reduced or substantially eliminated. In one aspect, the oral compositions or dosage forms may be administered every 8 hours, every 6 hours, every 4 hours, every 3 hours, every 2 hours, or every 1 hour.

In one aspect, 3α-OH-5β-pregnan-20-one in the present invented compositions may be orally administered to the subject according to a dosage regimen for a specified duration of from about a single day to about 3 months. In another aspect, the oral pharmaceutical composition may be administered for 1 day, 2 days, 3 days, 4 days, 5 days, 6 days, 7 days, 8 days, 9 days, 10 days, 12 days, 14 days, 16 days, 18 days, 20 days, 21 days, 22 days, 24 days, 26 days, 28 days, or 30 days until the disease or condition is reduced or substantially eliminated. In one aspect, the oral pharmaceutical compositions may be administered for 1 week, 2 weeks, 3 weeks, 4 weeks, or 5 weeks until the disease or condition is reduced or substantially eliminated. In another aspect, the oral pharmaceutical may be administered for 1 month, 2 months, or 3 months until the disease or condition is reduced or substantially eliminated.

In one aspect, the oral pharmaceutical composition or dosage form may be administered with or without titration. In one aspect, the oral pharmaceutical compositions may be up-titrated to 25%, 33%, 50%, 100%, 150%, 200%, 300%, 400%, or 500% more than the initial (pre-titration) dose. In another aspect, the oral pharmaceutical compositions may be down-titrated to 75%, 50%, or 25% of the initial (pre-titration) dose. In an aspect, the oral pharmaceutical compositions may be administered with the fixed dose or the consistent dose as the initial dose.

In one aspect, the oral pharmaceutical composition or dosage form may be titrated to a subsequent 3α-OH-5β-pregnan-20-one dose based on a pharmacokinetic or pharmacodynamic response to an initial dose by a subject. In one example, the composition or oral dosage form may be orally administered in an initial 3α-OH-5β-pregnan-20-one dose of from about 40 mg to about 1200 mg and titrated to a maintenance 3α-OH-5β-pregnan-20-one dose that is about 25% to about 400% of the initial dose. In one example, the 3α-OH-5β-pregnan-20-one dose may be increased or decreased from about 0.25× to about 4× of an initial 3α-OH-5β-pregnan-20-one dose to a 3α-OH-5β-pregnan-20-one maintenance dose.

In another aspect, the oral pharmaceutical compositions or dosage forms may be administered with or without food, such as a meal, a snack, an appetizer, or a drink. In one example, administration without food may be during a fasting period of the subject. Food may include various forms of food including food having no fat and no calorie; no fat and low calorie; no fat and medium calorie; no fat and high calorie; low fat and low calorie; low fat and medium calorie; low fat and high calorie; medium fat and low calorie; medium fat and medium calorie; medium fat and high calorie; high fat and low calorie; high fat and medium calorie; and high fat and high calorie. In one aspect, administration with food may be any of an administration: without high-fat food; with a meal with at least about 5% calories from fat; with a meal with less than about 20% calories from fat; with a meal having from about 20% to about 35% calorie content from fat; and with a meal having from about 35% to about 60% calorie content from fat. The amount of fat and calories may be categorized via the regulations for foods under the Federal Food, Drug, and Cosmetic Act and its amendments.

Methods

In one embodiment, a method for ameliorating a symptom of a CNS or neuropsychiatric and neurodegenerative disorder in a subject comprises orally administering to the subject any of an effective amount of 3α-OH-5β-pregnan-20-one, a pharmaceutically acceptable salt thereof, an isomer thereof, and a combination thereof. In another aspect, a method for ameliorating a symptom of a CNS or neuropsychiatric and neurodegenerative disorder in a subject comprise orally administering to the subject a composition comprising any of an amount of oral 3α-OH-5β-pregnan-20-one, a pharmaceutically acceptable salt thereof, an isomer thereof, and a combination thereof that may be greater than about any of 3%, 4%, 5%, 6%, 7%, 8%, 9%, 10%, 11%, 12%, 13%, 14%, and 15% bioavailability relative to an equivalent dose of 3α-OH-5β-pregnan-20-one administered by IV infusion.

In one embodiment, a method of treating a CNS disorder comprises orally administering to a subject a pharmaceutical composition comprising 3α-OH-5β-pregnan-20-one and a plurality of additives so as to provide an increased serum $C_{max}$ level of 3α-OH-5β-pregnan-20-one, an increased serum $C_{avg}$ level of 3α-OH-5β-pregnan-20-one, or both in the subject, wherein the noted increases are greater than like increases obtained from administering to the subject a substantially equivalent amount of at least one of: a 3α-OH-5β-pregnan-20-one in SBE-β-CD solution composition (a cyclodextrin administration), a 3α-OH-5β-pregnan-20-one in a solution consisting essentially of a medium chain triglyceride (MCT) composition (an MCT administration), a 3α-OH-5β-pregnan-20-one in a solution consisting essentially of a polysorbate 80 suspension composition (a polysorbate 80 administration), and a 3α-OH-5β-pregnan-20-one in a solution consisting essentially of canola oil or peanut oil composition (an edible oil administration).

In another aspect, the 3α-OH-5β-pregnan-20-one may be in a form that increases serum levels of 3α-OH-5β-pregnan-20-one in a subject wherein the increased serum levels are greater than the serum levels obtained by administering to the subject a substantially equivalent amount of at least one of: a 3α-OH-5β-pregnan-20-one in SBE-β cyclodextrin solution composition (a cyclodextrin administration), a 3α-OH-5β-pregnan-20-one in a solution consisting essentially of a medium chain triglyceride (MCT) composition (an MCT administration), a 3α-OH-5β-pregnan-20-one in a solution consisting essentially of a polysorbate-80 suspension composition (a polysorbate 80 administration), and a 3α-OH-5β-pregnan-20-one in a solution consisting essentially of canola oil or peanut oil composition (an edible oil administration). In one example, the increased serum levels of 3α-OH-5β-pregnan-20-one may be increased by at least about 1.2× as compared to the serum levels obtained by administering to the subject a substantially equivalent amount of: a 3α-OH-5β-pregnan-20-one in a SBE-β cyclodextrin solution composition (a cyclodextrin administration), a 3α-OH-5β-pregnan-20-one in a solution consisting essentially of a medium chain triglyceride (MCT) composition (an MCT administration), a 3α-OH-5β-pregnan-20-one in a solution consisting essentially of a polysorbate-80 suspension composition (a polysorbate 80 administration), and a 3α-OH-5β-pregnan-20-one in a solution consisting essentially of canola oil or peanut oil composition (an edible oil administration).

In one aspect, the CNS disorder may be any one or more of: sleep disorders (e.g., insomnia), mood disorders (e.g., depression such as PND, major depressive disorder, PPD, essential tremor, treatment resistant depression, or perinatal depression), dysthymic disorder (e.g., mild depression), bipolar disorder (e.g., I and/or II), anxiety disorders (e.g., generalized anxiety disorder (GAD), social anxiety disorder), stress, post-traumatic stress disorder (PTSD), compulsive disorders (e.g., obsessive compulsive disorder (OCD)), schizophrenia spectrum disorders (e.g., schizophrenia, schizoaffective disorder), convulsive disorders (e.g., epilepsy, status epilepticus (SE)), seizures), disorders of memory and/or cognition (e.g., attention disorders, attention deficit hyperactivity disorder (ADHD)), dementia (e.g., Alzheimer's type dementia, Lewis body type dementia, vascular type dementia), movement disorders (e.g., Huntington's disease, Parkinson's disease), personality disorders (e.g., anti-social personality disorder, obsessive compulsive personality disorder), autism spectrum disorders (ASD) (e.g., autism, monogenetic causes of autism such as synaptopathy, Rett syndrome, Fragile X syndrome, Angelman syndrome), pain (e.g., neuropathic pain, injury related pain syndromes, acute pain, chronic pain), traumatic brain injury (TBI), vascular diseases (e.g., stroke, ischemia, vascular malformations), substance abuse disorders and/or withdrawal syndromes (e.g., addition to opiates, cocaine, and/or alcohol), tinnitus and combinations thereof.

In another embodiment, the disclosed method of treating a CNS disorder may include orally administering to a subject an amount of 3α-OH-5β-pregnan-20-one sufficient to enable the binding of GABAA receptors in the subject such that the CNS disorder of the subject is substantially reduced or eliminated.

In an embodiment of the invention, the disclosed method comprises orally administering to a subject a composition having orally bioavailable 3α-OH-5β-pregnan-20-one therein, wherein the subject has at least one of: an acute CNS disorder, an episodic CNS disorder, an intermittent CNS disorder, a sub-chronic CNS disorder, a chronic CNS disorder, and combinations thereof. When the CNS disorder is sub-chronic or chronic, the dosage regimen may range from at least once per day for a specified duration of from about a single day to about 3 months, or for more than 3 months.

In an embodiment of the invention, the subject in need of an oral composition comprising orally bioavailable 3α-OH-5β-pregnan-20-one may have a CNS disorder such as a depression disorder (e.g., PPD, postpartum substance addiction disorder, major depressive disorder, treatment resistant depression, perinatal depression, perimenopausal or postmenopausal depression).

In an embodiment of the invention, the disclosed compositions may be used for treatment, reduction, or elimination of conditions, symptoms, or diseases associated with CNS disorders to males or females. In one aspect, the subject may be an adolescent male or an adult male. In further aspects, the subject may be an adolescent female or an adult female. The adult female may be of childbearing age, pre-menopausal, perinatal, postpartum, pregnant, perimenopausal, or post-menopausal. In yet another aspect, the subject may be asymptomatic of a CNS disorder and yet may have a disease associated with a CNS disorder described herein.

An exemplary diagnosis of a clinical CNS disorder such as depression, may be for instance by assessing/performing at least one of the following rating scales/questionnaires or similar measures that include measuring severity of depression in individuals:

a. 17-Item Hamilton Rating Scale for Depression (HAM-D)

The HAM-D is a 17-item questionnaire used to diagnose depression, and as a guide to evaluate recovery and remission. The HAM-D is the most commonly used instrument for assessing symptoms of depression and is administered by a trained physician.

b. Montgomery-Asberg Depression Rating Scale for Depression (MADRS)

The MADRS is a clinician-rated scale used to examine the severity of depressive episodes in patients with mood disorders. It consists of a clinical interview of 10 items that moves from broad questions to more detailed ones.

c. Columbia-Suicide Severity Rating Scale (C-SSRS)

The C-SSRS is a suicidal ideation and behavior rating scale used to evaluate suicidality. The C-SSRS consists of a baseline assessment that evaluates the lifetime experiences of the subject with suicidal ideation and/or behavior, and a post-baseline evaluation that focuses on suicidal risk since the last visit.

d. Clinical Global Impression Scales for Severity (CGI-S) and Improvement (CGI-I)

The Clinical Global Impression Scale is a validated measure used in clinical research. It allows clinicians to integrate several sources of information into a single rating of the subject's condition.

e. The CGI-S

CGI-S is an objective measure of the severity of patient's illness at the time of assessment, relative to the clinician's past experience with patients who have the same diagnosis.

f. The CGI-I

CGI-I is a 7-item measure to assess the overall improvement of the patient's illness, relative to the subject's baseline condition.

g. Hamilton Rating Scale for Anxiety (HAM-A)

The HAM-A is a clinician-rated scale used to assess the severity of anxiety symptoms. The HAM-A consists of 14-items, each defined by a series of anxiety symptoms, both psychic and somatic.

h. Edinburgh Postnatal Depression Scale (EPDS)

The EPDS is a self-rated questionnaire used to identify PPD in outpatient, home visiting settings, or at the 6-8 week examination after delivery. The EPDS consists of 10 items that assess depressive symptoms such as feeling of guilt, low energy, anhedonia, sleep disturbance, and suicidal ideation.

i. Maternal Postnatal Attachment Scale (MPAS)

The MPAS is a self-rated questionnaire used to assess the mother-to-infant attachment. The MPAS consists of 19 items that evaluate the emotional bond between the mother and the infant.

j. The Center for Epidemiologic Studies Depression Scale (CES-D)

The CES-D is a 20-item measure that asks caregivers to rate how often over the past week they experienced symptoms associated with depression, such as restless sleep, poor appetite, and feeling lonely. The CES-D also provides cutoff scores (e.g., 16 or greater) that aid in identifying individuals at risk for clinical depression, with good sensitivity and specificity and high internal consistency.

k. The Beck Depression Inventory (BDI)

The BDI is a 21-item, self-report rating inventory that measures characteristic attitudes and symptoms of depression.

Clinical CNS activity may be assessed thru monitoring some of the CNS vital signs, such as composite memory, verbal memory, visual memory, psychomotor speed, reaction time, complex attention, cognitive flexibility, processing speed, executive function, non-verbal reasoning, social acuity, sustained attention, working memory, simple motor speed. Alternatively, CNS activity may also be assessed by monitoring occurrence of sleepiness, dry mouth, loss of consciousness, dizziness, somnolence, fatigue, hot flashes, pulse oximetry monitoring, and saccadic eye velocity measurements.

Neuropsychiatric or Neurodegenerative Diseases and Disorders

The methods described herein may be used for treating neuropsychiatric (see: Neuropsychiatry on Wikipedia's website) or neurodegenerative diseases and disorders. The term "neurodegenerative disease" includes diseases and disorders that are associated with the progressive loss of structure or function of neurons, or death of neurons. Neurodegenerative diseases and disorders include, but are not limited to, Alzheimer's disease (including the associated symptoms of mild, moderate, or severe cognitive impairment); amyotrophic lateral sclerosis (ALS); anoxic and ischemic injuries; ataxia and convulsion (including for the treatment and prevention of seizures that are caused by schizoaffective disorder or by drugs used to treat schizophrenia); benign forgetfulness; brain edema; cerebellar ataxia including McLeod neuroacanthocytosis syndrome (MLS) (see: Neuroacanthocytosis on the UpToDate, Inc. website of the Health division of Wolters Kluwer); closed brain injury; coma; contusive injuries (e.g., spinal cord injury and head injury); dementias including multi-infarct dementia and senile dementia; disturbances of consciousness; Down syndrome; drug-induced or medication-induced Parkinsonism (such as neuroleptic-induced acute akathisia, acute dystonia, Parkinsonism, or tardive dyskinesia, neuroleptic malignant syndrome, or medication-induced postural tremor); epilepsy; fragile X syndrome; Gilles de la Tourette's syndrome; head trauma; hearing impairment and loss; Huntington's disease; Lennox syndrome; levodopa-induced dyskinesia; mental retardation; movement disorders including akinesias and akinetic (rigid) syndromes (including basal ganglia calcification, corticobasal degeneration, multiple system atrophy, Parkinsonism-ALS dementia complex, Parkinson's disease, postencephalitic parkinsonism, and progressively supranuclear palsy); muscular spasms and disorders associated with muscular spasticity or weakness including chorea (such as benign hereditary chorea, drug-induced chorea, hemiballism, Huntington's disease, neuroacanthocytosis, Sydenham's chorea, and symptomatic chorea), dyskinesia (including tics such as complex tics, simple tics, and symptomatic tics), myoclonus (including generalized myoclonus and focal cycloclonus), tremor (such as rest tremor, postural tremor, and intention tremor) and dystonia (including axial dystonia, dystonic writer's cramp, hemiplegic dystonia, paroxysmal dystonia, and focal dystonia such as blepharospasm, oromandibular dystonia, and spasmodic dysphonia and torticollis); neuronal damage including ocular damage, retinopathy or macular degeneration of the eye; neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest; Parkinson's disease; seizure; status epilecticus; stroke; tinnitus; tubular sclerosis, and viral infection induced neurodegeneration (e.g., caused by acquired immunodeficiency syndrome (AIDS) and encephalopathies). Neurodegenerative diseases also include, but are not limited to, neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest.

Prevention and Treatment of Seizures and Epilepsy

A seizure (see: Clonic Seizures on the Epilepsy Foundation's website) is the physical findings or changes in behavior that occur after an episode of abnormal electrical activity in the brain. When seizures become a consistent problem, the condition is called epilepsy. The term "seizure" is often used interchangeably with "convulsion." Convulsions are defined by a person's body shaking rapidly and uncontrollably. During convulsions, a person's muscles contract and relax repeatedly. Based on the type of behavior and brain activity, seizures are divided into two broad categories, namely: generalized and partial (also called local or focal). Classifying the type of seizure helps a doctor diagnose whether or not a patient has epilepsy. Generalized seizures are produced by electrical impulses from throughout the entire brain, whereas partial seizures are produced (at least initially) by electrical impulses in a relatively small sub portion of the brain. The part of the brain that generates seizures is sometimes called the focus. There are six types of generalized seizures. The most common and dramatic, and therefore the most well-known, is the generalized convulsion, also called the grand mal (generalized tonic-clonic) seizure. In this type of seizure, the patient loses consciousness and usually collapses. The loss of consciousness is followed by generalized body stiffening (called the "tonic" phase of the seizure) for 30 to 60 seconds, then by violent jerking (the "clonic" phase) for 30 to 60 seconds, after which the patient goes into a deep sleep (the "postictal" or after-seizure phase). During grand mal seizures, injuries and accidents may occur, such as tongue biting and urinary incontinence. Absence seizures cause a short loss of consciousness gust a few seconds) with few or no symptoms. The patient, most often a child, typically interrupts an activity and stares blankly. These seizures begin and end abruptly and may occur several times a day. Patients are usually not aware that they are having a seizure, except that they may be aware of losing time. Myoclonic seizures consist of sporadic jerks, usually on both sides of the body. Patients sometimes describe the jerks as brief electrical shocks. When violent, these seizures may result in dropping or involuntarily throwing objects.

Clonic seizures are repetitive, rhythmic jerks that involve both sides of the body at the same time. Tonic seizures are characterized by stiffening of the muscles. Atonic seizures consist of a sudden and general loss of muscle tone, particularly in the arms and legs, which often results in a fall. Seizures with or without epilepsy described herein may include epileptic seizures, acute repetitive seizures, cluster seizures, continuous seizures; unremitting seizures, prolonged seizures, recurrent seizures, status epilepticus seizures, refractory convulsive status epilepticus seizures, non-convulsive status epilepticus seizures, refractory seizures, myoclonic seizures, tonic seizures, tonic-clonic seizures, simple partial seizures, complex partial seizures, secondarily generalized seizures, atypical absence seizures, absence seizures, childhood absence epilepsy (CAE), atonic seizures, benign Rolandic seizures, febrile seizures, emotional seizures, focal seizures, gelastic seizures, generalized onset seizures, infantile spasms, Jacksonian seizures, massive bilateral monooclonus seizures, multifocal seizures, neonatal onset seizures, nocturnal seizures, occipital lobe seizures, post traumatic seizures, subtle seizures, Sylvan seizures, visual reflex seizures, or withdrawal seizures. In some embodiments, the seizure is a generalized seizure associated with at least one of Dravet Syndrome, Lennox-Gastaut Syndrome, Tuberous Sclerosis Complex, CDLK5 disorder, Rett Syndrome or PCDH19 Female Pediatric Epilepsy. Juvenile myoclonic epilepsy (JME) is the most common generalized epilepsy syndrome.

Typically, epileptic patients need to take seizure medicine throughout their life as monotherapy or polytherapy with multiple agents to treat, prevent, reduce, or control seizures and epilepsies.

In one embodiment, methods of treating or preventing a neurodegenerative disease by orally administering the oral compositions comprising orally bioavailable 3α-OH-5β-pregnan-20-one also include treating or preventing loss of neuronal function characteristic of neurodegenerative disorder, such as status epilepticus (SE). Status epilepticus (SE) may include, convulsive status epilepticus, early status epilepticus, established status epilepticus, refractory status epilepticus, super-refractory status epilepticus, non-convulsive status epilepticus, generalized status epilepticus, complex partial status epilepticus, generalized periodic epileptiform discharges, and periodic lateralized epileptiform discharges. Convulsive status epilepticus is characterized by the presence of convulsive status epileptic seizures, and may include early status epilepticus, established status epilepticus, refractory status epilepticus, and super-refractory status epilepticus. Early status epilepticus is treated with a first line therapy. Established status epilepticus is characterized by status epileptic seizures which persist despite treatment with a first line therapy, and a second line therapy is administered. Refractory status epilepticus is characterized by status epileptic seizures which persist despite treatment with a first line and a second line therapy. Refractory status epilepticus is commonly treated with a general anesthetic. Super refractory status epilepticus is characterized by status epileptic seizures which persist despite treatment with a first line therapy, a second line therapy, and a general anesthetic for 24 hours or more.

Non-convulsive status epilepticus may include, focal non-convulsive status epilepticus, complex partial non-convulsive status epilepticus, simple partial non-convulsive status epilepticus, subtle non-convulsive status epilepticus; generalized non-convulsive status epilepticus, late onset absence non-convulsive status epilepticus, atypical absence non-convulsive status epilepticus, or typical absence non-convulsive status epilepticus.

In one embodiment, the pharmaceutically acceptable compositions and methods described herein may be administered as a monotherapy to a subject having at least one of traumatic brain injury epilepsy, status epilepticus, convulsive status epilepticus, early status epilepticus, established status epilepticus, refractory status epilepticus, super-refractory status epilepticus, non-convulsive status epilepticus, generalized status epilepticus, complex partial status epilepticus, seizure clusters, acute repetitive seizures, generalized periodic epileptiform discharges, and periodic lateralized epileptiform discharges, to treat, prevent, reduce, or improve seizures or epilepsies.

In another embodiment, the pharmaceutically acceptable compositions and methods described herein may be administered as a monotherapy to a subject having at least one of four classified epilepsies, which comprise focal epilepsy such as frontal lobe epilepsy, generalized epilepsy, combined generalized and focal epilepsy, simple or complex partial onset epilepsy, and unknown epilepsy (including neonatal and infantile epilepsies) as classified by the International League Against Epilepsy (ILAE) in 2017, to treat, prevent, reduce, or improve seizures or epilepsies.

In one aspect, the compositions and methods disclosed herein may be used to treat, prevent, reduce, or improve at least one of generalized epilepsies, comprising generalized tonic-clonic seizures (symptoms: loss of consciousness followed by body stiffening, then violent jerking after falling into a deep sleep), absence (or non-motor) seizures (symptoms: brief loss of consciousness), myoclonic seizures (symptoms: sporadic and brief jerking movements, usually on both sides of body), clonic seizures (symptoms: repetitive, rhythmic jerking movements on both sides of body at the same time), tonic seizures (symptoms: muscle stiffness and rigidity), and atonic seizures (symptoms: a sudden and general loss of muscle tone in arms and legs).

In another aspect, the compositions and methods disclosed herein may be used to treat, prevent, reduce, or improve at least one of focal epilepsies, comprising focal retained awareness seizures (motor/sensory/autonomic/psychological), focal impaired awareness seizures, focal motor seizures, focal non-motor seizures, focal to bilateral tonic-clonic seizures.

In a further aspect, the compositions and methods disclosed herein may be used to treat, prevent, reduce, or improve at least one of unknown (or idiopathic) epilepsies, comprising unknown motor seizures, unknown non-motor seizures, and unclassified seizures including neonatal and infantile seizures. Unknown seizures are defined as seizures that occur either in sleep or in a condition that cannot be described as the patient is alone or the witness cannot describe it. Unclassified seizures are so designated when a clinician is certain that the event is a seizure but cannot describe it due to incomplete information.

In one embodiment, the pharmaceutically acceptable compositions and methods described herein may be administered as an adjunctive therapy to a subject having at least one of traumatic brain injury epilepsy, status epilepticus, convulsive status epilepticus, early status epilepticus, established status epilepticus, refractory status epilepticus, super-refractory status epilepticus, non-convulsive status epilepticus, generalized status epilepticus, complex partial status epilepticus, generalized periodic epileptiform discharges, and periodic lateralized epileptiform discharges, to treat, prevent, reduce, or improve seizures or epilepsies.

In another embodiment, the pharmaceutically acceptable compositions and methods described herein may be administered as an adjunctive therapy to a subject having at least one of four classified epilepsies, which comprise focal epilepsy, generalized epilepsy, combined generalized and focal epilepsy, and unknown epilepsy, to treat, prevent, reduce, or improve seizures or epilepsies.

In one aspect, the pharmaceutically acceptable compositions and methods described herein may be administered as an adjunctive therapy with at least one of an anti-epileptic agent, such as bromide, phenobarbital, mephobarbital, phenytoin, acetazolamide, trimethadione, mephenytoin, paramethadione, corticosteroids, adrenocorticotropic hormone (ACTH), phenacemide, phensuximide, primidone, methsuximide, ethotoin, ethosuximide, chlordiazepoxide, sulthiame, diazepam, carbamazepine, valproate, clonazepam, clobazam, progabide, vigabatrin, zonisamide, lamotrigine, oxcarbazepine, felbamate, gabapentin, topiramate, tiagabine, levetiracetam, pregabalin, stiripentol, rufinamide, lacosamide, eslicarbazepine acetate, retigabine (ezogabine), perampanel, imepitoin, brivaracetam, everolimus, valproic acid, eslicarbazepine, cenobamate, fenfluramine, midazolam, and alprazolam, to treat, prevent, reduce, or improve seizures or epilepsies in subjects in need of therapy.

Research indicates that females have a marginally lower incidence of epilepsy and unprovoked (or reflex) seizures than males. This difference is usually attributed to male's greater exposure to risk factors for lesional epilepsy and acute symptomatic seizures. Idiopathic generalized epilepsies (IGEs), comprising about 15-20% of all epilepsies, are more common among females. Also, the behavior of some common epilepsy syndromes such as mesial temporal sclerosis may differ between genders with isolated auras more common among females and secondary seizure spread more likely in males. For example, the epilepsy trend between genders indicates that the incidence of status epilepticus, the incidence of sudden unexpected death in epilepsy (SUDEP), prognosis, and mortality are more common in men. For another example, boys with epilepsy with myoclonic-astatic seizures (Doose syndrome) suffer about two times more often than girls. Also, focal seizures with hyper-motor automatisms are about two times more prevalent in men than in women.

More women were diagnosed with idiopathic generalized epilepsy than men. No gender difference was found in localization-related epilepsy, but localization-related symptomatic epilepsies were more frequent in men, and cryptogenic localization-related epilepsies were more frequent in women.

There are epileptic syndromes that are more common in women such as pediatric absence epilepsy, typical early onset absence epilepsy, photosensitive forms of epilepsy, juvenile myoclonic epilepsy, and catamenial epilepsy.

Subjects who may be in need of the disclosed compositions and methods and for whom the disclosed compositions and methods may be of use include women of childbearing age (e.g. 12-49, 15-49, or 18-45 years of age). More specifically, the disclosed compositions and methods may be of particular usefulness for such women, who are capable of a nulliparous or multiparous (>1 year postpartum or previous delivery) planned or unplanned pregnancy, and more especially during the preconception phase, the pregnant phase, the labor phase, the peripartum phase, and the postpartum phase.

Women of the perimenopausal phase are defined as women in the period around menopause, ranging from about 39 to about 50 years of age (e.g., perimenopausal age may be 40 to 50 years of age).

Before the age of 10 years (including infantile and pediatric ages), pseudo-epileptic paroxysms are equally common in boys and girls. After 10 years (ages up to 18 years) pseudo-epileptic paroxysms are more common in girls. In adulthood (from ages of 18 years to about 70 years), women suffer from pseudo-epileptic paroxysms in 60-80% of epileptic cases. In the pubertal period and up to 30 years and over the age of 70 years, epilepsy is more common in women than in men. At puberty, young men are much more likely to work in their free time, and such work may lead to sleep deprivation and provoke epileptic seizures.

In one embodiment, the pharmaceutically acceptable compositions and methods described herein may be administered to childhood males or childhood females at ages of 5 to 17 years of age having at least one of traumatic brain injury epilepsy, status epilepticus, convulsive status epilepticus, early status epilepticus, established status epilepticus, refractory status epilepticus, super-refractory status epilepticus, non-convulsive status epilepticus, generalized status epilepticus, complex partial status epilepticus, generalized periodic epileptiform discharges, acute repetitive seizures, and periodic lateralized epileptiform discharges, to treat, prevent including breakthrough seizures, improve, or control seizures or epilepsies such subjects.

In another embodiment, the pharmaceutically acceptable compositions and methods described herein may be administered to childhood males or childhood females at ages of 5 to 17 years of age having at least one of four classified epilepsies, which comprises focal epilepsy, generalized epilepsy, combined generalized and focal epilepsy, and unknown epilepsy as classified by the International League Against Epilepsy (ILAE) in 2017, to treat seizures or epilepsies in such subjects.

In one embodiment, the pharmaceutically acceptable compositions and methods described herein may be administered to a male having at least one of traumatic brain injury epilepsy, status epilepticus, convulsive status epilepticus, early status epilepticus, established status epilepticus, refractory status epilepticus, super-refractory status epilepticus, non-convulsive status epilepticus, generalized status epilepticus, complex partial status epilepticus, generalized periodic epileptiform discharges, acute repetitive seizures, and periodic lateralized epileptiform discharges, to treat seizures or epilepsies.

In another embodiment, a pharmaceutically acceptable compositions and methods described herein may be administered to a male having at least one of four classified epilepsies, which comprise focal epilepsy, generalized epilepsy, combined generalized and focal epilepsy, and unknown epilepsy as classified by the International League Against Epilepsy (ILAE) in 2017, to treat seizures or epilepsies.

In adult men, either epilepsy or AEDs may cause dysfunction of the hypothalamic-pituitary-sexual system at all of its levels, which may result in sexual dysfunctions. Epileptic seizures are often associated with hormonal disorders, causing the release of hypothalamic and pituitary hormones. Also, some AEDs may alter the level of sex hormones, as well as induce their effects. Interictal increase of prolactin is observed in men and women with epilepsies, regardless of the anti-epileptic therapy that may be administered. An epileptic seizure may cause an increase in the level of prolactin, which reaches a maximum at short time (within ~1 hr) after the attack. In one aspect, the pharmaceutically acceptable compositions and methods described herein may be administered to a male with epilepsy having symptoms of sexual dysfunctions, to reduce, prevent, improve, or treat the epilepsy and/or its side effects, such as sexual dysfunction, increase of prolactin, increase of sex hormone binding globulin (SHBG), and decrease of free testosterone.

In one embodiment, the pharmaceutically acceptable compositions and methods described herein may be administered to a female having at least one of traumatic brain injury epilepsy, status epilepticus, convulsive status epilepticus, early status epilepticus, established status epilepticus, refractory status epilepticus, super-refractory status epilepticus, non-convulsive status epilepticus, generalized status epilepticus, complex partial status epilepticus, generalized periodic epileptiform discharges, acute repetitive seizures, and periodic lateralized epileptiform discharges, to treat seizures or epilepsies.

In another embodiment, the pharmaceutically acceptable compositions and methods described herein may be administered to a female having at least one of four classified epilepsies, which comprises focal epilepsy such as frontal lobe epilepsy, generalized epilepsy, combined generalized and focal epilepsy, and unknown epilepsy as classified by the International League Against Epilepsy (ILAE) in 2017, to treat seizures or epilepsies.

In one embodiment, the pharmaceutically acceptable compositions and methods described herein may be administered to menopausal or perimenopausal women with epilepsy or active epilepsy (controlled or uncontrolled seizures in the previous 6-12 months prior to the start of or adjunct to other AED(s) or monotherapy) to improve, control, prevent, prevent an increase, including breakthrough seizures, or treat seizures or epilepsy, and/or mood disorder, and/or sleep disorder.

In one embodiment, the pharmaceutically acceptable compositions and methods described herein may be administered to menopausal or perimenopausal women with a history of catamenial epilepsy or active epilepsy (controlled or uncontrolled seizures in the previous 6-12 months prior to the start of or adjunct to other AED(s) or monotherapy) to improve, control, prevent, prevent an increase, or treat seizures or epilepsy, and/or mood/disorder, and/or sleep disorder.

In one embodiment, the pharmaceutically acceptable compositions and methods described herein may be administered to menopausal or perimenopausal women with epilepsy or active epilepsy (controlled or uncontrolled seizures in the previous 6-12 months prior to the start of or adjunct to other AED(s) or monotherapy) and having endogenous positive allosteric neuroactive steroid deficiency, to improve, control, prevent, prevent an increase, or treat seizures or epilepsy, and/or mood disorder, and/or sleep disorder.

In one embodiment, the pharmaceutically acceptable compositions and methods described herein may be administered to menopausal or perimenopausal women or women of childbearing age on hormone replacement therapy with epilepsy or active epilepsy (controlled or uncontrolled seizures in the previous 6-12 months prior to the start of or adjunct to other AED(s) or monotherapy) and having endogenous positive allosteric modulator neuroactive steroid deficiency, to improve, control, prevent, prevent an increase, or treat seizures or epilepsy, and/or mood disorder, and/or sleep disorder.

In one embodiment, the pharmaceutically acceptable compositions and methods described herein may administered to menopausal or perimenopausal women or women of childbearing age with epilepsy or active epilepsy (controlled or uncontrolled seizures in the previous 6-12 months prior to the start of or adjunct to other AED(s) or monotherapy) and at risk of compromised bone health, to improve, control, prevent, prevent an increase, or treat seizures or epilepsy, and/or mood disorder, and/or sleep disorder.

In one embodiment, the pharmaceutically acceptable compositions and methods described herein may be administered to menopausal or perimenopausal women or women of childbearing age with epilepsy with at least 3 or more seizures per month just prior to start of or adjunct to other AED(s) or monotherapy, to improve, control, prevent, prevent an increase, or treat seizures or epilepsy, and/or mood disorder, and/or sleep disorder.

In one embodiment, the pharmaceutically acceptable compositions and methods described herein may be administered to menopausal or perimenopausal women or women of childbearing age with epilepsy with no greater than 25 seizure-free days in the last two months prior to start of or adjunct to other AED(s) or monotherapy, to improve, control, prevent, prevent an increase, or treat seizures or epilepsy, and/or mood disorder, and/or sleep disorder.

In one embodiment, the pharmaceutically acceptable compositions and methods described herein may be administered to women of childbearing age with epilepsy or active epilepsy just prior to start of or adjunct to other AED(s) or monotherapy, to improve, control, prevent, prevent an increase, or treat seizures or epilepsy, and/or mood disorder, and/or sleep disorder without regard to use of oral hormonal contraceptives.

In one embodiment, the pharmaceutically acceptable compositions and methods described herein may be administered to women of childbearing age with epilepsy or active epilepsy and have and having endogenous progesterone or positive allosteric modulator neuroactive steroid deficiency, or hyper testosterone or estrogen levels, just prior to start of or adjunct to other AED(s) or monotherapy, to improve, control, prevent, prevent an increase, or treat seizures or epilepsy, and/or mood disorder, and/or sleep disorder without regard to use of oral hormonal contraceptives.

In one embodiment, the pharmaceutically acceptable compositions and methods described herein may be administered to women of childbearing age with epilepsy or active epilepsy without regard to drug-drug interaction (DDI) compromising either contraception or seizure control efficacy of co-administered drugs, to improve, control, prevent, prevent an increase, or treat seizures or epilepsy, and/or mood disorder, and/or sleep disorder.

In one embodiment, the pharmaceutically acceptable compositions and methods described herein may be administered to women of childbearing age with epilepsy or active epilepsy and menses disorder, such as premenstrual syndrome, premenstrual dysphoric disorder (PMDD), and ovulation disorder, to improve, control, prevent, prevent an increase, or treat seizures or epilepsy, and/or mood disorder, and/or sleep disorder.

In one embodiment, the pharmaceutically acceptable compositions and methods described herein may be administered to women of childbearing age with epilepsy as an adjunct to other AED(s) to prevent breakthrough seizures or maintain seizure control as the AED dose is adjusted in women planning a pregnancy.

In one embodiment, the pharmaceutically acceptable compositions and methods described herein may be administered to women of childbearing age with epilepsy as an adjunct or monotherapy to other AED(s) to substitute all or substantial dosages of such AED(s) with teratogenic risk in women planning a pregnancy.

In one embodiment, a pharmaceutically acceptable compositions and methods described herein may be administered to women of childbearing age with epilepsy as an adjunct or monotherapy to other AED(s) to reduce or eliminate dependency on polypharmacy of such AED(s) for seizure control dosage in women planning a pregnancy.

In one embodiment, the pharmaceutically acceptable compositions and methods described herein may be administered to women of childbearing age with epilepsy as an adjunct or monotherapy to other AED(s) to reduce or eliminate dependency on polypharmacy of such AED(s) for seizure control dosage in women planning a pregnancy, by providing physiological levels of endogenous neuroactive steroids.

In one embodiment, the pharmaceutically acceptable compositions and methods described herein may be administered as an adjunct to other AED(s) or monotherapy to improve, control, prevent, prevent an increase, or treat at least one of seizure management, depression, anxiety, sleep impairment, and suicidal ideation, in a woman of childbearing age with epilepsy or active epilepsy, who is pregnant, planning to be pregnancy, or at risk of getting pregnant.

In one embodiment, the pharmaceutically acceptable compositions and methods described herein may be administered as an adjunct to other AED(s) without an increase in AED dosage or monotherapy to improve, control, prevent, prevent an increase, or treat at least one of seizure management, depression, anxiety, sleep impairment, and suicidal ideation, in a woman of childbearing age who is pregnant.

In one embodiment, the pharmaceutically acceptable compositions and methods described herein may be administered as an adjunct to other AED(s) or monotherapy to improve, control, prevent, prevent an increase, prevent an increase, or treat seizures management and at least one of an associated comorbid condition, such as depression, anxiety, sleep impairment, and suicidal ideation, in a woman of childbearing age with epilepsy or active epilepsy, who is pregnant, planning to be pregnancy, or at risk of getting pregnant.

In one aspect, the pharmaceutically acceptable compositions and methods described herein may be administered to a childbearing female having at least one of pediatric absence epilepsy, typical early onset absence epilepsy, photosensitive forms of epilepsy, juvenile myoclonic epilepsy, acute repetitive seizures, and catamenial epilepsy, to treat seizures, epilepsy, or related symptoms. In another aspect, the pharmaceutically acceptable compositions and methods described herein may be administered to a woman of childbearing age having catamenial epilepsy, comprising 1) epilepsy related to premenstrual withdrawal of the anticonvulsant effects of endogenous neuroactive steroids mediated through their action on GABAA receptors and related to alteration in GABAA receptor subunits and subsequent changes in neuronal inhibition, 2) estrogen peak in the day before ovulation, and 3) increased frequency of anovulatory cycles due to hypothalamic-pituitary-gonadal axis dysregulation and consequent low progesterone luteal phases, to treat seizures or epilepsies. Catamenial epilepsy patterns may be classified as three types by the time period in the menstrual cycle, namely: 1) Perimenstrual pattern (C1 pattern: related to decline of progesterone, day 25 to day 3), 2) Periovulatory pattern (C2 pattern: related to sudden increase of estrogen, day 10 to day 15), and 3) Luteal pattern (C3 pattern: related to inadequate luteal phase cycles by low progesterone levels resulting in anovulatory cycles, day 10 in one cycle to day 3 in next cycle). Premenstrual (or Perimenstrual) pattern or C1 pattern epilepsy is the most frequent type of epilepsy in childbearing female subjects with catamenial epilepsy.

In one aspect, the pharmaceutically acceptable compositions and methods described herein may be administered to a childbearing age female having at least one of perimenstrual pattern catamenial epilepsy, preovulatory pattern catamenial epilepsy, and luteal pattern catamenial epilepsy, to treat seizures or epilepsies.

In one embodiment, the pharmaceutically acceptable compositions and methods described herein may be administered to a postmenopausal or perimenopausal female having epilepsy related to low estrogen and low progesterone levels (a type of focal epilepsy), epilepsy not related to hormone levels (a type of generalized epilepsy), and unknown epilepsy, to treat seizures or epilepsies.

In one embodiment, the pharmaceutically acceptable compositions and methods described herein may be administered to a pregnant female having epilepsy, comprising focal epilepsy, generalized epilepsy, combined generalized and focal epilepsy, and unknown epilepsy, to treat seizures or epilepsies. For some pregnant women, particularly women who are sleep deprived or do not take medication as prescribed, pregnancy increases the frequency of seizures. In one aspect, the pharmaceutically acceptable compositions and methods described herein may be administered to a pregnant female having epilepsy, to treat symptoms or diseases caused by epilepsy during pregnancy, such as slowing of the fetal heart rate, decrease in oxygen to the fetus, fetal injury, premature separation of the placenta from the uterus (placental abruption), miscarriage due to trauma (e.g. a fall during a seizure), preterm labor, sudden infant death syndrome, breastfeeding difficulty, birth defects, and premature birth.

In one embodiment, the pharmaceutically acceptable compositions and methods described herein may be administered to a peripartum (late pregnancy and post-delivery) female having epilepsy or seizures comprising three types of seizures, namely: 1) the exacerbation of a known pre-existing seizure disorder, mainly epilepsy, 2) the new onset of seizures due to a non-pregnancy-related problem, and 3) seizures related to pregnancy conditions, to treat seizures or epilepsies. Seizures related to pregnancy have two categories, namely: i) focus on eclampsia, and ii) pregnancy-related new onset seizures, of which conditions include at least one of posterior reversible encephalopathy syndrome, reversible cerebral vasoconstriction syndrome, cerebral venous sinus thrombosis, thrombotic thrombocytopenic purpura, amniotic fluid embolism, and air embolism.

In general, in one embodiment, the oral compositions and methods of disclosed herein may be administered to treat CNS disorders (e.g. suicide ideation, depression, anxiety, bipolar disorder, essential tremor, neuropathic pain syndromes, trigeminal neuralgia, etc.) in women with epilepsy, to manage epilepsy during menses, pregnancy, or peripartum and postpartum in epileptic women of childbearing age, and to manage epilepsy in post or peri menopausal women.

In another embodiment, the oral compositions and methods of disclosed herein may be administered to treat CNS disorders (e.g. suicide ideation, depression, anxiety, bipolar disorder, essential tremor, neuropathic pain syndromes, trigeminal neuralgia, etc.) and to treat or manage epilepsy in adult epileptic men, childhood epileptic males, and childhood epileptic females.

Acute repetitive seizures (ARS) also known as cluster seizures, serial seizures, crescendo seizures, seizure flurries, recurrent seizures, and cyclical seizures. The frequency of ARS is typically more than 2 seizures in 24 hours, or in some cases more than 2 seizures in 6 to 8 hours. ARS has been associated with an evolution into status epilepticus. In one reported study, status epilepticus occurred more frequently in persons having cluster seizures than in people not having cluster seizures (40% versus 12%). Patients having cluster seizures have been shown to have higher death rates than those not having cluster seizures. The occurrence of frequent seizures in short periods of time is associated with an increased incidence of postictal psychosis, which may develop into chronic psychosis. People having cluster seizures are more frequently transported to emergency rooms and have more hospital admissions as compared to those who do not have cluster seizures.

There are unmet needs in developing therapy (compositions and methods) that may treat, stop, prevent, or control the evolution of ARS occurring at home, school, or work. The therapy may prevent transport to emergency rooms and hospital admission. ARS in such settings causes significant additional stress for the patient, family, and caregivers. Thus, ARS therapy will help decrease such stress and worry. ARS therapy that may be applied to patients at home, school, or work may offer a self-management tool and a greater degree of personal control. For parents of epileptic children, ARS therapies may provide increased confidence to allow their children to be unattended by health providers or caregivers, to permit activities outside the home such as school and afterschool activities, and to enable family trips away from home.

In one embodiment, the pharmaceutically acceptable compositions and methods described herein may be administered as a monotherapy to a subject having ARS to treat, prevent, reduce, or improve seizures or epilepsies.

In another embodiment, the pharmaceutically acceptable compositions and methods described herein may be administered as an adjunctive therapy to a subject having ARS to treat, prevent, reduce, or improve seizures or epilepsies.

In one aspect, the pharmaceutically acceptable compositions and methods described herein may be administered as an adjunctive therapy in combination with at least one of an anti-epileptic agents (such as bromide, phenobarbital, mephobarbital, phenytoin, acetazolamide, trimethadione, mephenytoin, paramethadione, corticosteroids, phenacemide, phensuximide, primidone, methsuximide, ethotoin, ethosuximide, chlordiazepoxide, sulthiame, diazepam, carbamazepine, valproate, clonazepam, clobazam, progabide, vigabatrin, zonisamide, lamotrigine, oxcarbazepine, felbamate, gabapentin, topiramate, tiagabine, levetiracetam, pregabalin, stiripentol, rufinamide, lacosamide, eslicarbazepine acetate, retigabine (ezogabine), perampanel, imepitoin, brivaracetam, everolimus, valproic acid, eslicarbazepine, cenobamate, fenfluramine, midazolam, and alprazolam) to treat, prevent, reduce, or improve ARS.

Also described herein are methods and compositions for treating a movement disorder. As used herein, the term "movement disorder" refers to a variety of diseases and disorders that are associated with hyperkinetic movement disorders and related abnormalities in muscle control. Exemplary movement disorders include, but are not limited to, Parkinson's disease and parkinsonism (defined particularly by bradykinesia), dystonia, chorea and Huntington's disease, ataxia, tremor (e.g., essential tremor), myoclonus and startle, tics and Tourette syndrome, Restless legs syndrome, stiff person syndrome, and gait disorders.

The methods and compositions described herein may be used to treat tremor such as cerebellar or intention tremor, dystonic tremor, essential tremor, orthostatic tremor, parkinsonian tremor, physiological tremor, psychogenic tremor, and rubral tremor. Tremor includes hereditary, degenerative, and idiopathic disorders such as Wilson' s disease, Parkinson' s disease, and essential tremor, respectively. Tremor may be caused by or associated with metabolic diseases (e.g. thyroid-parathyroid, liver, and hypoglycemia); peripheral neuropathies (associated with Charcot-Marie-Tooth, Roussy-Levy, diabetes mellitus, complex regional pain syndrome); toxins (e.g. nicotine, mercury, lead, CO, Manganese, arsenic, and toluene); select drugs (e.g. narcoleptics, tricyclics, lithium, cocaine, alcohol, adrenaline, bronchodilators, theophylline, caffeine, steroids, valproate, amiodarone, thyroid hormones, and vincristine); and psychogenic disorders. Clinical tremor may be classified into physiologic tremor, enhanced physiologic tremor, essential tremor syndromes (including classical essential tremor, primary orthostatic tremor, and task and position specific tremor), dystonic tremor, parkinsonian tremor, cerebellar tremor, Holmes' tremor (i.e., rubral tremor), palatal tremor, neuropathic tremor, toxic or drug-induced tremor, and psychogenic tremor. Tremor is an involuntary, at times rhythmic, muscle contraction and relaxation that may involve oscillations or twitching of one or more body parts (e.g., hands, arms, eyes, face, head, vocal folds (vocal cords), trunk, legs). Cerebellar tremor or intention tremor is a slow, broad tremor of the extremities that occurs after a purposeful movement. Cerebellar tremor is caused by lesions in or damage to the cerebellum resulting from, e.g., tumor, stroke, disease (e.g., multiple sclerosis, an inherited degenerative disorder). Dystonic tremor occurs in individuals affected by dystonia, a movement disorder in which sustained involuntary muscle contractions cause twisting and repetitive motions and/or painful and abnormal postures or positions. Dystonic tremor may affect any muscle in the body. Dystonic tremor occurs irregularly and often may be relieved by complete rest. Essential tremor or benign essential tremor is the most common type of tremor. Essential tremor may be mild and nonprogressive in some, and may be slowly progressive, starting on one side of the body but affect both sides within 3 years. The hands are most often affected, but the head, voice, tongue, legs, and trunk may also be involved. Tremor frequency may decrease as the person ages, but tremor severity may increase. Heightened emotion, stress, fever, physical exhaustion, or low blood sugar may trigger tremors and/or increase their severity. Symptoms generally evolve over time and may be both visible and persistent following onset.

Orthostatic tremor is characterized by fast (e.g., greater than 12 Hz) rhythmic muscle contractions that occurs in the legs and trunk immediately after standing. Cramps are felt in the thighs and legs and the patient may shake uncontrollably when asked to stand in one spot. Orthostatic tremor may occur in patients with essential tremor.

Parkinsonian tremor is caused by damage to structures within the brain that control movement. Parkinsonian tremor is often a precursor to Parkinson's disease and is typically seen as a "pill-rolling" action of the hands that may also affect the chin, lips, legs, and trunk. Onset of parkinsonian tremor typically begins after age 60. Movement starts in one limb or on one side of the body and may progress to include the other side.

Physiological tremor may occur in normal individuals and have no clinical significance. It may be seen in all voluntary muscle groups. Physiological tremor may be caused by certain drugs, alcohol withdrawal, or medical conditions including an overactive thyroid and hypoglycemia. Physiological tremor classically has a frequency of about 10 Hz.

Psychogenic tremor or hysterical tremor may occur at rest or during postural or kinetic movement. Patients with psychogenic tremor may have a conversion disorder or another psychiatric disease. Rubral tremor is characterized by coarse slow tremor which may be present at rest, at posture, and with intention. Rubral tremor is associated with conditions that affect the red nucleus in the midbrain, and classical unusual strokes.

Parkinson's disease affects nerve cells in the brain that produce dopamine. Symptoms include muscle rigidity, tremors, and changes in speech and gait. Parkinsonism is characterized by tremor, bradykinesia, rigidity, and postural instability. Parkinsonism shares symptoms found in Parkinson's disease but is a symptom complex rather than a progressive neurodegenerative disease. Dystonia is a movement disorder characterized by sustained or intermittent muscle contractions causing abnormal, often repetitive movements or postures. Dystonic movements may be patterned, twisting, and may be tremulous. Dystonia is often initiated or worsened by voluntary action and associated with overflow muscle activation.

Chorea is a neurological disorder characterized by jerky involuntary movements typically affecting the shoulders, hips, and face. Huntington's Disease is an inherited disease that causes nerve cells in the brain to waste away. Symptoms include uncontrolled movements, clumsiness, and balance problems. Huntington's disease may hinder walking, talking, and swallowing. Ataxia refers to the loss of full control of bodily movements, and may affect the fingers, hands, arms, legs, body, speech, and eye movements. Myloclonus and Startle is a response to a sudden and unexpected stimulus, which may be acoustic, tactile, visual, or vestibular.

Tics are an involuntary movement usually onset suddenly, brief, repetitive, but non-rhythmical, typically imitating normal behavior and often occurring out of a background of normal activity. Tics may be classified as motor or vocal. Motor tics are associated with movements while vocal tics are associated with sound. Tics may be characterized as simple or complex. For example, simple motor tics involve only a few muscles restricted to a specific body part. Tourette Syndrome is an inherited neuropsychiatric and neurodegenerative disorder with onset in childhood, characterized by multiple motor tics and at least one vocal tic.

Restless Legs Syndrome is a neurologic sensorimotor disorder characterized by an overwhelming urge to move the legs when at rest. Stiff Person Syndrome is a progressive movement disorder characterized by involuntary painful spasms and rigidity of muscles, usually involving the lower back and legs. Stiff Person Syndrome typically manifests in a stiff-legged gait with an exaggerated lumbar hyperlordosis. Characteristic abnormality on EMG recordings with continuous motor unit activity of the paraspinal axial muscles is also typically observed. Variants include "stiff-limb syndrome" producing focal stiffness typically affecting distal legs and feet.

Gait disorders refer to an abnormality in the manner or style of walking, which results from neuromuscular, arthritic, or other body changes. Gait is classified according to the system responsible for abnormal locomotion, and include hemiplegic gait, diplegic gait, neuropathic gait, myopathic gait, parkinsonian gait, choreiform gait, ataxic gait, and sensory gait.

Also provided herein are compositions and methods for treating a mood disorder. For example, mood disorders comprise clinical depression, postnatal depression or PPD, perinatal depression, atypical depression, melancholic depression, psychotic major depression, catatonic depression, seasonal affective disorder, dysthymia, double depression, depressive personality disorder, recurrent brief depression, minor depressive disorder, bipolar disorder or manic depressive disorder, depression caused by chronic medical conditions, treatment-resistant depression, refractory depression, suicidality, suicidal ideation, and suicidal behavior. In some embodiments, the compositions and methods described herein provide therapeutic effect to a subject suffering from depression (e.g., moderate or severe depression). In some embodiments, the mood disorder is associated with a disease or disorder described herein (e.g., neuroendocrine diseases and disorders, neurodegenerative diseases and disorders (e.g., epilepsy), movement disorders, tremor (e.g., Parkinson's Disease), women's health disorders or conditions).

Clinical depression is also known as major depression, major depressive disorder (MDD), severe depression, unipolar depression, unipolar disorder, and recurrent depression, and refers to a mental disorder characterized by pervasive and persistent low mood that is accompanied by low self-esteem and loss of interest or pleasure in normally enjoyable activities. Some people with clinical depression have trouble sleeping, lose weight, and generally feel agitated and irritable. Clinical depression affects how an individual feels, thinks, and behaves and may lead to a variety of emotional and physical problems. Individuals with clinical depression may have trouble doing day-to-day activities and clinical depression may make an individual feel as if life is not worth living.

Peripartum depression refers to depression in pregnancy. Symptoms include irritability, crying, feeling restless, trouble sleeping, extreme exhaustion (emotional and/or physical), changes in appetite, difficulty focusing, increased anxiety and/or worry, disconnected feeling from baby and/or fetus, and loss of interest in formerly pleasurable activities.

Postnatal depression (PND) is also referred to as PPD and refers to a type of clinical depression that affects women after childbirth. Symptoms may include sadness, fatigue, changes in sleeping and eating habits, reduced sexual desire, crying episodes, anxiety, and irritability. In some embodiments, PND is a treatment-resistant depression (e.g., a treatment-resistant depression as described herein). In some embodiments, PND is refractory depression (e.g., a refractory depression as described herein). In some embodiments, a subject having PND also experienced depression, or a symptom of depression during pregnancy. This depression is referred to herein as) perinatal depression. In an embodiment, a subject experiencing perinatal depression is at increased risk of experiencing PND.

Atypical depression (AD) is characterized by mood reactivity (e.g., paradoxical anhedonia) and positivity, significant weight gain, or increased appetite. Patients suffering from AD also may have excessive sleep or somnolence (hypersomnia), a sensation of limb heaviness, and significant social impairment as a consequence of hypersensitivity to perceived interpersonal rejection.

Melancholic depression is characterized by loss of pleasure (anhedonia) in most or all activities, failures to react to pleasurable stimuli, depressed mood more pronounced than that of grief or loss, excessive weight loss, or excessive guilt. Psychotic major depression (PMD) or psychotic depression refers to a major depressive episode, in particular of melancholic nature, where the individual experiences psychotic symptoms such as delusions and hallucinations. Catatonic depression refers to major depression involving disturbances of motor behavior and other symptoms. An individual may become mute and stuporous, and either is immobile or exhibits purposeless or bizarre movements.

Seasonal affective disorder (SAD) refers to a type of seasonal depression wherein an individual has seasonal patterns of depressive episodes coming on in the fall or winter.

Dysthymia refers to a condition related to unipolar depression, where the same physical and cognitive problems are evident. Such problems are not severe and tend to last longer (e.g., at least 2 years). Double depression refers to fairly depressed mood (dysthymia) that lasts for at least 2 years and is punctuated by periods of major depression. Depressive Personality Disorder (DPD) refers to a personality disorder with depressive features. Recurrent Brief Depression (RBD) refers to a condition in which individuals have depressive episodes about once per month, with each episode lasting 2 weeks or less and typically less than 2-3 days.

Minor depressive disorder or minor depression refers to a depression in which at least 2 symptoms are present for 2 weeks. Bipolar disorder or manic-depressive disorder causes extreme mood swings that include emotional highs (mania or hypomania) and lows (depression). During periods of mania the individual may feel or act abnormally happy, energetic, or irritable. They often make poorly thought-out decisions with little regard to the consequences. The need for sleep is usually reduced. During periods of depression there may be crying, poor eye contact with others, and a negative outlook on life. The risk of suicide among those with the disorder is high at greater than 6% over 20 years, while self-harm occurs in 30-40%. Other mental health issues such as anxiety disorder and substance use disorder are commonly associated with bipolar disorder. Depression caused by chronic medical conditions refers to depression caused by chronic medical conditions such as cancer or chronic pain, chemotherapy, and chronic stress. Treatment-resistant depression refers to a condition where the individuals have been treated for depression, but the symptoms do not improve. For example, antidepressants or psychological counseling (psychotherapy) do not ease depression symptoms for individuals with treatment-resistant depression. In some cases, individuals with treatment-resistant depression have improvement in symptoms, but the symptoms typically return. Refractory depression occurs in patients suffering from depression who are resistant to standard pharmacological treatments, including tricyclic antidepressants, MAOIs, SSRIs, and double and triple uptake inhibitors and/or anxiolytic drugs, as well as non-pharmacological treatments (e.g., psychotherapy, electroconvulsive therapy, vagus nerve stimulation and/or transcranial magnetic stimulation).

Post-surgical depression refers to feelings of depression that follow a surgical procedure (e.g., as a result of having to confront one's mortality). For example, individuals may feel sadness or empty mood persistently, a loss of pleasure or interest in hobbies and activities normally enjoyed, or a persistent felling of worthlessness or hopelessness. Mood disorder associated with conditions or disorders of women's health refers to mood disorders (e.g., depression) associated with (e.g., resulting from) a condition or disorder of women's health (e.g., as described herein). Suicidality, suicidal ideation, suicidal behavior refers to the tendency of an individual to commit suicide. Suicidal ideation concerns thoughts about or an unusual preoccupation with suicide. The range of suicidal ideation varies greatly, such as from fleeting thoughts to extensive thoughts, detailed planning, role playing, and incomplete attempts. Symptoms include talking about suicide, getting the means to commit suicide, withdrawing from social contact, being preoccupied with death, feeling trapped or hopeless about a situation, increasing use of alcohol or drugs, doing risky or self-destructive things, and saying goodbye to people as if they won't be seen again. Symptoms of depression include persistent anxious or sad feelings, feelings of helplessness, hopelessness, pessimism, worthlessness, low energy, restlessness, difficulty sleeping, sleeplessness, irritability, fatigue, motor challenges, loss of interest in pleasurable activities or hobbies, loss of concentration, loss of energy, poor self-esteem, absence of positive thoughts or plans, excessive sleeping, overeating, appetite loss, insomnia, self-harm, thoughts of suicide, and suicide attempts. The presence, severity, frequency, and duration of symptoms may vary on a case-to-case basis. Symptoms of depression, and relief of the same, may be ascertained by a physician or psychologist (e.g., by a mental state examination).

Anxiety Disorders: Provided herein are compositions and methods for treating anxiety disorders (e.g., generalized anxiety disorder, panic disorder, obsessive compulsive disorder, phobia, post-traumatic stress disorder). Anxiety disorder is a blanket term covering several different forms of abnormal and pathological fear and anxiety. Current psychiatric diagnostic criteria recognize a wide variety of anxiety disorders.

Generalized anxiety disorder is a common chronic disorder characterized by long-lasting anxiety that is not focused on any one object or situation. Those suffering from generalized anxiety experience non-specific persistent fear and worry and become overly concerned with everyday matters. Generalized anxiety disorder is the most common anxiety disorder to affect older adults.

In panic disorder, a person suffers from brief attacks of intense terror and apprehension, often marked by trembling, shaking, confusion, dizziness, nausea, and difficulty breathing. Such panic attacks, defined by the APA as fear or discomfort that abruptly arises and peaks in less than ten minutes, may last for several hours and may be triggered by stress, fear, or even exercise; although the specific cause is not always apparent. In addition to recurrent unexpected panic attacks, a diagnosis of panic disorder also requires that the attacks have chronic consequences, namely: either worry over the attack's potential implications, persistent fear of future attacks, or significant changes in behavior related to the attacks. Accordingly, those suffering from panic disorder experience symptoms even outside of specific panic episodes. Often, normal changes in heartbeat are noticed by a panic sufferer, leading them to think that something is wrong with their heart or that they are about to have another panic attack. In some cases, a heightened awareness (hypervigilance) of body functioning occurs during panic attacks, wherein any perceived physiological change is interpreted as a possible life threatening illness (i.e. extreme hypochondriasis).

Obsessive compulsive disorder (OCD) is a type of anxiety disorder primarily characterized by repetitive obsessions (distressing, persistent, and intrusive thoughts or images) and compulsions (urges to perform specific acts or rituals). The OCD thought pattern may be likened to superstitions insofar as it involves a belief in a causative relationship where, in reality, one does not exist. Often the process is entirely illogical; for example, the compulsion of walking in a certain pattern may be employed to alleviate the obsession of impending harm. And in many cases, the compulsion is entirely inexplicable and is simply an urge to complete a ritual triggered by nervousness. In a minority of cases, sufferers of OCD may only experience obsessions, with no overt compulsions; and a much smaller number of sufferers experience only compulsions.

The single largest category of anxiety disorders is that of phobia, which includes all cases in which fear and anxiety are triggered by a specific stimulus or situation. Sufferers typically anticipate terrifying consequences from encountering the object of their fear, which may be anything from an animal to a location to a bodily fluid.

Post-traumatic stress disorder (PTSD) is an anxiety disorder which results from a traumatic experience. Post-traumatic stress may result from an extreme situation, such as combat, rape, hostage situations, or even serious accident. It may also result from long term (chronic) exposure to a severe stressor, for example soldiers who endure individual battles but cannot cope with continuous combat. Common symptoms include flashbacks, avoidant behaviors, and depression.

Women's Health Disorders: Provided herein are compositions and methods for treating conditions or disorders related to women's health. Conditions or disorders related to women's health include, but are not limited to, Gynecological health and disorders (e.g., premenstrual syndrome (PMS), premenstrual dysphoric disorder (PMDD)), pregnancy issues (e.g., miscarriage, abortion), infertility and related disorders (e.g., polycystic ovary syndrome (PCOS)), other disorders and conditions, and issues related to women's overall health and wellness (e.g., menopause). Gynecological health and disorders affecting women include menstruation and menstrual irregularities; urinary tract health, including urinary incontinence and pelvic floor disorders; and such disorders as bacterial vaginosis, vaginitis, uterine fibroids, and vulvodynia.

Premenstrual syndrome (PMS) refers to physical and emotional symptoms that occur in the one to two weeks before a women's period. Symptoms vary but may include bleeding, mood swings, tender breasts, food cravings, fatigue, irritability, acne, and depression.

Premenstrual dysphoric disorder (PMDD) is a severe form of PMS. The symptoms of PMDD are similar to PMS but more severe and may interfere with work, social activity, and relationships. PMDD symptoms include mood swings, depressed mood or feelings of hopelessness, marked anger, increased interpersonal conflicts, tension and anxiety, irritability, decreased interest in usual activities, difficulty concentrating, fatigue, change in appetite, feeling out of control or overwhelmed, sleep problems, and physical problems (e.g., bloating, breast tenderness, swelling, headaches, joint or muscle pain).

Pregnancy issues include preconception care and prenatal care, pregnancy loss (miscarriage and stillbirth), preterm labor and premature birth, sudden infant death syndrome (SIDS), breastfeeding, and birth defects.

Miscarriage refers to a pregnancy that ends on its own, within the first 20 weeks of gestation. Abortion refers to the deliberate termination of a pregnancy, which may be performed during the first 28 weeks of pregnancy.

Infertility and related disorders include uterine fibroids, polycystic ovary syndrome, endometriosis, and primary ovarian insufficiency. Polycystic ovary syndrome (PCOS) refers to an endocrine system disorder among women of reproductive age. PCOS is a set of symptoms resulting from an elevated male hormone in women. Most women with PCOS grow many small cysts on their ovaries. Symptoms of PCOS include irregular or no menstrual periods, heavy periods, excess body and facial hair, acne, pelvic pain, difficulty getting pregnant, and patches of thick, darker, velvety skin. PCOS may be associated with conditions including type 2 diabetes, obesity, obstructive sleep apnea, heart disease, mood disorders, and endometrial cancer. Other disorders and conditions that affect only women include Turner syndrome, Rett syndrome, and ovarian and cervical cancers. Issues related to women's overall health and wellness include violence against women, women with disabilities and their unique challenges, osteoporosis and bone health, and menopause.

Menopause refers to the 12 months after a woman's last menstrual period and marks the end of menstrual cycles. Menopause typically occurs in a woman's 40s or 50s. Physical symptoms such as hot flashes and emotional symptoms of menopause may disrupt sleep, lower energy, or trigger anxiety or feelings of sadness or loss. Menopause includes neutral menopause and surgical menopause, which is a type of induced menopause due to an event such as surgery (e.g., hysterectomy, oophorectomy; and cancer). It is induced when the ovaries are gravely damaged by, e.g., radiation, chemotherapy, or other medications.

EXAMPLES

The following examples are provided to promote a clearer understanding of certain embodiments of the present invention and are in no way meant as a limitation thereon.

Example 1. Oral Pharmaceutical Compositions Comprising 3α-OH-5β-pregnan-20-one The oral pharmaceutical composition examples in the following are provided to promote a clear understanding of certain embodiments of the present invention related to treatment for a subject (a female and/or a male) in need of the therapy for CNS disorders and are in no way meant as a limitation thereon.

The following tables (Table A-Table C8) display oral compositions or dosage forms comprising 3α-OH-5β-pregnan-20-one in a form that comprises at least one form of solubilized, partially solubilized, dissolved, partially dissolved, amorphous solid, solid dispersion, solid solution, and eutectic mixture.

TABLE A

| Oral compositions comprising 3α-OH-5β-pregnan-20-one | | | | | | |
|---|---|---|---|---|---|---|
| | | Composition (w/w %) | | | | |
| | Ingredient | A1 | A2 | A3 | A4 | A5 |
| | 3α-OH-5β-pregnan-20-one | 31-40 | 15-30 | 10-14 | 5-9 | 0.5-5 |
| Additives | Tocopherol or its derivative, glyceryl fatty acid ester, polyglycerol fatty acid ester, triglyceride, propylene glycol fatty acid ester, fatty acid, edible oil, hydrogenated polyoxyl vegetable oil or glyceride, PEG glyceride of fatty acid ester, polyglycerol-10 fatty acid ester, polysorbate, vitamin E ester, sterols or its derivative, etc. | 50-69 | 70-85 | 84-90 | 91-95 | 95-99 |
| | Other ingredients* | q.s. | q.s. | q.s. | q.s. | q.s. |

*Other ingredients may comprise, but not limited to, co-solvent, anti-oxidant, permeation enhancer, stabilizer, plasticizer, solidifier, preservative, and so on. Hereafter it applies to all examples.

TABLE B

| Oral Compositions Comprising 3α-OH-5β-pregnan-20-one with at least One Lipophilic Additive and One Hydrophilic Additive | | | | | | |
|---|---|---|---|---|---|---|
| | | Composition (w/w %) | | | | |
| | Ingredient | B1 | B2 | B3 | B4 | B5 |
| | 3α-OH-5β-pregnan-20-one | 31-40 | 15-30 | 10-14 | 5-9 | 0.5-5 |
| Lipophilic additives | (e.g. vitamin E or its derivative, glyceryl fatty acid ester, polyglycerol fatty acid ester, triglyceride, propylene glycol fatty acid ester, fatty acid, edible oil, etc.) | 20-66 | 40-82 | 65-87 | 70-90 | 80-96 |
| Hydrophilic additives | (e.g. hydrogenated polyoxyl vegetable oil or glyceride, PEG glyceride of fatty acid ester, polyglycerol-10 fatty acid ester, polysorbate, vitamin E ester, sterols or its derivative, etc.) | 3-40 | 3-30 | 3-25 | 3-20 | 3-15 |
| | Other ingredients | q.s. | q.s. | q.s. | q.s. | q.s. |

TABLE C1

| Tocopherol-Comprising Oral Compositions | | | | | | | | | | | | | | | | |
|---|---|---|---|---|---|---|---|---|---|---|---|---|---|---|---|---|
| | | Alpha-tocopherol-comprising Composition C1 (w/w %) | | | | | | | | | | | | | | |
| | Ingredient | 1 | 2 | 3 | 4 | 5 | 6 | 7 | 8 | 9 | 10 | 11 | 12 | 13 | 14 | 15 |
| | 3α-OH-5β-pregnan-20-one | 11-16 | 6-10 | 4-7 | 7-10 | 5-8 | 6-9 | 4-7 | 4-7 | 4-7 | 5-8 | 5-8 | 8-11 | 9-12 | 4-7 | 4-7 |
| | Alpha-Tocopherol | 70-89 | 20-25 | 2-22 | 20-45 | 10-22 | 4-25 | 10-22 | 10-22 | 10-22 | 10-22 | 10-22 | 10-20 | 10-20 | 10-20 | 10-20 |
| | Glyceryl caprylate/caprate (e.g., CAPMUL MCM, CAPMUL 708G) | | | | 40-65 | 20-45 | | | | | | | | | | |
| | Glyceryl monocaprylate (e.g., CAPMUL MCM C8) | | 30-45 | | | | 30-85 | 20-45 | | | | | | | | |
| | Glyceryl monolinoleate (e.g., MAISINE) | | | | | | | | 20-45 | 20-45 | | | | | | |
| | Oleic acid | | | | | | | | | | 20-45 | 20-45 | | | | |
| | Peppermint oil | | | | | | | | | | | | 20-70 | 20-70 | | |
| | Castor oil | | | | | | | | | | | | | | 20-70 | 20-70 |
| Lipophilic additives† | Sorbitan oleate<br>Propylene glycol monolaurate<br>Linoleoyl polyoxyl-6 glycerides | | 3-6 | 5-25 | | 5-25 | 2-15 | 5-25 | | 5-25 | | 5-25 | | 5-25 | | 5-25 |
| Hydrophilic additives† | TPGS<br>DECAGLYCEROL MONO-/DI-OLEATE<br>CAPPRYLCAPROYL MACROGOL GLYCERIDES<br>POLYSORBATE 80<br>POLYOXYL 35 | | 10-30 | 25-50 | 5-30 | 5-25 | 5-50 | 5-25 | 25-50 | 5-25 | 25-50 | 5-25 | 25-50 | 5-25 | 25-50 | 5-25 |

TABLE C1-continued

| Tocopherol-Comprising Oral Compositions | | | | | | | | | | | | | | | |
|---|---|---|---|---|---|---|---|---|---|---|---|---|---|---|---|
| | Alpha-tocopherol-comprising Composition C1 (w/w %) | | | | | | | | | | | | | | |
| Ingredient | 1 | 2 | 3 | 4 | 5 | 6 | 7 | 8 | 9 | 10 | 11 | 12 | 13 | 14 | 15 |
| HYDROGENATED CASTOR OIL | | | | | | | | | | | | | | | |
| POLYOXYL 40 HYDROGENATED CASTOR OIL | | | | | | | | | | | | | | | |
| Other ingredients | q.s. | q.s. | q.s. | q.s. | q.s. | q.s. | q.s. | q.s. | q.s. | q.s. | q.s. | q.s. | q.s. | q.s. | q.s. |

†Lipophilic or hydrophilic additives may be selected at least one or a combination of, but not limited to, the ingredients shown in the table. Hereafter it applies to all examples.

TABLE C2

| Fatty Acid-Containing Oral Compositions | | | | | | | | | | | | | | | | |
|---|---|---|---|---|---|---|---|---|---|---|---|---|---|---|---|---|
| | | Fatty acid-containing Composition C2 (w/w %) | | | | | | | | | | | | | | |
| Ingredient | | 1 | 2 | 3 | 4 | 5 | 6 | 7 | 8 | 9 | 10 | 11 | 12 | 13 | 14 | 15 |
| 3α-OH-5β-pregnan-20-one | | 3-5 | 3-5 | 2-4 | 4-7 | 4-7 | 4-7 | 4-7 | 4-7 | 4-7 | 3-5 | 3-5 | 5-8 | 5-8 | 3-6 | 3-6 |
| Oleic acid | | 85-97 | 30-70 | 30-50 | 30-50 | 30-50 | 30-50 | 30-50 | 30-50 | 30-50 | 30-50 | 30-50 | 30-50 | 30-50 | 30-50 | 30-50 |
| Alpha-Tocopherol | | | | | 10-22 | 10-22 | | | | | | | | | | |
| Glyceryl caprylate/caprate (e.g., CAPMUL MCM, CAPMUL 708G) | | | | | | | 10-30 | 20-30 | | | | | | | | |
| Glyceryl monocaprylate (e.g., CAPMUL MCM C8) | | | | | | | | | 10-30 | 20-30 | | | | | | |
| Glyceryl monolinoleate (e.g., MAISINE) | | | | | | | | | | | 10-30 | 20-30 | | | | |
| Peppermint oil | | | | | | | | | | | | | 10-30 | 20-30 | | |
| Castor oil | | | | | | | | | | | | | | | 10-30 | 20-30 |
| Lipophilic additives | Sorbitan oleate<br>Propylene glycol monolaurate<br>Linoleoyl polyoxyl-6 glycerides | | 3-6 | 5-25 | | 5-25 | 2-15 | 5-25 | | 5-25 | | 5-25 | | 5-25 | | 5-25 |
| Hydrophilic additives | TPGS<br>DECAGLYCEROL MONO-/DI-OLEATE<br>CAPPRYLCAPROYL MACROGOL GLYCERIDES<br>POLYSORBATE 80<br>POLYOXYL 35 HYDROGENATED CASTOR OIL<br>POLYOXYL 40 HYDROGENATED CASTOR OIL | | 10-30 | 25-50 | 5-30 | 5-25 | 5-50 | 5-25 | 25-50 | 5-25 | 25-50 | 5-25 | 25-50 | 5-25 | 25-50 | 5-25 |
| Other ingredients | | q.s. | q.s. | q.s. | q.s. | q.s. | q.s. | q.s. | q.s. | q.s. | q.s. | q.s. | q.s. | q.s. | q.s. | q.s. |

TABLE C3

| Glyceryl Fatty Acid Ester-Containing Oral Compositions | | | | | | | | | | | | |
|---|---|---|---|---|---|---|---|---|---|---|---|---|
| | Glyceryl fatty acid ester-containing Composition C3 (w/w %) | | | | | | | | | | | |
| Ingredient | 1 | 2 | 3 | 4 | 5 | 6 | 7 | 8 | 9 | 10 | 11 | 12 |
| 3α-OH-5β-pregnan-20-one | 6-8 | 6-9 | 6-9 | 6-9 | 6-9 | 4-6 | 5-8 | 3-6 | 3-6 | 3-6 | 3-6 | 5-8 |
| Glyceryl caprylate/caprate (e.g., CAPMUL MCM, CAPMUL 708G) | 50-94 | | 40-70 | | | | 30-50 | | | 30-50 | 30-50 | |
| Glyceryl monocaprylate (e.g., CAPMUL MCM C8) | | 70-94 | | 40-70 | 40-70 | | | 30-50 | 30-50 | | | 30-50 |
| Alpha-Tocopherol | | | 10-22 | 10-22 | 10-22 | 10-22 | 10-22 | | | | | |
| Oleic acid | | | | | | | | | 20-30 | 20-30 | | |
| Glyceryl monolinoleate (e.g., MAISINE) | | | | | | 30-50 | | 20-30 | | | | |

TABLE C3-continued

| Glyceryl Fatty Acid Ester-Containing Oral Compositions | | | | | | | | | | | | | |
|---|---|---|---|---|---|---|---|---|---|---|---|---|---|
| | | Glyceryl fatty acid ester-containing Composition C3 (w/w %) | | | | | | | | | | | |
| | Ingredient | 1 | 2 | 3 | 4 | 5 | 6 | 7 | 8 | 9 | 10 | 11 | 12 |
| | Peppermint oil | | | | | | | | | | | | 20-35 |
| Lipophilic additives | Castor oil | | | | | | | | | | | 20-35 | |
| | Sorbitan oleate | | | | | 5-25 | 5-25 | 5-25 | | | 5-25 | 5-25 | |
| | Propylene glycol monolaurate | | | | | | | | | | | | |
| | Linoleoyl polyoxyl-6 glycerides | | | | | | | | | | | | |
| Hydrophilic additives | TPGS | 5-15 | 20-50 | 25-50 | 25-50 | 5-25 | 5-25 | 5-25 | 25-50 | 25-50 | 5-25 | 5-25 | 25-50 |
| | DECAGLYCEROL MONO-/DI-OLEATE | | | | | | | | | | | | |
| | CAPPRYLCAPROYL MACROGOL GLYCERIDES | | | | | | | | | | | | |
| | POLYSORBATE 80 | | | | | | | | | | | | |
| | POLYOXYL 35 HYDROGENATED CASTOR OIL | | | | | | | | | | | | |
| | POLYOXYL 40 HYDROGENATED CASTOR OIL | | | | | | | | | | | | |
| | Other ingredients | q.s. | q.s. | q.s. | q.s. | q.s. | q.s. | q.s. | q.s. | q.s. | q.s. | q.s. | q.s. |

TABLE C4

| PEG Glyceride of Fatty Acid Ester-Containing Oral Compositions | | | | | | | | | | | | | | | | |
|---|---|---|---|---|---|---|---|---|---|---|---|---|---|---|---|---|
| | | PEG glyceride of fatty acid ester-containing Composition C4 (w/w %) | | | | | | | | | | | | | | |
| | Ingredient | 1 | 2 | 3 | 4 | 5 | 6 | 7 | 8 | 9 | 10 | 11 | 12 | 13 | 14 | 15 |
| | 3α-OH-5β-pregnan-20-one | 2-4 | 2-4 | 3-5 | 2-4 | 3-5 | 4-6 | 4-6 | 3-5 | 3-5 | 2-4 | 2-4 | 3-6 | 3-6 | 2-5 | 2-5 |
| | PEG-6 mono/di-linoleate (e.g., Linoleoyl polyoxyl-6 glycerides) | 90-98 | 50-70 | 40-70 | 30-50 | 30-50 | 30-50 | 30-50 | 30-50 | 30-50 | 30-50 | 30-50 | 30-50 | 30-50 | 30-50 | 30-50 |
| | Oleic acid | | | | 25-40 | 10-25 | | | | | | | | | | |
| | Alpha-Tocopherol | | | | | | 10-22 | 10-22 | | | | | | | | |
| | Glyceryl caprylate/caprate (e.g., CAPMUL MCM, CAPMUL 708G) | | | | | | | | 20-30 | | | | | | | |
| | Glyceryl monocaprylate (e.g., CAPMUL MCM C8) | | | | | | | | | 20-30 | | | | | | |
| | Glyceryl monolinoleate (e.g., MAISINE) | | | | | | | | | | 20-30 | 20-30 | | | | |
| | Peppermint oil | | | | | | | | | | | | 20-30 | 20-30 | | |
| | Castor oil | | | | | | | | | | | | | | 20-30 | 20-30 |
| Lipophilic additives | Sorbitan oleate | | | 5-25 | | 5-25 | | 5-25 | | 5-25 | | 5-25 | | 5-25 | | 5-25 |
| | Propylene glycol monolaurate | | | | | | | | | | | | | | | |
| Hydrophilic additives | TPGS | | 25-50 | 5-25 | 25-50 | 5-25 | 25-50 | 5-25 | 25-50 | 5-25 | 25-50 | 5-25 | 25-50 | 5-25 | 25-50 | 5-25 |
| | DECAGLYCEROL MONO-/DI-OLEATE | | | | | | | | | | | | | | | |
| | CAPPRYLCAPROYL MACROGOL GLYCERIDES | | | | | | | | | | | | | | | |
| | POLYSORBATE 80 | | | | | | | | | | | | | | | |
| | POLYOXYL 35 HYDROGENATED CASTOR OIL | | | | | | | | | | | | | | | |
| | POLYOXYL 40 HYDROGENATED CASTOR OIL | | | | | | | | | | | | | | | |
| | Other ingredients | q.s. | q.s. | q.s. | q.s. | q.s. | q.s. | q.s. | q.s. | q.s. | q.s. | q.s. | q.s. | q.s. | q.s. | q.s. |

TABLE C5

Polyglycerol Fatty Acid Ester-Containing Oral Compositions

| | Ingredient | Polyglycerol fatty acid ester-containing Composition C5 (w/w %) | | | | | | | | | | | | | | |
|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 |
| | 3α-OH-5β-pregnan-20-one | 4-7 | 3-5 | 3-5 | 3-5 | 3-5 | 5-8 | 5-8 | 4-6 | 4-6 | 3-6 | 3-6 | 5-7 | 5-7 | 3-6 | 3-6 |
| | Polyglyceryl-10 mono/di-oleate (e.g., CAPROL PGE-860) | 90-96 | 50-70 | 40-70 | 30-50 | 30-50 | 30-50 | 30-50 | 30-50 | 30-50 | 30-50 | 30-50 | 30-50 | 30-50 | 30-50 | 30-50 |
| | Oleic acid | | | | 25-40 | 10-25 | | | | | | | | | | |
| | Alpha-Tocopherol | | | | | | 10-22 | 10-22 | | | | | | | | |
| | Glyceryl caprylate/caprate (e.g., CAPMUL MCM, CAPMUL 708G) | | | | | | | | 20-30 | | | | | | | |
| | Glyceryl monocaprylate (e.g., CAPMUL MCM C8) | | | | | | | | | 20-30 | | | | | | |
| | Glyceryl monolinoleate (e.g., MAISINE) | | | | | | | | | | 20-30 | 20-30 | | | | |
| | Peppermint oil | | | | | | | | | | | | 20-30 | 20-30 | | |
| | Castor oil | | | | | | | | | | | | | | 20-30 | 20-30 |
| Lipophilic additives | Sorbitan oleate | | | 5-25 | | 5-25 | | 5-25 | | 5-25 | | 5-25 | | 5-25 | | 5-25 |
| | Propylene glycol monolaurate | | | | | | | | | | | | | | | |
| | Labraphil M1944 CS | | | | | | | | | | | | | | | |
| Hydrophilic additives | TPGS | | 25-50 | 5-25 | 25-50 | 5-25 | 25-50 | 5-25 | 25-50 | 5-25 | 25-50 | 5-25 | 25-50 | 5-25 | 25-50 | 5-25 |
| | CAPPRYLCAPROYL MACROGOL GLYCERIDES | | | | | | | | | | | | | | | |
| | POLYSORBATE 80 | | | | | | | | | | | | | | | |
| | POLYOXYL 35 HYDROGENATED CASTOR OIL | | | | | | | | | | | | | | | |
| | POLYOXYL 40 HYDROGENATED CASTOR OIL | | | | | | | | | | | | | | | |
| | Other ingredients | q.s. | q.s. | q.s. | q.s. | q.s. | q.s. | q.s. | q.s. | q.s. | q.s. | q.s. | q.s. | q.s. | q.s. | q.s. |

TABLE C6

Triglyceride-Containing Oral Compositions

| | Ingredient | Triglyceride-containing Composition C6 (w/w %) | | | | | | | | | | | | | | |
|---|---|---|---|---|---|---|---|---|---|---|---|---|---|---|---|---|
| | | 1 | 2 | 3 | 4 | 5 | 6 | 7 | 8 | 9 | 12 | 13 | 14 | 15 | 16 | 17 |
| | 3α-OH-5β-pregnan-20-one | 3-6 | 3-5 | 3-5 | 3-5 | 3-5 | 4-7 | 4-7 | 3-6 | 3-6 | 3-5 | 3-5 | 4-7 | 4-7 | 3-5 | 3-5 |
| | Caprylic/Capric triglyceride (e.g., CAPTEX 300) | 84-92 | 50-70 | 40-70 | 30-50 | 30-50 | 30-50 | 30-50 | 30-50 | 30-50 | 30-50 | 30-50 | 30-50 | 30-50 | 30-50 | 30-50 |
| | Oleic acid | | | | 25-40 | 10-25 | | | | | | | | | | |
| | Alpha-Tocopherol | | | | | | 10-22 | 10-22 | | | | | | | | |
| | Glyceryl caprylate/caprate (e.g., CAPMUL MCM, CAPMUL 708G) | | | | | | | | 20-30 | | | | | | | |
| | Glyceryl monocaprylate (e.g., CAPMUL MCM C8) | | | | | | | | | 20-30 | | | | | | |
| | Glyceryl monolinoleate (e.g., MAISINE) | | | | | | | | | | 20-30 | 20-30 | | | | |
| | Peppermint oil | | | | | | | | | | | | 20-30 | 20-30 | | |
| | Castor oil | | | | | | | | | | | | | | 20-30 | 20-30 |
| Lipophilic additives | Sorbitan oleate | | | 5-25 | | 5-25 | | 5-25 | | 5-25 | | 5-25 | | 5-25 | | 5-25 |
| | Propylene glycol monolaurate | | | | | | | | | | | | | | | |
| | Labraphil M1944 CS | | | | | | | | | | | | | | | |
| Hydrophilic additives | TPGS | 5-25 | 25-50 | 5-25 | 25-50 | 5-25 | 25-50 | 5-25 | 25-50 | 5-25 | 25-50 | 5-25 | 25-50 | 5-25 | 25-50 | 5-25 |
| | DECAGLYCEROL MONO-/DI-OLEATE | | | | | | | | | | | | | | | |
| | CAPPRYLCAPROYL MACROGOL GLYCERIDES | | | | | | | | | | | | | | | |
| | POLYSORBATE 80 | | | | | | | | | | | | | | | |
| | POLYOXYL 35 | | | | | | | | | | | | | | | |

TABLE C6-continued

| Triglyceride-Containing Oral Compositions | | | | | | | | | | | | | | | |
|---|---|---|---|---|---|---|---|---|---|---|---|---|---|---|---|
| | Triglyceride-containing Composition C6 (w/w %) | | | | | | | | | | | | | | |
| Ingredient | 1 | 2 | 3 | 4 | 5 | 6 | 7 | 8 | 9 | 12 | 13 | 14 | 15 | 16 | 17 |
| HYDROGENATED CASTOR OIL | | | | | | | | | | | | | | | |
| POLYOXYL 40 HYDROGENATED CASTOR OIL | | | | | | | | | | | | | | | |
| Other ingredients | q.s. | q.s. | q.s. | q.s. | q.s. | q.s. | q.s. | q.s. | q.s. | q.s. | q.s. | q.s. | q.s. | q.s. | q.s. |

TABLE C7

| Propylene Glycol Fatty Acid Ester-Containing Oral Compositions | | | | | | | | | | | | | | | | |
|---|---|---|---|---|---|---|---|---|---|---|---|---|---|---|---|---|
| | | Propylene glycol fatty acid ester-containing Composition C7 (w/w %) | | | | | | | | | | | | | | |
| | Ingredient | 1 | 2 | 3 | 4 | 5 | 6 | 7 | 8 | 9 | 10 | 11 | 12 | 13 | 14 | 15 |
| | 3α-OH-5β-pregnan-20-one | 3-5 | 2-4 | 2-4 | 3-5 | 3-5 | 4-6 | 4-6 | 3-5 | 3-5 | 2-5 | 2-5 | 4-7 | 4-7 | 3-5 | 2-5 |
| | Propylene glycol monocaprylate (e.g., CAPMUL PG-8) | 90-97 | 50-70 | 40-70 | 30-50 | 30-50 | 30-50 | 30-50 | 30-50 | 30-50 | 30-50 | 30-50 | 30-50 | 30-50 | 30-50 | 30-50 |
| | Octanoic acid | | | | 25-40 | 10-25 | | | | | | | | | | |
| | Alpha-Tocopherol | | | | | | 10-22 | 10-22 | | | | | | | | |
| | Glyceryl caprylate/caprate (e.g., CAPMUL MCM, CAPMUL 708G) | | | | | | | | 20-30 | | | | | | | |
| | Glyceryl monocaprylate (e.g., CAPMUL MCM C8) | | | | | | | | | 20-30 | | | | | | |
| | Glyceryl monolinoleate (e.g., MAISINE) | | | | | | | | | | 20-30 | 20-30 | | | | |
| | Peppermint oil | | | | | | | | | | | | 20-30 | 20-30 | | |
| | Castor oil | | | | | | | | | | | | | | 20-30 | 20-30 |
| Lipophilic additives | Sorbitan oleate | | | 5-25 | | 5-25 | | 5-25 | | 5-25 | | 5-25 | | 5-25 | | 5-25 |
| | Propylene glycol monolaurate | | | | | | | | | | | | | | | |
| | Labraphil M1944 CS | | | | | | | | | | | | | | | |
| Hydrophilic additives | TPGS | | 25-50 | 5-25 | 25-50 | 5-25 | 25-50 | 5-25 | 25-50 | 5-25 | 25-50 | 5-25 | 25-50 | 5-25 | 25-50 | 5-25 |
| | DECAGLYCEROL MONO-/DI-OLEATE | | | | | | | | | | | | | | | |
| | CAPPRYLCAPROYL MACROGOL GLYCERIDES | | | | | | | | | | | | | | | |
| | POLYSORBATE 80 | | | | | | | | | | | | | | | |
| | POLYOXYL 35 HYDROGENATED CASTOR OIL | | | | | | | | | | | | | | | |
| | POLYOXYL 40 HYDROGENATED CASTOR OIL | | | | | | | | | | | | | | | |
| | Other ingredients | q.s. | q.s. | q.s. | q.s. | q.s. | q.s. | q.s. | q.s. | q.s. | q.s. | q.s. | q.s. | q.s. | q.s. | q.s. |

TABLE C8

| Edible Oil-Containing Oral Compositions | | | | | | | | | |
|---|---|---|---|---|---|---|---|---|---|
| | Edible oil-containing Composition C8 (w/w %) | | | | | | | | |
| Ingredient | 1 | 2 | 3 | 4 | 5 | 6 | 7 | 8 | 9 |
| 3α-OH-5β-pregnan-20-one | 10-14 | 8-11 | 6-8 | 8-12 | 7-10 | 6-9 | 6-9 | 3-5 | 3-5 |
| Peppermint oil | 80-90 | 40-80 | 30-60 | 20-50 | 20-50 | 20-50 | 20-50 | | |
| Castor oil | | | | | | | | 90-97 | 40-80 |
| Alpha-Tocopherol | | | | 10-22 | | | | | |
| Glyceryl caprylate/caprate (e.g., CAPMUL MCM, CAPMUL 708G) | | | | | | | | | |
| Glyceryl monocaprylate (e.g., CAPMUL MCM C8) | | | | | 20-40 | | | | |
| Glyceryl monolinoleate (e.g., MAISINE) | | | | | | 20-40 | | | |
| Propylene glycol monocaprylate (e.g., CAPMUL PG-8) | | | | | | | 20-40 | | |

TABLE C8-continued

| Edible Oil-Containing Oral Compositions | | | | | | | | | | |
|---|---|---|---|---|---|---|---|---|---|---|
| Lipophilic additives | Sorbitan oleate | | | 5-25 | | 5-25 | | 5-25 | | 5-25 |
| | Propylene glycol monolaurate | | | | | | | | | |
| | Labraphil M1944 CS | | | | | | | | | |
| Hydrophilic additives | TPGS | | 25-50 | 5-25 | 25-50 | 5-25 | 25-50 | 5-25 | | 5-25 |
| | DECAGLYCEROL MONO-/DI-OLEATE | | | | | | | | | |
| | CAPPRYLCAPROYL MACROGOL GLYCERIDES | | | | | | | | | |
| | POLYSORBATE 80 | | | | | | | | | |
| | POLYOXYL 35 HYDROGENATED CASTOR OIL | | | | | | | | | |
| | POLYOXYL 40 HYDROGENATED CASTOR OIL | | | | | | | | | |
| Other ingredients | | q.s. | q.s. | q.s. | q.s. | q.s. | q.s. | q.s. | q.s. | q.s. |

| | | Edible oil-containing Composition C8 (w/w %) | | | | | | |
|---|---|---|---|---|---|---|---|---|
| Ingredient | | 10 | 11 | 12 | 13 | 14 | 15 | 16 |
| 3α-OH-5β-pregnan-20-one | | 3-5 | 4-7 | 3-5 | 3-5 | 3-5 | 3-5 | 3-5 |
| Peppermint oil | | | | | | | | |
| Castor oil | | 30-60 | 20-50 | 20-50 | 20-50 | 20-50 | 20-50 | 20-50 |
| Alpha-Tocopherol | | | 10-22 | | | | | |
| Glyceryl caprylate/caprate (e.g., CAPMUL MCM, CAPMUL 708G) | | | | 20-40 | | | | |
| Glyceryl monocaprylate (e.g., CAPMUL MCM C8) | | | | | 20-40 | 5-20 | | |
| Glyceryl monolinoleate (e.g., MAISINE) | | | | | | | 20-40 | |
| Propylene glycol monocaprylate (e.g., CAPMUL PG-8) | | | | | | | | 20-40 |
| Lipophilic additives | Sorbitan oleate | | 5-25 | | 5-25 | | | 5-25 |
| | Propylene glycol monolaurate | | | | | | | |
| | Labraphil M1944 CS | | | | | | | |
| Hydrophilic additives | TPGS | 25-50 | 5-25 | 25-50 | 5-25 | 25-50 | 25-50 | 5-25 |
| | DECAGLYCEROL MONO-/DI-OLEATE | | | | | | | |
| | CAPPRYLCAPROYL MACROGOL GLYCERIDES | | | | | | | |
| | POLYSORBATE 80 | | | | | | | |
| | POLYOXYL 35 HYDROGENATED CASTOR OIL | | | | | | | |
| | POLYOXYL 40 HYDROGENATED CASTOR OIL | | | | | | | |
| Other ingredients | | q.s. | q.s. | q.s. | q.s. | q.s. | q.s. | q.s. |

The oral pharmaceutical composition comprising 3α-OH-5β-pregnan-20-one described herein may be formulated in a liquid (e.g., solution, suspension, emulsion, drink, etc.) or in encapsulated gelatin or non-gelatin capsule dosage forms known to those of skill in the art. The capsule may be a soft gelatin or non-gelatin capsule or a hard gelatin or non-gelatin capsule. The hard capsule may be a two-piece, standard capsule which typically includes a first capsule portion of bottom and a second capsule portion of top. The soft capsule may be a two-piece capsule wherein two portions are sealed together or a one-piece, hermetically sealed cap.

As shown in the below Tables D and E, the oral compositions or dosage forms of this invention may comprise frilly solubilized or noncrystalline forms (e.g. amorphous) of 3α-OH-5β-pregnan-20-one. The oral compositions of the present disclosure may be formulated to provide % release rates that may yield enhanced therapeutic levels of the 3α-OH-5β-pregnan-20-one for treatment of depression disorders. The in vitro percent release of 3α-OH-5β-pregnan-20-one from these oral compositions may be obtained by measuring the percent release of 3α-OH-5β-pregnan-20-one during a 4-hour exposure of the composition using a USP Type-II dissolution apparatus in 900 ml of deionized water with 0.5% (w/v) of sodium lauryl sulfate at 75 rpm at 37° C. and using an HPLC method.

TABLE D

Oral Compositions Comprising Noncrystalline Forms of 3α-OH-5β-pregnan-20-one

| | Composition D (w/w %) | | | | | | | | | | | | | |
|---|---|---|---|---|---|---|---|---|---|---|---|---|---|---|
| Component | 1 | 2 | 3 | 4 | 5 | 6 | 7 | 8 | 9 | 10 | 11 | 12 | 13 | 14 |
| 3α-OH-5β-pregnan-20-one | 6-9 | 6-9 | 5-8 | 7-10 | 6-9 | 6-9 | 6-9 | 5-8 | 5-8 | 2-4 | 5-7 | 9-12 | 5-8 | 8-11 |
| Glyceryl monocaprylate and/or caprylocaprylate | 80-85 | 45-54 | 40-45 | 60-68 | 53-58 | 43-48 | 60-68 | 45-55 | | | | | | |
| Propylene glycol monolaurate | | | | | | | | | 38-46 | 38-43 | | | | |
| Propylene glycol monocaprylate | | | 2-5 | | | | 6-10 | | | | 55-60 | | 13-18 | |
| Alpha-tocopherol | 0-5 | 10-22 | 10-22 | 10-22 | 10-22 | 10-22 | 0-5 | 0-5 | 20-40 | 2-5 | 10-22 | 20-37 | 10-22 | 30-50 |
| Peppermint oil | | | | | | | 8-12 | | | | | 42-50 | 28-35 | |
| TPGS | | | | | 6-10 | | | | | 22-28 | | | 13-18 | 5-10 |
| Hydrophilic surfactant (e.g., POLYOXYL 40 HYDROGENATED CASTOR OIL, POLYOXYL 35 HYDROGENATED CASTOR OIL) | 4-8 | 22-28 | 22-28 | 10-14 | 10-14 | 13-18 | 10-15 | 42-50 | 20-25 | 22-28 | 13-18 | 8-13 | 7-11 | 10-15 |
| Polyglyceryl-10 mono/di-oleate | | | | | | 15-20 | | | | | | | | 20-25 |
| Other ingredients | q.s. | q.s. | q.s. | q.s. | q.s. | q.s. | q.s. | q.s. | q.s. | q.s. | q.s. | q.s. | q.s. | q.s. |

TABLE E

Oral Dosage Forms Comprising Noncrystalline Forms of 3α-OH-5β-pregnan-20-one

| | Dosage form E (w/w %) | | | | | | | | | | | | | |
|---|---|---|---|---|---|---|---|---|---|---|---|---|---|---|
| Component | 1 | 2 | 3 | 4 | 5 | 6 | 7 | 8 | 9 | 10 | 11 | 12 | 13 | 14 |
| 3α-OH-5β-pregnan-20-one | 5.6 | 5.2 | 6.0 | 6.5 | 6.5 | 5.5 | 6.4 | 7.0 | 4.9 | 3.0 | 4.8 | 8.5 | 6.8 | 6.5 |
| Glyceryl monocaprylate | 81.4 | 19.1 | 43.3 | 17.3 | 52.7 | 42.3 | 19.7 | 63.7 | | | | | | |
| Glyceryl mono/ dicaprylocaprate | | 36.4 | | 58.9 | | | | | 43.2 | 41.2 | | | | |
| Propylene Glycol Monocaprylate | | | 2.4 | | | | 24.8 | | | | 57.5 | | 16.0 | |
| Alpha-tocopherol | 4.6 | 11.7 | 22.0 | 10.6 | 20.5 | 19.7 | 11.1 | 21.3 | 31.1 | 4.8 | 18.5 | 32.3 | 22.0 | 47.5 |
| Peppermint oil | | | | | | | | | | | | 43.6 | 28.2 | |
| TPGS | | | | | 8.8 | | | | | 27.5 | | | 15.0 | 6.2 |
| Hydrophilic additive (e.g., POLYOXYL 40 HYDROGENATED CASTOR OIL, POLYOXYL 35 HYDROGENATED CASTOR OIL) | 4.9 | 27.6 | 24.0 | 6.7 | 11.5 | 14.5 | 8.0 | 8.0 | 20.8 | 23.5 | 14.5 | 10.5 | 9.0 | 11.3 |
| Polyglyceryl-10 mono/di-oleate | | | | | | 16.8 | | | | | | | | 24.0 |
| Other ingredients | 3.5 | q.s. | 2.3 | q.s. | q.s. | 1.2 | q.s. | q.s. | q.s. | q.s. | 4.7 | 5.1 | 3.0 | 4.5 |
| Ratio of 5α3βP*/Alpha-tocopherol | 1.22 | 0.44 | 0.27 | 0.61 | 0.32 | 0.28 | 0.58 | 0.33 | 0.16 | 0.63 | 0.26 | 0.26 | 0.31 | 0.14 |

TABLE E-continued

| Oral Dosage Forms Comprising Noncrystalline Forms of 3α-OH-5β-pregnan-20-one | | | | | | | | | | | | | | |
|---|---|---|---|---|---|---|---|---|---|---|---|---|---|---|
| | Dosage form E (w/w %) | | | | | | | | | | | | | |
| Component | 1 | 2 | 3 | 4 | 5 | 6 | 7 | 8 | 9 | 10 | 11 | 12 | 13 | 14 |
| Ratio of 5α3βP/ medium chain monoglyceride | 0.07 | 0.27 | 0.14 | 0.38 | 0.12 | 0.13 | 0.13 | 0.11 | N/A | N/A | N/A | N/A | N/A | N/A |
| Ratio of Alpha-tocopherol/hydrophilic surfactant | 0.94 | 0.42 | 0.92 | 1.58 | 1.78 | 1.36 | 1.39 | 2.66 | 1.50 | 0.20 | 1.28 | 3.08 | 2.44 | 4.20 |

*5α3βP is 3α-OH-5β-pregnan-20-one.

As shown in the Table E, the oral dosage forms disclosed herein may provide a ratio of 3α-OH-5β-pregnan-20-one to alpha-tocopherol of less than 1.3, such as any one of about 0.1 to 1.3, about 0.1, about 0.2, about 0.3, about 0.4, about 0.5, about 0.6, about 0.7, about 0.8, about 0.9, about 1.0, about 1.1, about 1.2, and about 1.3.

In one example, the oral dosage forms may provide a ratio of 3α-OH-5β-pregnan-20-one to medium chain monoglyceride less than or equal to about 0.4, about 0.3, about 0.2, about 0.15, such as about 0.15, about 0.13, about 0.11, about 0.1, about 0.09, about 0.08, about 0.07, about 0.06, about 0.05, about 0.04, about 0.03, about 0.02, and about 0.01.

In another example, the oral dosage forms may provide a ratio of alpha-tocopherol to a hydrophilic additive of from about 0.05 to about 4.2, such as any one of about 0.05, about 0.1, about 0.3, about 0.5, about 0.7, about 0.9, about 1.1, about 1.3, about 1.4, about 1.7, about 2.0, about 2.3, about 2.6, about 2.9, about 3.2, about 3.5, and about 4.2.

TABLE F1

| Oral Drink Dosage Compositions Comprising 3α-OH-5β-pregnan-20-one | | | | | |
|---|---|---|---|---|---|
| | Composition F1 (w/w %) | | | | |
| Component* | I | II | III | IV | V |
| 3α-OH-5β-pregnan-20-one | 0.067-2 | 0.067-2 | 0.067-2 | 0.067-2 | 0.067-2 |
| Vitamin E or its derivatives (e.g., TPGS, tocopherol, tocopherol acetate, tocotrienol, or a combination) | | | | 0.067-6.67 | 0.067-6.67 |
| Lipophilic additive (e.g., glyceryl monocaprylate, glyceryl mono and dicaprylocaprate, propylene glycol monolaurate, propylene glycol monocaprylate, sorbitan monolaurate, glyceryl monolinoleate, sorbitan monooleate, linoleoyl polyoxyl-6 glycerides, polyglyceryl 3-oleate, oleoyl polyoxyl-6 glyceride, peppermint oil, caprylic acid, oleic acid, castor oil, linoleic acid, and a combination thereof) | 0.33-5.67 | | 0.067-4.67 | 0.067-4.67 | |
| Hydrophilic additive (s) (e.g., PEG-35 castor oil, PEG-40 hydrogenated castor oil, polysorbate 80, polysorbate 20, polyglyceryl-10 monooleate, polyglyceryl-10 dioleate, polyglyceryl-10 monocaprylate, polyglyceryl-10 dicaprylate, glyceryl-10 caprylate/caprate, glyceryl-10 monocaprate, caprylocaproyl polyoxyl-8 glyceride, tocopherol polyethylene glycol succinate, lauroyl PEG-32 glyceride, and a combination thereof) | | 0.33-5.67 | 0.33-6.00 | 0.33-6.00 | 0.33-6.00 |
| Purified Water | q.s to 100% | q.s to 100% | q.s to 100% | q.s to 100% | q.s to 100% |

*Components in the drink compositions may comprise optional other ingredients comprising at least, but not limited to, one of flavoring agents, sweeteners, antimicrobial preservatives, antioxidants, and edible fat.

TABLE F2

| Drink Dosage Forms Comprising 3α-OH-5β-pregnan-20-one | | | | | |
|---|---|---|---|---|---|
| | Drink dosage form F2 (% w/w) | | | | |
| Component* | I | II | III | IV | V |
| 3α-OH-5β-pregnan-20-one | 0.54 | 0.94 | 0.86 | 0.58 | 0.94 |
| Glyceryl monocaprylate | 2.07 | 3.13 | 3.00 | 3.07 | 3.07 |
| Polyoxyl 40 hydrogenated castor oil | 3.67 | 1.67 | 1.67 | 3.15 | 1.77 |
| Alpha-tocopherol | 0.67 | 1.33 | 0.93 | 0.17 | 1.37 |
| Propylene glycol monolaurate | | | 0.63 | | |
| Purified Water | q.s. to 100% | q.s. to 100% | q.s. to 100% | q.s. to 100% | q.s. to 100% |

*Components in the drink compositions may comprise optional other ingredients comprising at least, but not limited to, one of flavoring agents, sweeteners, antimicrobial preservatives, antioxidants, and edible fat.

TABLE F3

| Drink Dosage Forms Comprising 3α-OH-5β-pregnan-20-one | | | | |
|---|---|---|---|---|
| | Drink dosage form F3 (% w/w) | | | |
| Component* | I | II | III | IV |
| 3α-OH-5β-pregnan-20-one | 1.2 | 1.02 | 0.6 | 1.26 |
| Glyceryl monocaprylate | 4.25 | 5.53 | | 4.13 |
| Polyoxyl 40 hydrogenated castor oil | 0.45 | 0.33 | 2.77 | |
| Alpha-tocopherol | 1.37 | 0.31 | 0.93 | 1.33 |
| TPGS | | | | 0.50 |
| Propylene glycol Monolaurate | | | 0.90 | |
| Oleoyl polyoxyl-6 glycerides | | | 1.17 | |
| Sorbitan monooleate | | | 0.60 | |
| Purified Water | q.s. to 100% | q.s. to 100% | q.s. to 100% | q.s. to 100% |

*Components in the drink compositions may comprise optional other ingredients comprising at least, but not limited to, one of flavoring agents, sweeteners, antimicrobial preservatives, antioxidants, and edible fat.

In one embodiment, the oral solid dosage forms of the present disclosure may be formulated to include from about 30 mg to about 600 mg of 3α-OH-5β-pregnan-20-one which is treated, and a plurality of additives comprising at least one surfactant. In another embodiment, the oral solid dosage form may include about 30 mg to about 500 mg of 3α-OH-5β-pregnan-20-one which is treated, and a plurality of additives comprising at least one surfactant. In yet a further embodiment, the oral solid dosage form may include about 30 mg to about 400 mg of 3α-OH-5β-pregnan-20-one which is treated, and a plurality of additives comprising at least one surfactant. In another embodiment, the oral solid dosage form may include about 100 mg to about 400 mg of 3α-OH-5β-pregnan-20-one which is treated, and a plurality of additives comprising at least one surfactant. In yet another embodiment, the oral solid dosage form may include about 150 mg to about 750 mg of 3α-OH-5β-pregnan-20-one which is treated, and a plurality of additives comprising at least one surfactant. In yet another embodiment, the oral solid dosage form may include about 30 mg to about 300 mg of 3α-OH-5β-pregnan-20-one which is treated, and a plurality of additives comprising at least one surfactant. In a further embodiment, the oral solid dosage form may include about 30 mg to about 200 mg of 3α-OH-5β-pregnan-20-one which is treated, and a plurality of additives comprising at least one surfactant. In a further embodiment, the oral solid dosage form may include about 30 mg, about 40 mg, about 50 mg, about 60 mg, about 70 mg, about 80 mg, about 90 mg, about 100 mg, about 150 mg, about 200 mg, about 250 mg, about 300 mg, about 350 mg, about 400 mg, about 500 mg, about 550 mg, or about 600 mg of 3α-OH-5β-pregnan-20-one which is treated, and a plurality of additives comprising at least one surfactant.

The solid form of 3α-OH-5β-pregnan-20-one in the composition may comprise from about 5 wt % to about 60 wt % of the oral solid dosage form described herein. In one embodiment, the 3α-OH-5β-pregnan-20-one may comprise from about 10 wt % to about 45 wt % of the oral solid dosage form. In the compositions and forms of the present invention, 3α-OH-5β-pregnan-20-one may be treated, as needed. In another embodiment, the oral solid dosage form may include a combination of these forms. In another embodiment, 3α-OH-5β-pregnan-20-one may be present or added to the oral solid dosage form comprising at least one surfactant as a treated form such as amorphous, micronized, nano-sized, milled, sieved forms, or combinations thereof 3α-OH-5β-pregnan-20-one may be dispersed within the oral solid dosage form. The dispersed portion of 3α-OH-5β-pregnan-20-one may be partially or completely micronized, nanosized, milled, sieved, amorphous forms or combinations thereof.

3α-OH-5β-pregnan-20-one in the oral solid dosage forms of the present invention may be partially or fully in the form of high-energy solid which increases the release rate in an aqueous medium significantly as compared to its untreated crystalline forms (low energy forms). Examples of high-energy solid forms of 3α-OH-5β-pregnan-20-one include amorphous forms, solid dispersion forms, solid solution forms, eutectic forms, and the like after association with the additives in the composition. In one embodiment, a high-energy form of 3α-OH-5β-pregnan-20-one in the present invention may be physico-chemically stable for at least one month. In yet another embodiment, the high-energy form of 3α-OH-5β-pregnan-20-one may be physically and/or chemically associated with at least one additional substance, such as for example, alcohol, pyrollidone, cellulose, poloxamer, polyol, polyethylene glycol, dextrins, cyclodextrins, and the like. Several methods known in the art may be used to produce a high-energy form of 3α-OH-5β-pregnan-20-one in the present invention; for example, co-precipitation, solid-solution, co-melting, co-grinding, hot melt extrusion, hot melt spraying, spray drying with co-solvent, controlled precipitation from super-saturated solutions, solidified supersaturated solutions, and combinations thereof.

The oral solid dosage forms of the present disclosure may include one or more pharmaceutically acceptable additives. The pharmaceutical acceptable additives may be selected from a wide range of compounds and classes of compounds. The pharmaceutically acceptable additives may comprise from 40 wt % to about 99.5 wt % of the oral solid dosage form. In one embodiment, the pharmaceutically acceptable additives may comprise about 50 wt % to 90 wt % of the oral dosage form. In one embodiment, the pharmaceutically acceptable additives may comprise about 50 wt % to 85 wt % of the oral solid dosage form. In yet another embodiment, the pharmaceutically acceptable additives may comprise about 50 wt % to 70 wt % of the oral solid dosage form.

Non-limiting examples of compounds that may be used as at least a part of the pharmaceutically acceptable additives include, without limitation, celluloses; dextrins, gums, carbomers, methacrylates, sugars, lactoses, inorganic carbonates, oxides, chlorides, sulphates; salts of calcium; salts of magnesium; salts of fatty acids; inorganic and organic acids, bases and salts; propylene glycol; glycerols; fatty acids; fatty alcohols; fatty acid esters; glycerol esters; mono-, di- or triglycerides; edible oils; omega oils; vegetable oils, hydrogenated vegetable oils; partially or fully hydrogenated vegetable oils; glycerol esters of fatty acids; waxes; alcohols; gelatin; polyethylene glycol; polyethylene oxide co-polymers; silicates; antioxidants, tocopherols, sugar stearates, starches, shellac, resins, proteins, acrylates; methyl copolymers; polyvinyl alcohol; starch; phthalates; and combinations thereof.

It is important to note that additives in compositions used in the present invention may serve multiple functional purposes within the oral solid dosage form. For example, an additive may also function as a filler, a binder, a diluent, a disintegrant, a lubricant, a glidant, a preservative, a sweetener, a flavor, a coating agent, a colorant, an antioxidant, or a release modulator.

The oral solid dosage form(s) are not limited with respect to size, shape or general configuration, and may be formulated into a variety of the dosage forms including, but not limited to, two-piece hard gelatin capsules, soft gelatin capsules, beads, beadlets, granules, spherules, pellets, microcapsules, microspheres, nanospheres, nanocapsules, tablets, or combinations thereof. Other oral solid dosage forms known to those of ordinary skill in the art may also be used. In one aspect, the oral solid dosage form may be a capsule or tablet. In one embodiment, the oral solid dosage form may be a matrix tablet.

The coating may be applied by conventional techniques, such as by pan coaters, rotary granulators and fluidized bed coaters such as top-spray, tangential-spray or bottom-spray (Wurster coating), and most preferably by the latter. One preferred coating solution consists of about 40 wt % EUDRAGIT L30-D55 and 2.5 wt % triethylcitrate in about 57.5 wt % water. This enteric coating solution may be coated onto the core of the oral dosage form using a pan coater. The enteric coating materials listed above may be used to granulate a 3α-OH-5β-pregnan-20-one containing mixture. The resultant granulate may be filled into capsules or compressed to form tablets or caplets. The release of 3α-OH-5β-pregnan-20-one from the oral dosage forms or components of the dosage form (e.g. granules) of the present disclosure may be controlled or delayed.

Several oral dosage forms comprising solid forms of 3α-OH-5β-pregnan-20-one are prepared using the components as set forth in Tables H and I. The examples of the oral dosage forms described herein may be prepared generally as solid dosage forms, such as a tablet. In an aspect, the oral dosage forms are prepared by mixing the processing aids and at least one surfactant with 3α-OH-5β-pregnan-20-one to form a homogenous powder blend. In another aspect, the amount of surfactant in the composition may be greater than 0.5% (w/w) of the composition. The powder blend may be compressed to form tablets by direct compression or after dry or wet granulation process steps. In case of wet granulation, a solution of binder (e.g., PVP K30) may be used for granulation. The binder solution may optionally contain a portion (or all) of the amount of at least one surfactant when a surfactant is present in the dosage form. Following granulation, the resultant product may be dried, sieved, and compressed into tablets.

The solid dosage forms of 3α-OH-5β-pregnan-20-one may comprise crystalline or noncrystalline solid forms of 3α-OH-5β-pregnan-20-one. The final 3α-OH-5β-pregnan-20-one form in the dosage form may be a result of the processing technique employed such as size reduction, coating, spraying, drying, hot melt extrusion, etc. The final form of 3α-OH-5β-pregnan-20-one in the solid dosage forms may be milled, micronized, nanosized, amorphous, solid solution or dispersion, or eutectic mixture. The solid dosage form may be in the form of a capsule, a tablet, or a powder, or a granule, or a pellet.

The oral compositions comprising solid forms of 3α-OH-5β-pregnan-20-one in the present disclosure may be formulated to provide % release rates that may yield enhanced therapeutic effects of the 3α-OH-5β-pregnan-20-one for treatment of CNS disorders. The in vitro percent release of 3α-OH-5β-pregnan-20-one from these oral compositions may be obtained by measuring the percent release of 3α-OH-5β-pregnan-20-one for at least 4 hours post inserting the oral composition into a USP Type-II dissolution apparatus in an aqueous media with sink conditions at about 75-100 rpm at 37° C. and using a HPLC method.

In one aspect, the oral compositions comprising treated solid forms of 3α-OH-5β-pregnan-20-one in this invention may be disintegrated less than 25 min in an aqueous media. In another aspect, the oral compositions comprising treated solid forms of 3α-OH-5β-pregnan-20-one in this invention may be disintegrated less than 20 min in an aqueous media. In further aspect, the oral compositions comprising treated solid forms of 3α-OH-5β-pregnan-20-one in this invention may be disintegrated less than 20 min, such as less than one of 19 min, 18 min, 16 min, 15 min, 14 min, 13 min, 12 min, 11 min, 10 min, 9 min, 8 min, 7 min, 6 min, 5 min, 4 min, 3 min, 2 min, and 1 min in an aqueous media.

In one aspect, the oral dosage forms disclosed herein may be formulated with the 3α-OH-5β-pregnan-20-one treated from the original powder of 3α-OH-5β-pregnan-20-one. For example, one of the treated 3α-OH-5β-pregnan-20-one in this invention is the micronized powder of 3α-OH-5β-pregnan-20-one, which has a particle size distribution of D90=16 μm. In another aspect, the oral dosage forms may be prepared for immediate release to improve bioavailability, including processing aids and at least one of surfactants with treated 3α-OH-5β-pregnan-20-one to form a homogenous powder blend. Table G shows some exemplary oral solid compositions of the present invention comprising treated solid forms of 3α-OH-5β-pregnan-20-one for immediate release, with any surfactant.

TABLE G

Oral compositions comprising treated 3α-OH-5β-pregnan-20-one

| Component | Composition G (w/w %) | | | | | | | | | | |
|---|---|---|---|---|---|---|---|---|---|---|---|
| | 1 | 2 | 3 | 4 | 5 | 6 | 7 | 8 | 9 | 10 | 11 |
| 3α-OH-5β-pregnan-20-one, treated† | 5-45 | 10-40 | 10-40 | 10-45 | 18-40 | 18-33 | 18-33 | 20-30 | 40-50 | 20-30 | 5-15 |
| Surfactant (e.g. polysorbate 80, polyoxyl 40 hydrogenated castor oil, sodium lauryl sulfate, poloxamer, sodium docusate, TPGS, etc.) | 1-25 | 15-30 | 1-25 | 1-25 | 1-25 | 1-20 | 5-10 | 5-10 | 10-50 | 1-25 | 5-15 |
| Processing aids* | q.s. | q.s. | q.s. | q.s. | q.s. | q.s. | q.s. | q.s. | q.s. | q.s. | q.s. |
| Total | 100% | 100% | 100% | 100% | 100% | 100% | 100% | 100% | 100% | 100% | 100% |

*Processing aids may comprise, but not limited to, fillers, binders, diluents, disintegrants, lubricants, glidants, preservatives, sweeteners, flavors, coating agents, colorants, antioxidants, release modulators, water, etc.
†Treated is defined as grinded, sieved, micronized or nanosized, milled, amorphous, or fully solubilized.

In another example, Table H shows some preferred oral compositions of the present invention comprising solid forms of 3α-OH-5β-pregnan-20-one for immediate release, with any surfactant.

TABLE H

Preferred oral compositions comprising treated solid forms of 3α-OH-5β-pregnan-20-one

| Component | Composition H (w/w %) | | | | | | | |
|---|---|---|---|---|---|---|---|---|
| | 1 % | 2 % | 3 % | 4 % | 5 % | 6 % | 7 % | 8 % |
| 3α-OH-5β-pregnan-20-one, treated† | 19.6 | 9.3 | 22.5 | 16.9 | 19.2 | 26.0 | 33.3 | 40.0 |
| Binder (e.g. Crospovidone)* | | 12.7 | | 9.0 | | 16.2 | 9.0 | 9.0 |
| Binder (e.g. PEG 6000)* | 25.4 | | 22.5 | | 25.0 | 23.1 | | |
| Surfactant (e.g. Poloxamer 188, 407)** | 10.9 | 16.3 | 18.7 | 10.0 | 10.6 | 8.0 | | 10.0 |
| Surfactant (e.g. Sodium lauryl sulphate)** | | | | | | 4.0 | 8.0 | |
| Filler (e.g. Microcrystalline cellulose) | | 60.2 | 35.3 | 63.1 | | 21.5 | 48.6 | 40.0 |
| Filler (e.g. Lactose monohydrate) | 42.9 | | | | 44.0 | | | |
| Glidant (e.g. Magnesium stearate)*** | 0.2 | | 0.2 | | 1.2 | 0.2 | | |
| Lubricant (e.g. Stearic acid)**** | 1.0 | 1.5 | 0.8 | 1.0 | | 1.0 | 1.0 | 1.0 |
| Processing aids† | q.s. | q.s. | q.s. | q.s. | q.s. | q.s. | q.s. | q.s. |

†Treated is defined as grinded, sieved, micronized or nanosized milled, or amorphous in this table.

*Binder may additionally comprise, but not limited to, povidone, copovidone, crospovidone, polyvinylpyrrolidone, starch, sucrose, polyethylene glycol, cellulose, lactose, crosscaramellose sodium, and gelatin.

**Surfactant may additionally comprise, but not limited to, sodium lauryl sulphate, TPGS, cyclodextrin, polysorbate, sodium lauryl ethoxy sulphate, sodium lauryl sulfate, sodium docusate, and hydrogenated polyoxyl castor oil.

***Glidant may additionally comprise, but not limited to, magnesium carbonate, glyceryl distearate, glyceryl palmitostearate, ascorbyl palmitate, calcium palmitate, starch, and talc.

****Lubricant may additionally comprise, but not limited to, stearic acid, stearin, glyceryl dibehenate, sodium stearyl fumarate, glyceryl distearate, glyceryl palmitostearate, PEG, boric acid, and waxes.

†Processing aids, except the functional component shown in the table, may additionally be added with, but not limited to, release modulators, disintegrants, preservatives, sweeteners, flavors, coating agents, colorants, antioxidants, and water.

Example 2. Oral Dosage Formulations Comprising 3α-OH-5β-pregnan-20-one

Solubility, dispersibility, and dissolution tests were performed and compared between a variety of exemplary oral dosage formulations comprising 3α-OH-5β-pregnan-20-one in solid, liquid, and suspension forms. Table I displays various exemplary oral dosage formulations comprising 3α-OH-5β-pregnan-20-one in order to assess the effect of formulations on solubility, dispersibility, and dissolution, which may affect the bioavailability (or absorption into the body) of 3α-OH-5β-pregnan-20-one for subjects in need of 3α-OH-5β-pregnan-20-one therapy.

TABLE I

Oral Dosage Formulations Comprising 3α-OH-5β-pregnan-20-one

| | Formulation # (% w/w) | | | | | | | | | | | |
|---|---|---|---|---|---|---|---|---|---|---|---|---|
| Component | 1 | 2 | 3 | 4 | 5 | 6 | 7 | 8 | 9 | 10 | 11 | 12 |
| 3α-OH-5β-pregnan-20-one | 5.2 | 6.5 | 8.5 | 9.3 | 3 | 3 | 1 | 1 | 1 | 1 | 0.5 | 8.5 |
| Glyceryl monocaprylate | 19.1 | 17.3 | | | | | | | 19.1 | 17.3 | | |
| Glyceryl mono/dicaprylocaprate | 36.4 | 58.9 | | | | | | | 40.6 | 64.4 | | |
| Polyoxyl 40 hydrogenated castor oil | 27.6 | 6.7 | | | | | | | 27.6 | 6.7 | | |
| Alpha-Tocopherol | 11.7 | 10.6 | | | | | | | 11.7 | 10.6 | | |
| Poloxomer 407 | | | 10 | | | | | | | | | 0.4 |
| Microcrystalline Cellulose | | | 72.5 | 76.9 | | | | | | | | 82.1 |
| Crosscaramellose sodium | | | 8 | 12.8 | | | | | | | | 8 |
| Lubricant (e.g. Stearic acid) | | | 1 | 1 | | | | | | | | 1 |
| Canola Oil | | | | | 97 | | | 99 | | | | |
| Polysorbate 80 | | | | | | 97 | | | | | | |
| Medium chain tryglyceride (e.g. MIGLYOL 812) | | | | | | | 99 | | | | | |
| SBE-β-CD | | | | | | | | | | | 25 | |
| Purified Water | — | — | q.s. | q.s. | — | — | — | — | — | — | 74.5 | q.s. |

The 3α-OH-5β-pregnan-20-one release rate was obtained from one each of composition Formulations #1, #2, and #3, by exposing one gram of each composition in a USP Type II dissolution apparatus in 900 mL of deionized water with 0.5% (w/v) of sodium lauryl sulfate at 75 rpm at 37° C. Results were compared to release rates for compositions consisting of a conventional tablet formulation without a surfactant (Formulation #4), a formulation of crystalline 3α-OH-5β-pregnan-20-one suspension in canola oil (Formulation #5), and a formulation of crystalline 3α-OH-5β-pregnan-20-one suspension in polysorbate 80 (Formulation #6). The dose amount of 3α-OH-5β-pregnan-20-one per unit used for the release test shown in FIG. 2 was 52 mg/g, 65 mg/g, 85 mg/g, 93 mg/g, 30 mg/g, 30 mg/g for Formulation #1, #2, #3, #4, #5, #6, respectively.

Dispersibility of the disclosed oral compositions comprising 3α-OH-5β-pregnan-20-one (Formulation #9 and #10) was performed in an aqueous dilution (×100) with pH 6.8 simulated intestinal fluid per USP 26. The dispersibility results were compared to dispersibility of compositions comprising solubilized 3α-OH-5β-pregnan-20-one in a medium chain triglyceride (e.g. MIGLYOL 812, Formulation #7) and in canola oil (Formulation #8).

Release Performance Results in FIG. 2

FIG. 2 shows plots of the 3α-OH-5β-pregnan-20-one release rate obtain for Formulation #1, #2, and #3 compared to conventional compositions of Formulation #4, #5, and #6). The dose amount of 3α-OH-5β-pregnan-20-one per unit used for the release test shown in FIG. 2 was 52 mg/g, 65 mg/g, 85 mg/g, 93 mg/g, 30 mg/g, 30 mg/g for Formulation #1, #2, #3, #4, #5, #6, respectively. The 3α-OH-5β-pregnan-20-one, in these formulations, was treated (e.g., micronized) before formulation of the composition.

In one example, as shown in FIG. 2, compositions of the present invention may release at least 45 mg of the 3α-OH-5β-pregnan-20-one after 30 minutes when measured using a USP Type II dissolution apparatus in 900 mL of deionized water with 0.5% (w/v) of sodium lauryl sulfate at 75 rpm at 37° C.

In another example, as shown in FIG. 2, compositions of the present invention may release at least 70% of the 3α-OH-5β-pregnan-20-one after 30 minutes when measured using a USP Type II dissolution apparatus in 900 mL of deionized water with 0.5% (w/v) of sodium lauryl sulfate at 75 rpm at 37° C.

In a further example, as shown in FIG. 2, compositions of the present invention may release greater than about 35 mg of the 3α-OH-5β-pregnan-20-one after 15 minutes when measured using a USP Type II dissolution apparatus in 900 mL of deionized water with 0.5% (w/v) of sodium lauryl sulfate at 75 rpm at 37° C.

In yet further example, as shown in FIG. 2, compositions of the present invention may release at least 50% of the 3α-OH-5β-pregnan-20-one after 15 minutes when measured using a USP Type II dissolution apparatus in 900 mL of deionized water with 0.5% (w/v) of sodium lauryl sulfate at 75 rpm at 37° C.

In yet further example, as shown in FIG. 2, compositions of the present invention may release at least 25% more of the 3α-OH-5β-pregnan-20-one as compared with compositions consisting essentially of a conventional tablet formulation without a surfactant (Formulation #4), a formulation of crystalline 3α-OH-5β-pregnan-20-one suspension in canola oil (Formulation #5), and a formulation of crystalline 3α-OH-5β-pregnan-20-one suspension in polysorbate 80 (Formulation #6) after 30 minutes when measured using a USP Type II dissolution apparatus in 900 mL of deionized water with 0.5% (w/v) of sodium lauryl sulfate at 75 rpm at 37° C.

In one example not shown in FIG. 2, compositions of the present invention may release at least 20% more of the 3α-OH-5β-pregnan-20-one as compared with a composition of a tablet formulation with a surfactant less than 0.5% (w/w) of the composition (Formulation #12) after 30 minutes when measured using a USP Type II dissolution apparatus in 900 mL of deionized water with 0.5% (w/v) of sodium lauryl sulfate at 75 rpm at 37° C. In another example, compositions of the present invention have a faster disintegration time (e.g., less than 25 min) than that of tablet forms comprising a surfactant of less than 0.5% (w/w) of the composition (Formulation #4 and #12).

In yet further example, as shown in FIG. 2, a conventional solid dosage form composition devoid of a surfactant (e.g., Formulation #4) may release less than about 45 mg of the 3α-OH-5β-pregnan-20-one after 30 minutes when measured using a USP Type II dissolution apparatus in 900 mL of deionized water with 0.5% (w/v) of sodium lauryl sulfate at 75 rpm at 37° C.

In yet another embodiment, in a method of using the composition disclosed herein, the composition comprising a 3α-OH-5β-pregnan-20-one 30 minute initial release rate that comprises at least one of: A) at least one of 10%, 15%, 20%, and 25% greater than a 3α-OH-5β-pregnan-20-one 30-minute post in vitro test initiation release rate of a first comparison composition consisting essentially of treated 3α-OH-5β-pregnan-20-one suspended in Tween 80, B) at least one of 10%, 15%, 20%, and 25% greater than a 3α-OH-5β-pregnan-20-one 30-minute post in vitro test initiation release rate of a second comparison composition consisting essentially of treated 3α-OH-5β-pregnan-20-one suspended in canola oil, and C) at least one of 10%, 15%, and 20% greater than a 3α-OH-5β-pregnan-20-one 30-minute post in vitro test initiation release rate of a third comparison composition comprising treated crystalline 3α-OH-5β-pregnan-20-one and a plurality of additives comprising a surfactant in an amount of no more than 0.5 wt % of said 3α-OH-5β-pregnan-20-one of said third comparison composition.

Dispersion Assessment Post Dilution with SIF in FIG. 3

FIG. 3 shows an image of the comparative dispersibility of the disclosed oral compositions comprising noncrystalline 3α-OH-5β-pregnan-20-one form (Formulation #9 and #10) exposed in an aqueous dilution (×100) with pH 6.8 simulated intestinal fluid per USP 26 compared to the dispersibility of the compositions comprising solubilized 3α-OH-5β-pregnan-20-one in medium chain triglyceride (e.g. MIGLYOL 812, Formulation #7) and in canola oil (Formulation #8).

As shown in FIG. 3, Formulation #7 and #8 (comprising 3α-OH-5β-pregnan-20-one solubilized in MIGLYOL 812 and canola oil, respectively) were not dispersed or solubilized in the ×100 diluted pH 6.8 simulated intestinal fluid per USP 26 (oily contents at the surface were fully separated from the aqueous medium), while the compositions of the disclosed invention (Formulation #9 and #10) were well dispersed. UV Absorbance measured at 450 nm was not measurable for Formulation #7 and #8, while 1.3 Abs and 3.2 Abs was measured for Formulation #9 and #10, respectively.

Example 3. Oral Dosage Formulations Comprising Untreated 3α-OH-5β-pregnan-20-one Oral compositions comprising crystalline forms of untreated 3α-OH-5β-pregnan-20-one is expected to have a slower release rate of 3α-OH-5β-pregnan-20-one possibly due to particle size distribution of 3α-OH-5β-pregnan-20-one in the compositions. Table J displays various exemplary oral dosage formulations comprising untreated 3α-OH-5β-pregnan-20-one with expected release rate measured using a USP Type-II dissolution apparatus at about 75 rpm in 900 mL of an aqueous media at 37° C. having a sink condition of said 3α-OH-5β-pregnan-20-one.

TABLE J

| | Formulation (w/w %) | | |
|---|---|---|---|
| Component | J #1 % | J #2 % | J #3 % |
| 3α-OH-5β-pregnan-20-one, untreated* | 31.0 | 31.0 | 31.0 |
| Surfactant (e.g. Poloxamer 407)† | 10.0 | 0.3 | — |
| Binder (e.g. Crospovidone) | 9.0 | 9.0 | 9.0 |
| Filler (e.g. Microcrystalline cellulose) | 49.0 | 58.7 | 59.0 |
| Lubricant (e.g. Stearic acid) | 1.0 | 1.0 | 1.0 |
| Processing aids | q.s. | q.s. | q.s. |
| Release rate of 3α-OH-5β-pregnan-20-one in 30 min | <70% | <70% | <70% |

*Untreated has D10 > 20 μm and D50 = 55 μm.

What is claimed is:

1. An oral dosage form pharmaceutical composition for use in treating a CNS disorder, said composition comprising a predetermined quantity of treated 3α-OH-5b-pregnan-20-one and a plurality of additives, said plurality of additives comprising at least one lipophilic additive, wherein said composition comprises a 3α-OH-5β-pregnan-20-one 30 minute initial release rate that comprises at least one of:

at least one of 10%, 15%, 20%, and 25% greater than a 3α-OH-5β-pregnan-20-one 30-minute post in vitro test initiation release rate of a first comparison composition consisting essentially of treated 3α-OH-5β-pregnan-20-one suspended in polysorbate 80, at least one of 10%, 15%, 20%, and 25% greater than a 3α-OH-5β-pregnan-20-one 30-minute post in vitro test initiation release rate of a second comparison composition consisting essentially of treated 3α-OH-5β-pregnan-20-one suspended in canola oil, and at least one of 10%, 15%, and 20% greater than a 3α-OH-5β-pregnan-20-one 30-minute post in vitro test initiation release rate of a third comparison composition comprising treated crystalline 3α-OH-50-pregnan-20-one and a plurality of additives, said plurality of additives comprising a surfactant in an amount of no more than 0.5 wt % of said treated crystalline 3α-OH-5β-pregnan-20-one of said third comparison composition.

2. The composition of claim 1, wherein said composition has a disintegration time of less than at least one of about 25 minutes, about 20 minutes, about 15 minutes, about 10 minutes, about 5 minutes, about 3 minutes, about 2 minutes, and about 1 minute as measured according to (701) Disintegration, USP 43.

3. An oral dosage form pharmaceutical composition for use in treating a CNS disorder, said composition comprising a predetermined quantity of treated 3α-OH-5(-pregnan-20-one and a plurality of additives, said plurality of additives comprising at least one lipophilic additive, wherein when said treated 3α-OH-5β-pregnan-20-one is fully solubilized and is measured using a USP Type-II dissolution apparatus at about 75 rpm in 900 mL of an aqueous media at 37° C. having a sink condition of said treated 3α-OH-5β-pregnan-20-one, a 1 gram unit dosage form of said composition releases at least one of 6 mg, 8 mg, 10 mg, 15 mg, 20 mg, 25 mg, 30 mg, 35 mg, 40 mg, 45 mg, 50 mg, 60 mg, 70 mg, and 80 mg of said treated 3α-OH-5β-pregnan-20-one at about 30 minutes post administration.

4. The composition of claim 3, wherein said unit dosage form has a disintegration time of less than at least one of about 25 minutes, about 20 minutes, about 15 minutes, about 10 minutes, about 5 minutes, about 3 minutes, about 2 minutes, and about 1 minute as measured according to (701) Disintegration, USP 43.

5. An oral dosage form pharmaceutical composition for use in treating a CNS disorder, said composition comprising a predetermined quantity of treated 3α-OH-5b-pregnan-20-one and a plurality of additives, said plurality of additives comprising at least one lipophilic additive, wherein when measured using a USP Type-II dissolution apparatus at about 75 rpm in 900 mL of an aqueous media at 37° C. having a sink condition of said treated 3α-OH-50-pregnan-20-one, said composition releases at at least one of the following rates comprising:

at least about 70% of said treated 3α-OH-5β-pregnan-20-one at about 30 minutes post in vitro release test initiation, and at least about 50% of said treated 3α-OH-5β-pregnan-20-one at about 15 minutes post in vitro release test initiation.

6. The composition of claim 5, wherein said dosage form comprises a solid dosage form, and wherein said solid dosage form has a disintegration time of less than at least one of about 25 minutes, about 20 minutes, about 15 minutes, about 10 minutes, about 5 minutes, about 3 minutes, about 2 minutes, and about 1 minute as measured according to (701) Disintegration, USP 43.

7. An oral dosage form pharmaceutical composition for use in treating a CNS disorder, said composition comprising a predetermined quantity of treated 3α-OH-5β-pregnan-20-one and a plurality of additives, said plurality of additives comprising at least one lipophilic additive, wherein at least one of a crystalline form and a solid noncrystalline form of said treated 3α-OH-5β-pregnan-20-one comprises a disintegration time of less than at least one of about 25 minutes, about 20 minutes, about 15 minutes, about 10 minutes, about 5 minutes, about 3 minutes, about 2 minutes, and about 1 minute as measured according to (701) Disintegration, USP 43.

8. An oral dosage form pharmaceutical composition for use in treating a CNS disorder, said composition comprising a predetermined quantity of treated 3α-OH-5β-pregnan-20-one and a plurality of additives, said plurality of additives comprising at least one lipophilic additive, wherein when said composition is exposed in a 100× dilution with simulated intestinal fluid, with pH 6.8 per USP 26, said composition exhibits a dispersion of a UV absorbance (ABS) value of no more than 10 at a 450 nm wavelength.

9. An oral dosage form pharmaceutical composition for use in treating a CNS disorder, said composition comprising a predetermined quantity of treated 3α-OH-5β-pregnan-20-one and a plurality of additives, said plurality of additives comprising at least one lipophilic additive, wherein said treated 3α-OH-5β-pregnan-20-one comprises at least one of a crystalline form, a noncrystalline form, an amorphous form, and a fully solubilized form, and wherein said crystalline form of said treated 3α-OH-5β-pregnan-20-one comprises a particle size distribution of at least one of a D90 of less than 150 μm, a D10 of less than 20 μm, and a D50 of at least one of 0.15 μm to 50 μm, 30 μm to 50 μm, 0.3 to 30 μm, and 2 μm to 8 μm, and wherein when measured using a USP Type-II dissolution apparatus at about 75 rpm in 900 mL of an aqueous media at 37° C. having a sink condition of said treated 3α-OH-5β-pregnan-20-one, said composition releases at at least one of the following rates comprising:

at least about 70% of said treated 3α-OH-5β-pregnan-20-one at about 30 minutes post in vitro release test initiation, and at least about 50% of said treated 3α-OH-5β-pregnan-20-one at about 15 minutes post in vitro release test initiation.

10. The composition of claim 9, wherein said plurality of additives comprises at least one hydrophilic additive, and wherein said at least one lipophilic additive comprises at least one of a tocopherol or a derivative thereof, a fatty acid or a derivative thereof, a glyceryl fatty acid ester, a PEG glyceride of fatty acid ester, a polyglycerol fatty acid ester, a triglyceride, a propylene glycol fatty acid ester, an edible oil, a sterol or a derivative thereof, and an omega oil or a derivative thereof, and wherein said at least one hydrophilic additive comprises at least one of an alcohol-oil transesterification product, a polyoxyethylene hydrogenated vegetable oil; a polyoxyethylene vegetable oil; an alkyl sulphate salts, a dioctyl sulfosuccinate salt, a polyethylene glycol fatty acids ester, a polyethylene glycol fatty acids mono- and di-ester mixture, a polysorbate, a polyethylene glycol derivative of tocopherol, a polymer, and a combinations thereof.

11. The composition of claim 9, wherein said composition comprises a 3α-OH-5β-pregnan-20-one 30 minute post in vitro test initiation release rate that comprises at least one of:

at least one of 10%, 15%, 20%, and 25% greater than a 3α-OH-5β-pregnan-20-one 30-minute post in vitro test initiation release rate of a first comparison composition consisting essentially of treated 3α-OH-5β-pregnan-20-one suspended in polysorbate 80, at least one of 10%, 15%, 20%, and 25% greater than a 3α-OH-5β-pregnan-20-one 30-minute post in vitro test initiation release rate of a second comparison composition consisting essentially of treated 3α-OH-5β-pregnan-20-one suspended in canola oil, and at least one of 10%, 15%, and 20% greater than a 3α-OH-5β-pregnan-20-one 30-minute post in vitro test initiation release rate of a third comparison composition comprising treated crystalline 3α-OH-50-pregnan-20-one and a plurality of additives, said plurality of additives comprising a surfactant in an amount of no more than 0.5 wt % of said treated 3α-OH-5β-pregnan-20-one of said third comparison composition.

12. An oral dosage form pharmaceutical composition for use in treating a CNS disorder, said composition comprising a predetermined quantity of treated 3α-OH-5β-pregnan-20-one and a plurality of additives, said plurality of additives comprising at least one lipophilic additive, wherein said composition has a disintegration time of less than at least one of about 25 minutes, about 20 minutes, about 15 minutes, about 10 minutes, about 5 minutes, about 3 minutes, about 2 minutes, and about 1 minute as measured according to (701) Disintegration, USP 43.

* * * * *